(12) United States Patent
Dietz et al.

(10) Patent No.: US 8,597,646 B2
(45) Date of Patent: Dec. 3, 2013

(54) METHODS AND COMPOSITONS FEATURING TGF-BETA ANTAGONISTS FOR THE TREATMENT OF MARFAN SYNDROME AND ASSOCIATED DISORDERS

(75) Inventors: Harry C. Dietz, Towson, MD (US);
Daniel P. Judge, Baltimore, MD (US);
Enid R. Neptune, Baltimore, MD (US);
Ronald Cohn, Pikesville, MD (US);
Jennifer Habashi, Annapolis, MD (US)

(73) Assignee: The Johns Hopkins University, Baltimore, MD (US)

(*) Notice: Subject to any disclaimer, the term of this patent is extended or adjusted under 35 U.S.C. 154(b) by 410 days.

(21) Appl. No.: 12/084,098

(22) PCT Filed: Oct. 25, 2006

(86) PCT No.: PCT/US2006/041846
§ 371 (c)(1),
(2), (4) Date: Oct. 19, 2009

(87) PCT Pub. No.: WO2007/050793
PCT Pub. Date: May 3, 2007

(65) Prior Publication Data
US 2010/0034806 A1    Feb. 11, 2010

Related U.S. Application Data

(60) Provisional application No. 60/729,976, filed on Oct. 25, 2005.

(51) Int. Cl.
*A61K 39/395* (2006.01)
*C07K 16/22* (2006.01)
*C07K 14/495* (2006.01)

(52) U.S. Cl.
USPC .................. 424/145.1; 424/133.1; 424/135.1; 424/158.1; 530/387.1; 530/387.36; 530/388.23; 530/389.2

(58) Field of Classification Search
None
See application file for complete search history.

(56) References Cited

U.S. PATENT DOCUMENTS

| | | | |
|---|---|---|---|
| 7,462,185 B1 * | 12/2008 | Knodel | 606/139 |
| 2003/0153524 A1 * | 8/2003 | Hinton et al. | 514/44 |
| 2004/0197333 A1 * | 10/2004 | Suthanthiran et al. | 424/145.1 |

FOREIGN PATENT DOCUMENTS

| WO | WO-00/40227 A2 | 7/2000 |
|---|---|---|
| WO | WO-2005/004913 | 1/2005 |

OTHER PUBLICATIONS

P. H. Byers, J. Clin. Inves. 114(2):161, Jul. 2004.*
Neptune et al., Nature Genetics 33:407, 2003.*
Mizuguchi et al., Nature Genetics 36(8):855, Aug. 2004.*
Kelly et al. Intercellular adhesion molecule-1-deficient mice are protected against ischemic renal injury. J Clin Invest. Feb. 15, 1996;97(4):1056-63.*
Bartram U et al. "The role of transforming growth factor beta in lung development and disease." Chest. Feb. 2004;125(2):754-65.
Bogdanovich S et al. "Functional improvement of dystrophic muscle by myostatin blockade." Nature. Nov. 28, 2002;420(6914):418-21.
Ghosh J et al. "The role of transforming growth factor beta1 in the vascular system." Cardiovasc Pathol. Jan.-Feb. 2005;14(1):28-36.
Gelb BD et al. "Marfan's syndrome and related disorders—more tightly connected than we thought." N Engl J Med. Aug. 24, 2006;355(8):841-4.
Habashi JP et al. "Losartan, an AT1 antagonist, prevents aortic aneurysm in a mouse model of Marfan syndrome." Science. Apr. 7, 2006;312(5770):117-21.
Habashi JP et al. "Losartan arrests aortic root enlargement in marfan syndrome independent of hemodyamic effects" Circulation. Oct. 2005; 112(17), Suppl. S:U440.
Kushibiki T et al. "Delivery of plasmid DNA expressing small interference RNA for TGF-beta type II receptor by cationized gelatin to prevent interstitial renal fibrosis." J Control Release. Jul. 20, 2005;105(3):318-31.
Lavoie P. et al. "Neutralization of transforming growth factor-beta attenuates hypertension and prevents renal injury in uremic rats." J Hypertens. Oct. 2005;23(10):1895-903.
Lim DS et al. "Angiotensin II blockade reverses myocardial fibrosis in a transgenic mouse model of human hypertrophic cardiomyopathy." Circulation. Feb. 13, 2001;103(6):789-91.
Maruno KA et al. "Apoptosis is a feature of TGF beta-induced cataract." Clin Exp Optom. Mar. 2002;85(2):76-82.
Neptune ER et al. "Dysregulation of TGF-beta activation contributes to pathogenesis in Marfan syndrome." Nat Genet. Mar. 2003;33(3):407-11.
NG CM et al. "TGF-beta-dependent pathogenesis of mitral valve prolapse in a mouse model of Marfan syndrome." J Clin Invest. Dec. 2004;114(11):1586-92.
Pannu H et al. " Mutations in transforming growth factor-beta receptor type II cause familial thoracic aortic aneurysms and dissections." Circulation. Jul. 26, 2005;112(4):513-20.
Strausberg RL et al. "Generation and initial analysis of more than 15,000 full-length human and mouse cDNA sequences."Proc Natl Acad Sci U S A. Dec. 24, 2002;99(26):16899-903.
Wahl Sm et al. "Reversal of acute and chronic synovial inflammation by anti-transforming growth factor beta." J Exp Med. Jan. 1, 1993;177(1):225-30.
International Search Report, International Application No. PCT/US2006/41846, dated Aug. 4, 2007 and mailed Oct. 1, 2007.
Supplementary European Search Report, European Application No. EP 06 82 6778 dated Aug. 11, 2009 and mailed Aug. 24, 2009.
The Lung Perspectives, Jul. 1, 2005, vol. 13, No. 3, pp. 83-88.
Journal of Japan Surgical Society, Extra Edition, 2004, vol. 105, p. 363.
Saishin Igaku, 2004, vol. 59, No. 8, pp. 66-70.
English language translation of Office Action issued on Feb. 7, 2012 in corresponding Japanese Patent Application No. 2008-537953 (7 pages).

* cited by examiner

*Primary Examiner* — David Romeo
(74) *Attorney, Agent, or Firm* — Edwards Wildman Palmer LLP; Peter F. Corless; Richard B. Emmons

(57) ABSTRACT

The instant invention provides methods and compositions for the treatment and prevention of Marfan syndrome and related diseases, disorders and conditions. The invention further provides pharmaceutical compositions and kits for the treatment and prevention of Marfan syndrome and related diseases, disorders and conditions.

1 Claim, 47 Drawing Sheets

Representative of 8 treated patients

Aortic wall rescue with TGFβ neutralizing antibody (NAb)
Wild-type    C1039G/+ (placebo)    C1039G/+ (NAb)

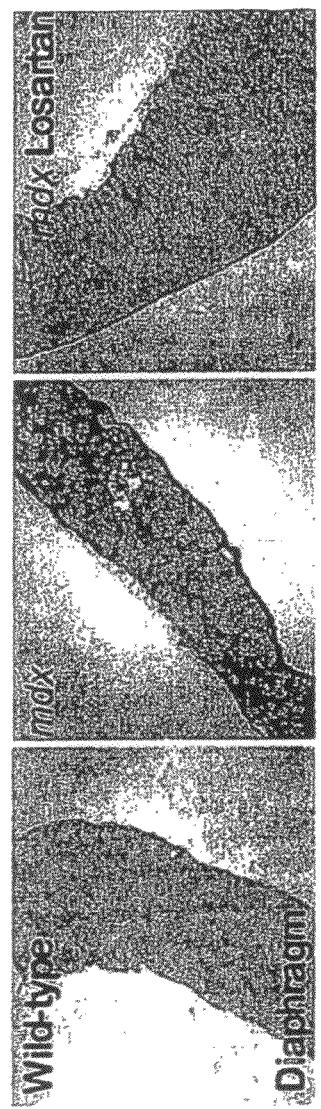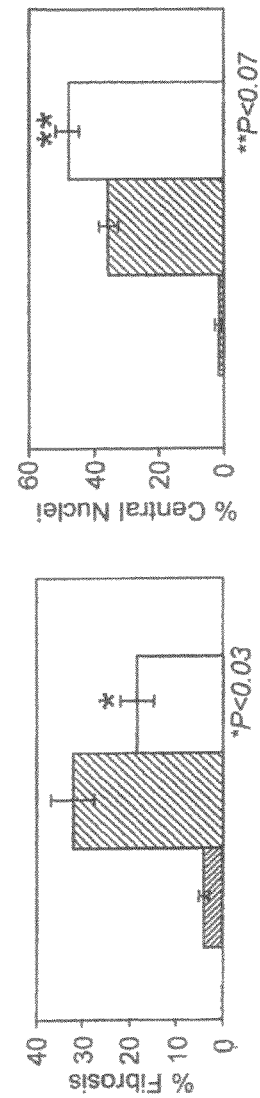
FIG. 14B-1
FIG. 14B

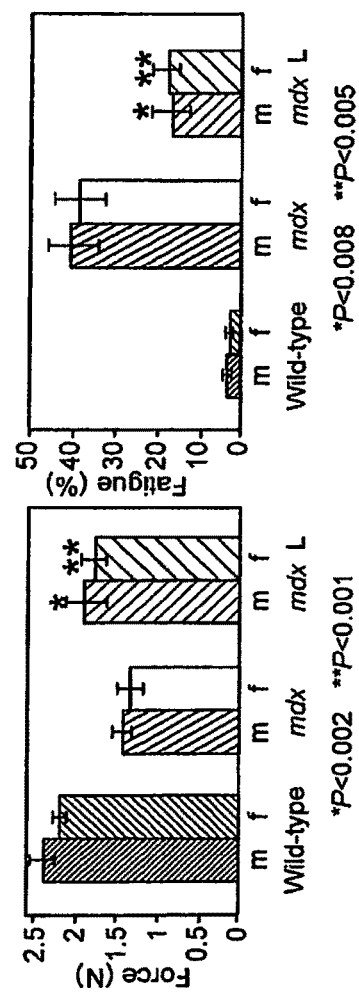

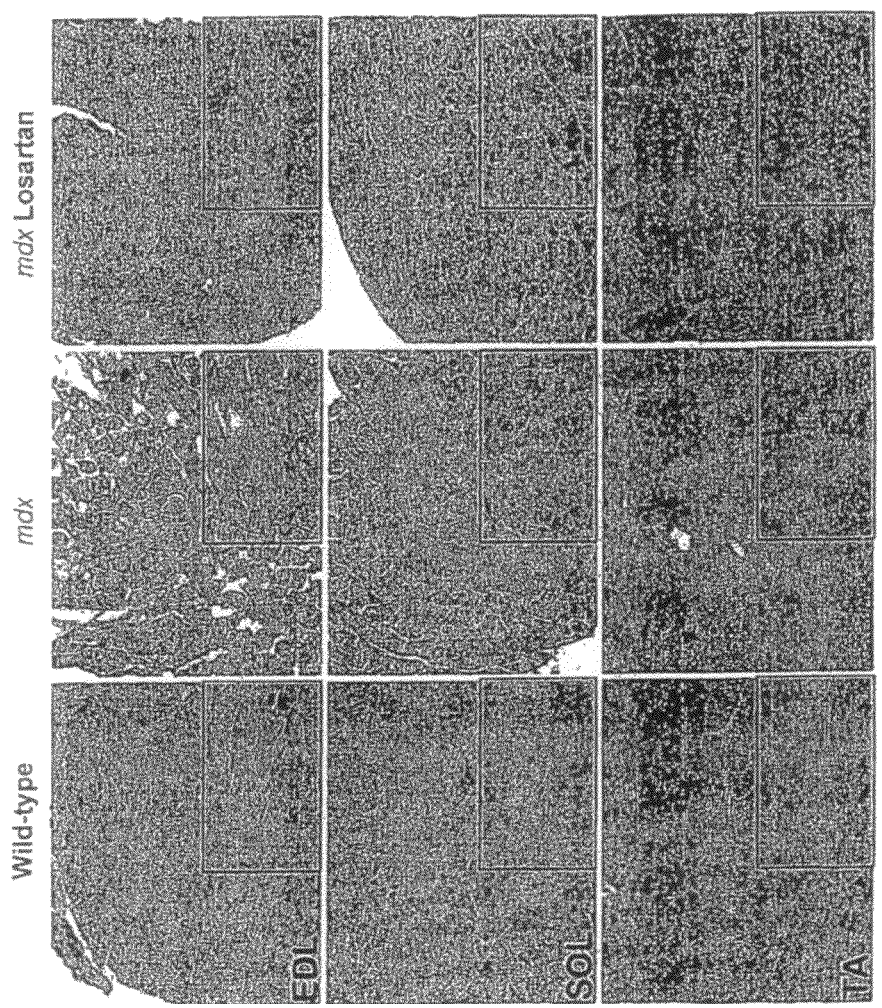

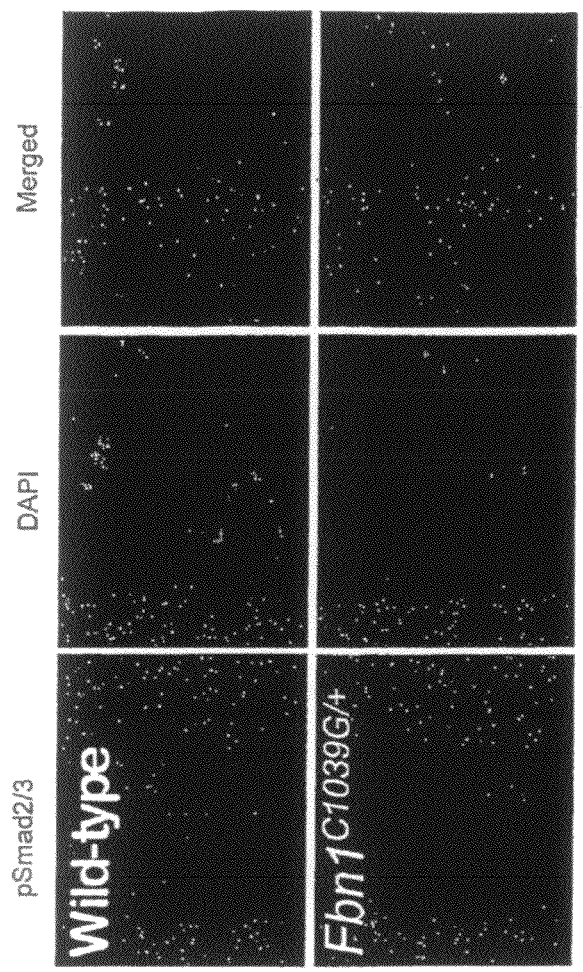

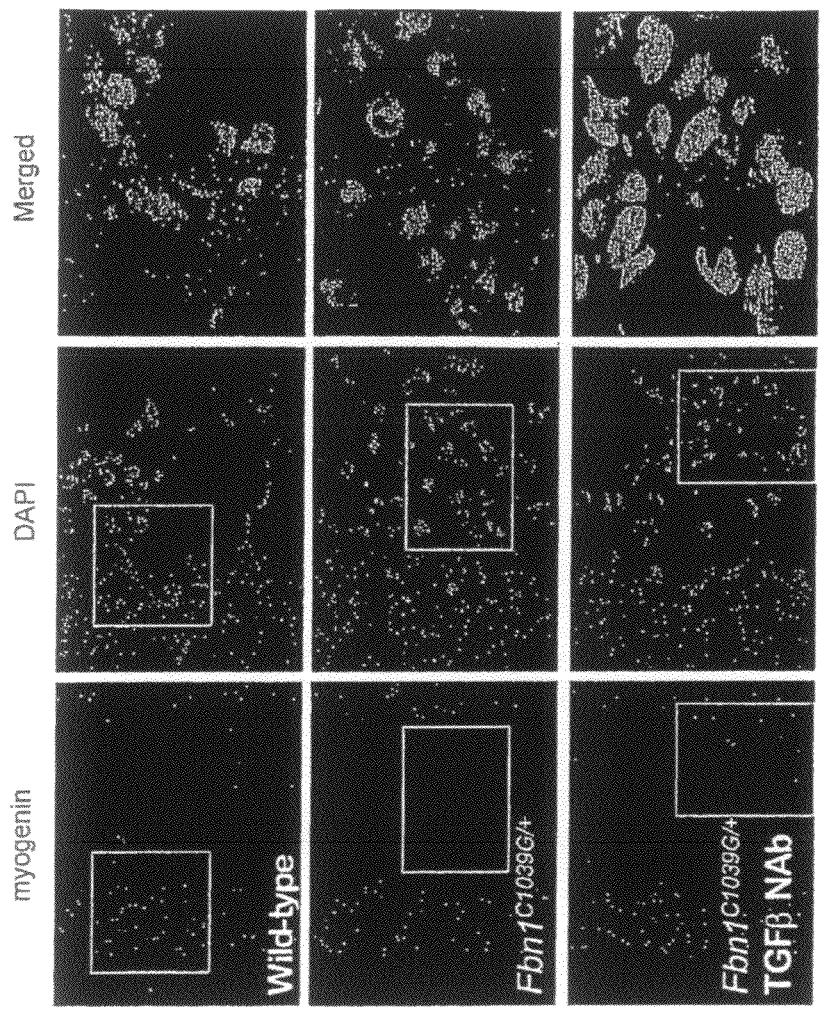

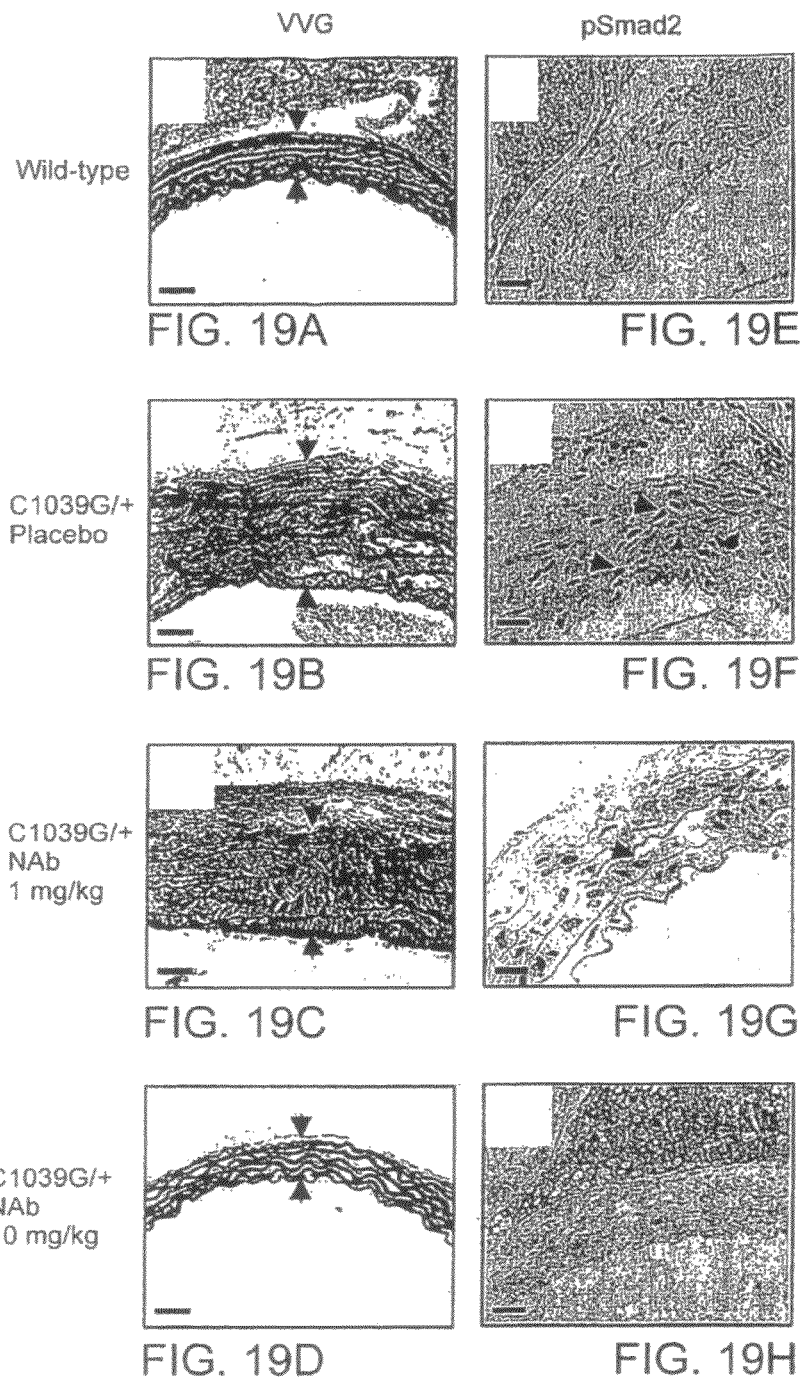

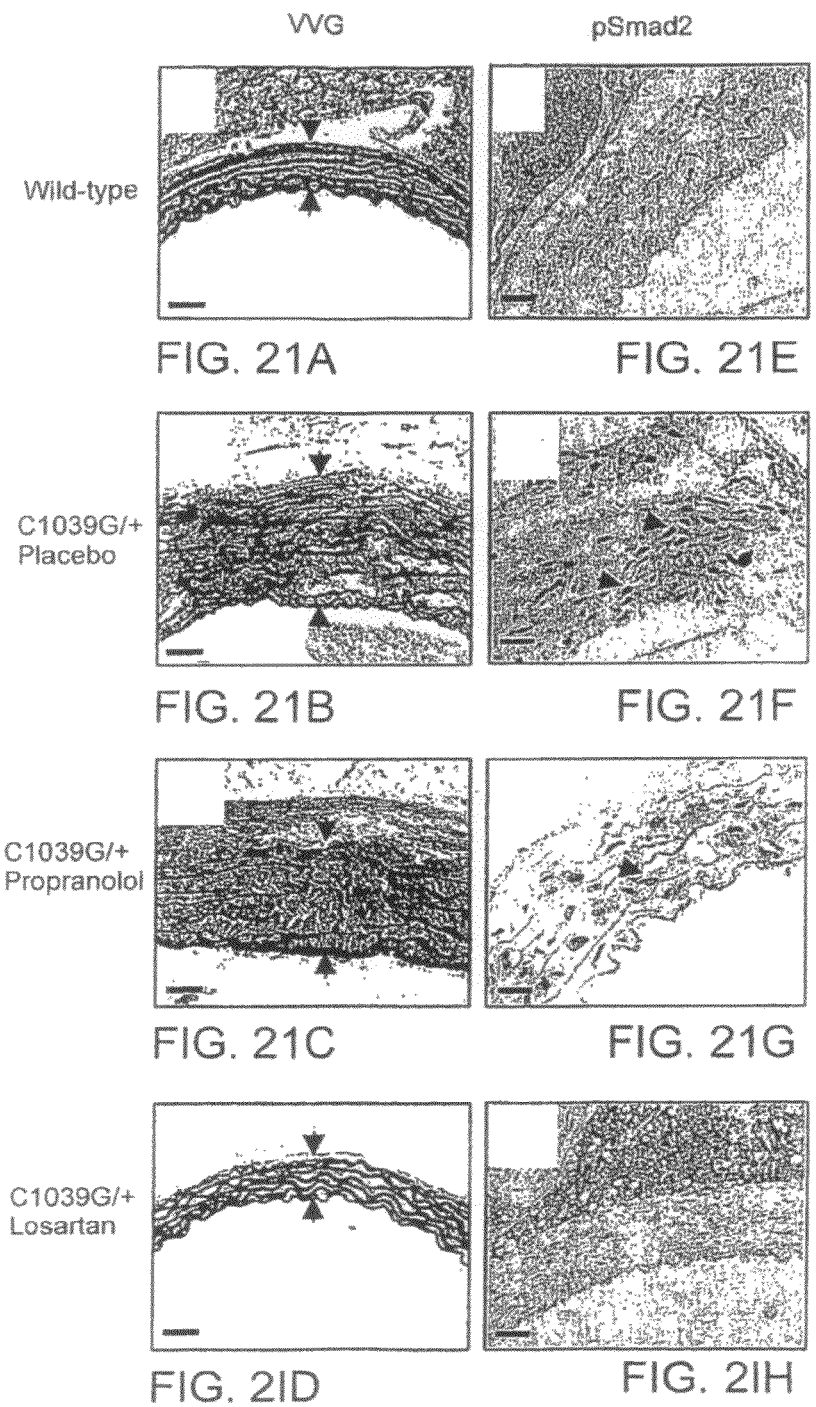

```
atgccgccctccgggctgcggctgcgctgctgctgctactcgctgtgctggctactggtg
ctgacgctggccgcccgcggcccggcgactatccacctgcaagactatcgacatggagctg
gtgaagcggaagcgcatcgaggccatcgaggccagatcctgtccaagctgcggctcgcc
agccccgagccagggggaggtgccgccgccccgcgtgcccgaggcgcgtgctcgcctg
tacaacagcaccgcgaccggtggtgccggagagtgcagaaccgagccgagcctgag
gccgactactacgccaaggaggtcaccgcgtgctaatggtgaaaccacaacgaaatc
tatgacaagttcaagcagagtacaacagcatatatatgttcttcaacacatcagagctc
cgagaagcggtacctgaacccgttgtctctcccgggcagagctgcgtctgctgaggctc
aagttaaaagtggagcagcacgtggagctggcacccagcgactcgccagagtggttatctttgatgtc
tacctcagcaaccggctgctggcagcgtgttgagccgtggagggaaattgagggcttttcgccttagc
accggagttgtgcgcagtgttgacagcaggataacacactgcaagtggacatcaacggttcact
gcccactgctcctgtgagggtgacctggccaccattcatgcatgaaccgcctttcctgcttctc
acggccgagctggagcccctgctgagcctccacgagaagaactgctgcgtgcggcagctgtacatt
atggccaaccggctgctggcagcgtgttgagccgtggagggaaattgagggcttttcgccttagc
gacaccaactattgcttcagctccacggagaagaactgctgcgtgcggcagctgtacatt
gacttccgcaaggacctcggctggaagttgatccaggacacgcagtacagcaaggtcctg
ttctgcctcggggcccctgcccctacatttggagcctggacacgcagtacagcaaggtcctg
gccctgtacaaccagcataaaccggcctggggccgcaagcccaagcccgtgctgccgaggcg
ctggagcgctgccathgtgtactgtggggccgcaagcccaaggtggagcagctgtcc
aacatgatcgtgcgctcctgcaagtgcagctga
```

SEQ ID NO:1

FIG. 23A

```
mppsglrllplllpllwllvltpgrpaaglstcktidmelvkrkrieairgqilsklrla
sppsqgevppgplpeavlalynstrdrvagesaepepepeadyyakevtrvlmvethnei
ydkfkqsthsiymffntselreavpepvllsraelrllrlklkveqhvelyqkysnnswr
ylsnrllapsdspewlsfdvtgvvrqwlsrggeiegfrlsahcscdsrdntlqvdingft
tgrrgdlatihgmnrpflllmatpleraqhlqssrhrraldtnycfsstekncc vrqlyi
dfrkdlgwkwihepkgyhanfclgpcpyiwsldtqyskvlalynqhnpgasaapccvpqa
leplpivyyvgrkpkveqlsnmivrsckcs
```

SEQIDNO:2 (mature protein underlined)

FIG. 23B

SEQUENCE LISTING

```
<160> NUMBER OF SEQ ID NOS: 2

<210> SEQ ID NO 1
<211> LENGTH: 1173
<212> TYPE: DNA
<213> ORGANISM: Homo sapiens

<400> SEQUENCE: 1
atgccgccct ccgggctgcg gctgctgctg ctgctgctac cgctgctgtg gctactggtg      60
ctgacgcctg gccggccggc cgcgggacta tccacctgca agactatcga catggagctg     120
gtgaagcgga agcgcatcga ggccatccgc ggccagatcc tgtccaagct gcggctcgcc     180
agccccccga gccaggggga ggtgccgccc ggcccgctgc ccgaggccgt gctcgccctg     240
tacaacagca cccgcgaccg ggtggccggg gagagtgcag aaccggagcc cgagcctgag     300
gccgactact acgccaagga ggtcacccgc gtgctaatgg tggaaaccca caacgaaatc     360
tatgacaagt tcaagcagag tacacacagc atatatatgt tcttcaacac atcagagctc     420
cgagaagcgg tacctgaacc cgtgttgctc tcccgggcag agctgcgtct gctgaggctc     480
aagttaaaag tggagcagca cgtggagctg taccagaaat acagcaacaa ttcctggcga     540
tacctcagca accggctgct ggcacccagc gactcgccag agtggttatc ttttgatgtc     600
accggagttg tgcggcagtg gttgagccgt ggagggaaa ttgagggctt tcgccttagc     660
gcccactgct cctgtgacag cagggataac acactgcaag tggacatcaa cgggttcact     720
accggccgcc gaggtgacct ggccaccatt catggcatga accggccttt cctgcttctc     780
atggccaccc cgctggagag ggcccagcat ctgcaaagct cccggcaccg ccgagccctg     840
gacaccaact attgcttcag ctccacggag aagaactgct gcgtgcggca gctgtacatt     900
gacttccgca aggacctcgg ctggaagtgg atccacgagc ccaagggcta ccatgccaac     960
ttctgcctcg ggccctgccc ctacatttgg agcctggaca cgcagtacag caaggtcctg    1020
gccctgtaca accagcataa cccgggcgcc tcggcggcgc cgtgctgcgt gccgcaggcg    1080
ctggagccgc tgcccathgt gtactacgtg ggccgcaagc ccaaggtgga gcagctgtcc    1140
aacatgatcg tgcgctcctg caagtgcagc tga                                 1173

<210> SEQ ID NO 2
<211> LENGTH: 390
<212> TYPE: PRT
<213> ORGANISM: Homo sapiens

<400> SEQUENCE: 2

Met Pro Pro Ser Gly Leu Arg Leu Leu Pro Leu Leu Leu Pro Leu Leu
  1               5                  10                  15
```

-continued

```
Trp Leu Leu Val Leu Thr Pro Gly Arg Pro Ala Ala Gly Leu Ser Thr
             20                  25                  30

Cys Lys Thr Ile Asp Met Glu Leu Val Lys Arg Lys Arg Ile Glu Ala
         35                  40                  45

Ile Arg Gly Gln Ile Leu Ser Lys Leu Arg Leu Ala Ser Pro Pro Ser
     50                  55                  60

Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                 85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390
```

METHODS AND COMPOSITONS FEATURING TGF-BETA ANTAGONISTS FOR THE TREATMENT OF MARFAN SYNDROME AND ASSOCIATED DISORDERS

CROSS-REFERENCE TO RELATED APPLICATIONS

This application is the 35 U.S.C. §371 national stage of PCT application PCT/US2006/041846, filed Oct. 25, 2006, which claims priority to U.S. Provisional Patent Application No. 60/729,976, filed Oct. 25, 2005. The contents of these applications are incorporated herein by reference in their entirety.

RELATED APPLICATIONS

This application claims the benefit of U.S. Provisional Application No. 60/729,976, filed Oct. 25, 2005, the entire contents of which is expressly incorporated herein by reference.

GOVERNMENT SUPPORT

The following invention was supported at least in part by NIH Grant No. ARO 41135. Accordingly, the government may have certain rights in the invention.

BACKGROUND OF THE INVENTION

The Marfan syndrome (MFS) is a systemic disorder of connective tissue with autosomal dominant inheritance and a prevalence of approximately 1 per 5,000 population (Pyeritz, R. E. & McKusick, V. A. (1979) *N Engl J Med*. 300, 772-777). The syndrome shows no racial preference and both sexes are affected equally. It has been estimated that 25% of cases occur due to spontaneous mutations. While this condition shows high penetrance, marked interfamilial clinical variability is the rule (Pyeritz, R. E. et al. (1979) *Birth Defects Orig Artic Ser*. 15, 155-178). The lack of a specific biochemical or genetic marker of disease, coupled with the variability in clinical presentation, has frustrated diagnosis of equivocal cases and has likely contributed to a significant underestimation of the prevalence of disease.

The cardinal features of this disorder involve the ocular, skeletal, and cardiovascular systems. Cardiovascular pathology, including aortic root dilatation, dissection, and rupture, pulmonary artery dilatation, myxomatous valve changes with insufficiency of the mitral and aortic valves, and progressive myocardial dysfunction, is the leading cause of mortality in the MFS. The majority of fatal events associated with untreated MFS occur in early adult life. In a prospective study of 72 patients in 1972, the average age of death was 32 years (Murdoch, J. L. et al. (1972) *N Engl J Med*. 286, 804-808).

A recent reevaluation of life expectancy in the Marfan syndrome suggested that early diagnosis and refined medical and surgical management has greatly improved this situation (Silverman, D. I. et al. (1995) *Am J Cardiol*. 75, 157-160). Nevertheless, MFS continues to be associated with significant morbidity and selected subgroups are refractory to therapy and continue to show early mortality Morse, R. P. et al. (1990) *Pediatrics*. 86, 888-895; Sisk, H. E., et al. (1983) *Am J Cardiol*. 52, 353-358). In a review of 54 patients diagnosed during infancy, Morse et al. reported that 89% had serious cardiac pathology, and that cardiac disease was progressive despite standard care (22% died during childhood, 16% before age 1 year). In the more classic form of Marfan syndrome it is estimated that greater than 90% of individuals will have a cardiovascular 'event' during their lifetime, defined as the need for prophylactic surgical repair of the aortic root or death due to aortic dissection (Gillinov, A. M., et al. (1997) *Ann Thorac Surg*. 64, 1140-1144; discussion 1144-1145; Pyeritz, R. E. (1993) *Semin Thorac Cardiovasc Surg*. 5, 11-16; Silverman, D. I., et al. (1995) *J Am Coll Cardiol*. 26, 1062-1067; Gott, V. L., et al. (1999) *N Engl J Med*. 340, 1307-1313). Ocular and skeletal morbidity is less easily quantified (Maumenee, I. H. et al. (1981) *Trans Am Opthalmol Soc*. 79, 684-733; Magid, D., et al. (1990) *AJR Am J Roentgenol*. 155, 99-104; Sponseller, P. D., et al. (1995) *J Bone Joint Surg Am*. 77, 867-876). Approximately 60% of individuals with MFS have lens dislocation, often requiring surgical aphakia for optimal management. Retinal detachment and glaucoma can cause devastating visual impairment.

Skeletal involvement is evident in nearly all people with MFS. Progressive anterior chest deformity or scoliosis can cause cardiopulmonary dysfunction and commonly require surgical correction. Joint instability can cause physical disability and predispose to premature arthritis. Lung disease most commonly manifests with spontaneous pneumothorax and has been identified in 4-11% of MFS patients (Wood, J. R., et al. (1984) *Thorax*. 39, 780-784; Hall, J. R., et al. (1984) *Ann Thorac Surg*. 37, 500-504). Pathologic findings include upper lobe bullae with or without diffuse fixed obstructive airway disease that can be progressive and has traditionally been equated with destructive emphysema (Lipton, R. A., et al. (1971) *Am Rev Respir Dis*. 104, 924; Dominguez, R., et al. (1987) *Pediatr Radiol*. 17, 365-369) The majority of patients with MFS display a marked deficiency in skeletal muscle mass and fat stores despite adequate caloric intake and no evidence for malabsorption (Behan, W. M., et al. (2003) *J Neurol Neurosurg Psychiatry*. 74, 633-638; H. H., et al. (1973) *Neurology*. 23, 1257-1268; Gross, M. L., et al. (1980) *J Neurol Sci*. 46, 105-112; Joyce, D. A., et al. (1984) *Aust N Z J Med*. 14, 495-499). Evidence for skeletal muscle myopathy, including decreased strength and tone, has been observed in a subset of affected individuals and may contribute to decreased functional performance, respiratory insufficiency, ocular misalignment, and altered development of the skeleton including kyphosis and scoliosis.

An increasing challenge is to define the "new" natural history of MFS now that many individuals are surviving their predisposition for early aortic root dissection; already appreciated aging-associated phenotypes include a predisposition for dissection of the descending thoracic and abdominal aorta. Thus, despite advances in our ability to increase the length of life for many individuals with MFS, there is ample opportunity to improve the quality of life for the majority of affected individuals.

In 1991 a traditional positional-candidate analysis culminated with the demonstration of disease producing mutations in the FBN1 gene on chromosome 15q21.1 that encodes fibrillin-1 (Dietz, H. C., et al. (1991) *Nature*. 352, 337-339). Since that time, there has been generation and characterization of multiple mouse models of Marfan syndrome. This work has truly revolutionized the understanding of the pathogenesis of disease and has lead to exciting strategies for the treatment of the multi system pathogenesis of Marfan syndrome.

Many of the features of Marfan syndrome are common in the general population and represent a tremendous public health burden. These include aortic aneurysm (1-2% of the population at large), mitral valve prolapse (~7%), emphysema (11%), scoliosis (0.5%), cataract (30%), arthritis (very common), and myopathy (many common genetic and acquired forms).

Accordingly, a need exists for methods and compositions for the treatment of Marfan syndrome and associated diseases, disorders and conditions, e.g., diseases, disorders and conditions associated with aberrant TGF-β expression.

SUMMARY OF THE INVENTION

The instant invention is based on the discovery that TFG-β antagonists effectively treat Marfan syndrome and disease and disorders related to Marfan syndrome, e.g., diseases, disorders and conditions associated with aberrant TGF-β expression.

Accordingly, in one aspect, the invention provides methods of treating a subject having or at risk of developing a disease or disorder characterized by aberrant TGFβ expression or activity comprising, administering to the subject an effective amount of an agent that modulates the activity or expression of TGFβ, thereby treating the subject.

In one embodiment, the disease or disorder is Marfan syndrome or a clinical condition associated with Marfan syndrome. In a related embodiment, the disease or disorder is an aneurysm, an aortic aneurysm, valve disease, emphysema, myopathy, scoliosis, or eye disease. In a specific embodiment, the eye disease is selected from the group consisting of cataracts, myopia, glaucoma, and retinal detachment. In a related embodiment, the disease or disorder is a disease or disorder that related to muscle growth, maintenance, or regeneration, e.g., muscular dystrophy. In a specific embodiment the disease or disorder is Duchenne muscular dystrophy.

In another embodiment, the disease or disorder is a lung disease or disorder, e.g., emphysema, pneumothorax, and COPD.

In another embodiment, the disease or disorder is arthritis.

In one embodiment, the agent is a TGFβ antagonist, e.g., a small molecule, a nucleic acid, a peptide, an antibody, a scFV, or a Fab fragment. In a specific embodiment, the antibody is a neutralizing antibody. In another embodiment, the agent is a siRNA or shRNA specific for TGFβ or regulators of the TGFβ signaling pathway. In a specific embodiment, the siRNA or shRNA is specific for the nucleic acid molecule set forth as SEQ ID NO:1.

In one embodiment, the agent is an agent that binds to the angiotensin receptor, e.g., angiotensin II type 1 receptor (AT1). In a specific embodiment, the agent is a angiotensin type 1 receptor antagonist such as 2-butyl-4-chloro-1-[p-(o-1H-tetrazol-5-ylphenyl)benzyl]imidazole-5-methanol monopotassium salt (losartan potassium).

In one embodiment, the invention provides methods for treating a subject having Marfan syndrome or a Marfan-associated condition by administering to the subject an effective amount of an agent that modulates the activity or expression of TGFβ, thereby treating the subject.

In one embodiment, the agent is a TGFβ antagonist, e.g., a small molecule, a nucleic acid, a peptide, an antibody, a scFV, or a Fab fragment. In a specific embodiment, the antibody is a neutralizing antibody. In another embodiment, the agent is a siRNA or shRNA specific for TGFβ or regulators of the TGFβ signaling pathway. In a specific embodiment, the siRNA or shRNA is specific for the nucleic acid molecule set forth as SEQ ID NO:1.

In one embodiment, the agent is an agent that binds to the angiotensin receptor, e.g., angiotensin II type 1 receptor (AT1). In a specific embodiment, the agent is a angiotensin type 1 receptor antagonist such as 2-butyl-4-chloro-1-[p-(o-1H-tetrazol-5-ylphenyl)benzyl]imidazole-5-methanol monopotassium salt (losartan potassium).

In another aspect, the invention provides methods of treating a subject having Duchenne muscular dystrophy by administering to the subject an effective amount of an agent that modulates the activity or expression of TGFβ, thereby treating the subject.

In one embodiment, the agent is a TGFβ antagonist, e.g., a small molecule, a nucleic acid, a peptide, an antibody, a scFV, or a Fab fragment. In a specific embodiment, the antibody is a neutralizing antibody. In another embodiment, the agent is a siRNA or shRNA specific for TGFβ or regulators of the TGFβ signaling pathway. In a specific embodiment, the siRNA or shRNA is specific for the nucleic acid molecule set forth as SEQ ID NO:1.

In one embodiment, the agent is an agent that binds to the angiotensin receptor, e.g., angiotensin II type 1 receptor (AT1). In a specific embodiment, the agent is a angiotensin type 1 receptor antagonist such as 2-butyl-4-chloro-1-[p-(o-1H-tetrazol-5-ylphenyl)benzyl]imidazole-5-methanol monopotassium salt (losartan potassium).

In another aspect, the invention provides a method of treating a subject having arthritis by administering to the subject an effective amount of an agent that modulates the activity or expression of TGFβ, thereby treating the subject.

In one embodiment, the agent is a TGFβ, antagonist, e.g., a small molecule, a nucleic acid, a peptide, an antibody, a scFV, or a Fab fragment. In a specific embodiment, the antibody is a neutralizing antibody. In another embodiment, the agent is a siRNA or shRNA specific for TGFβ or regulators of the TGFβ signaling pathway. In a specific embodiment, the siRNA or shRNA is specific for the nucleic acid molecule set forth as SEQ ID NO:1.

In one embodiment, the agent is an agent that binds to the angiotensin receptor, e.g., angiotensin II type 1 receptor (AT1). In a specific embodiment, the agent is a angiotensin type 1 receptor antagonist such as 2-butyl-4-chloro-1-[p-(o-1H-tetrazol-5-ylphenyl)benzyl]imidazole-5-methanol monopotassium salt (losartan potassium).

In another aspect, the invention provides pharmaceutical compositions for the treatment of a disease or disorder characterized by aberrant TGFβ expression, wherein the pharmaceutical composition comprises an agent that modulates the activity or expression of TGFβ.

In one embodiment, the disease or disorder is Marfan syndrome or a clinical condition associated with Marfan syndrome. In a related embodiment, the disease or disorder is an aneurysm, an aortic aneurysm, valve disease, emphysema, myopathy, scoliosis, or eye disease. In a specific embodiment, the eye disease is selected from the group consisting of cataracts, myopia, glaucoma, and retinal detachment. In a related embodiment, the disease or disorder is a disease or disorder that related to muscle growth, maintenance, or regeneration, e.g., muscular dystrophy. In a specific embodiment the disease or disorder is Duchenne muscular dystrophy.

In another embodiment, the disease or disorder is a lung disease or disorder, e.g., emphysema, pneumothorax, and COPD.

In another embodiment, the disease or disorder is arthritis.

In another embodiment, the pharmaceutical composition is a TGFβ antagonist.

In one embodiment, the agent is a TGFβ antagonist, e.g., a small molecule, a nucleic acid, a peptide, an antibody, a scFV, or a Fab fragment. In a specific embodiment, the antibody is a neutralizing antibody. In another embodiment, the agent is a siRNA or shRNA specific for TGFβ or regulators of the TGFβ signaling pathway. In a specific embodiment, the siRNA or shRNA is specific for the nucleic acid molecule set forth as SEQ ID NO:1.

In one embodiment, the agent is an agent that binds to the angiotensin receptor, e.g., angiotensin II type 1 receptor (AT1). In a specific embodiment, the agent is a angiotensin type 1 receptor antagonist such as 2-butyl-4-chloro-1-[p-(o-1H-tetrazol-5-ylphenyl)benzyl]imidazole-5-methanol monopotassium salt (losartan potassium).

In another aspect, the invention provides kits for the treatment of a disease or disorder characterized by aberrant TGFβ expression, wherein the pharmaceutical composition comprises an agent that modulates the activity or expression of TGFβ and instructions for use.

In one embodiment, the disease or disorder is Marfan syndrome or a clinical condition associated with Marfan syndrome. In a related embodiment, the disease or disorder is an aneurysm, an aortic aneurysm, valve disease, emphysema, myopathy, scoliosis, or eye disease. In a specific embodiment, the eye disease is selected from the group consisting of cataracts, myopia, glaucoma, and retinal detachment. In a related embodiment, the disease or disorder is a disease or disorder that related to muscle growth, maintenance, or regeneration, e.g., muscular dystrophy. In a specific embodiment the disease or disorder is Duchenne muscular dystrophy.

In another embodiment, the disease or disorder is a lung disease or disorder, e.g., emphysema, pneumothorax, and COPD.

In another embodiment, the disease or disorder is arthritis.

In another embodiment, the pharmaceutical composition is a TGFβ antagonist.

In one embodiment, the agent is a TGFβ antagonist, e.g., a small molecule, a nucleic acid, a peptide, an antibody, a scFV, or a Fab fragment. In a specific embodiment, the antibody is a neutralizing antibody. In another embodiment, the agent is a siRNA or shRNA specific for TGFβ or regulators of the TGFβ signaling pathway. In a specific embodiment, the siRNA or shRNA is specific for the nucleic acid molecule set forth as SEQ ID NO:1.

In one embodiment, the agent is an agent that binds to the angiotensin receptor, e.g., angiotensin II type 1 receptor (AT1). In a specific embodiment, the agent is a angiotensin type 1 receptor antagonist such as 2-butyl-4-chloro-1-[p-(o-1H-tetrazol-5-ylphenyl)benzyl]imidazole-5-methanol monopotassium salt (losartan potassium).

DESCRIPTION OF THE DRAWINGS

FIG. 6B). A normal quotient of SCs (marked by C-met staining), but a dramatic reduction in proliferating SCs (marked by M-cadherin staining; FIG. 6C). The response was fully normalized after injection of TGFβNAb, including restored proliferation in response to injury, decreased pSmad2 and periostin expression, and normalization of muscle architecture with centrally-nucleated muscle fibers demonstrating direct evidence of successful regeneration (FIG. 6B,C). Mice receiving chronic administration of NAb showed normal steady-state muscle architecture (FIG. 6D).

FIG. 9A). Losartan also normalized steady-state architecture of skeletal muscle and allowed normal initiation of muscle regeneration at both 4 and 18 days after induced injury with cardiotoxin (FIG. 9B, C).

FIGS. 14A-C depict immunofluorescent analysis of target proteins downstream of the angiotensin II type 1 receptor. Skeletal muscle of wild-type diaphragm exhibits only faint expression of thrombospondin-1 (TSP). Increased sarcolemmal expression is detected in diaphragm of untreated mdx mice. In contrast, losartan-treated mice show greatly reduced expression of in thrombospondin-1 (upper panel). Moreover, losartan treatment leads to diminished nuclear accumulation of pSmad2 (middle panel) and sarcolemmal expression of periostin (lower panel). The box displays nuclear enhancement of pSmad2 in connective tissue. (b) Long-term losartan treatment attenuates myopathic disease progression in 9 month-old mdx mice. The upper level displays representative diaphragmatic sections of van-Gieson staining from wild-type, mdx and losartan-treated mdx mice. Losartan treated mice show significantly less fibrosis than untreated mdx mice, Bar=150 μm. The second panel shows quantification of fibrotic areas (left) [wild-type 4%±1; mdx 32%±5; mdx Losartan 18%±4] and percentage of centrally located nuclei in the diaphragm (right) [wild-type 2%±0.5; mdx 35%±5; mdx Losartan 48%±6]. Van-Gieson staining of gastrocnemius muscles from wild-type, mdx and losartan-treated mdx mice are shown in the third panel (Bar=100 μm). Corresponding quantitative analysis of fibrosis [wild-type 4%±2; mdx 75%±6.4; mdx Losartan 89%±5.8] and centrally located nuclei are displayed in the lower panel [wild-type 2%±0.5; mdx 25%±5; mdx Losartan 36%±+6]. (c) Functional analysis of losartan-treated mdx mice. After 6 months, mdx mice treated with losartan demonstrate improved hindlimb grip strength (measured as peak force in N, upper graph, m=male, f=female, n=6 mice each group, left side, upper panel) when compared to untreated mdx mice (1.89±0.23[male]/1.79±0.14[female]N versus 1.45±0.19[male]/1.39±0.14 [female] N, respectively; *$P<0.002$ and **$P<0.001$). In addition, losartan-treated mice showed significantly less muscle fatigue in response to repetitive challenge (16.2%±5[male]/17.1±4[female]% versus 39.5%±6 [male]/37.6%±6[female]; *$P<0.008$ and **$P<0.005$, right side, upper panel). Corresponding hematoxylin-and-eosin stained representative sections of extensor digitorum longus (EDL), soleus (SOL), tibialis anterior (TA) muscles of 9 month-old wild-type, mdx and losartan-treated mdx mice demonstrating significantly less morphological damage in skeletal muscle of losartan treated mdx mice.

FIGS. 16A-D depict nuclear enhancement of pSmad2/3 expression in Fbn1$^{C1039G/+}$ mice as evidenced by merged staining with the nuclear marker DAPI(a). (b) Low power images of tibialis anterior muscle 18 days after cardiotoxin injection emphasizing decreased muscle fiber size in fibrillin-1-deficient mice. (c) Decreased expression of thrombospondin-1 (TSP1) and periostin in skeletal muscle of losartan-treated fibrillin-1 deficient mice. (d) Functional benefit of losartan treatment. Long-term losartan treatment rescues functional deficits in 6 month old mice deficient for fibrillin-1 (Fbn1$^{mgR/mgR}$). Data represent forelimb grip strength in N and fatigue expressed as percentage. At 6 months of age, Fbn1$^{mgR/mgR}$ mice demonstrated a significant decrease in muscle strength when compared to age-matched wild-type mice (1.39 Newton [N]±0.16 vs. 1.93N±0.12, respectively). In addition, Fbn1$^{mgR/mgR}$ mice demonstrate excessive muscle fatigue in response to repetitive challenge (28%±2.5 vs. 3%±0.8, respectively). After 5 months of losartan treatment, Fbn1$^{mgR/mgR}$ mice showed improved forelimb grip strength (1.87N±0.15) and reduced fatigue (9%±1.8) when compared to untreated Fbn1$^{mgR/mgR}$ littermates. The mouse model of Marfan syndrome used for functional studies is homozygous for a hypomorphic Fbn1 allele (Fbn1$^{mgR/mgR}$)[47] that expresses normal fibrillin-1 at a level that approximates 15% of normal. This mouse line recapitulates the aortic, lung and valve pathology seen in C1039G mice, albeit at an accelerated rate 21, 49, 50. The same is true for skeletal muscle, enhancing the potential to observe and restore a functional deficit.

FIGS. 17A-C demonstrate that there is no difference in the number of c-met positive muscle fibers, a marker for quiescent satellite cells, in wild-type and Fbn1$^{C1039G/+}$ mice. (b) Perturbed satellite cell function in Fbn1$^{C1039G/+}$ mice. At 48 and 72 hours after cardiotoxin injection, Fbn1$^{C1039G/+}$ mice exhibit significantly less M-cadherin- and myogenin-positive nuclei, as compared to wild-type and TGFO NAb treated Fbn1$^{C1039G/+}$ mice. Merged image shows co-localization of M-cadherin with DAPI-stained nuclei (purple); laminin yl staining demarcates the basement membrane (upper panel). (c) Myogenin positive cells co-localize with the nuclear marker DAPI.

FIGS. 19 A-I depict postnatal treatment with TGF-β NAb. Characterization of the ascending aorta in untreated wild-type mice [(FIG. 19A) and (FIG. 19E)] and Fbn1$^{C1039G/+}$ mice treated with placebo [(FIG. 19B) and (FIG. 19F)], 1 mg/kg TGF-β NAb [(FIG. 19C) and (FIG. 19G)], and 10 mg/kg TGF-β NAb [(FIG. 19D) and (FIG. 19H)]. In (FIG. 19A) to (FIG. 19D), Verhoeff's-van Gieson (VVG) stain reveals diffuse disruption of elastic fiber architecture and thickening of the aortic media (delineated by arrows) in placebo-treated Fbn1$^{C1039G/+}$ mice (FIG. 19B) relative to the normal elastic fiber architecture observed in wild-type mice (FIG. 19A). Improvement in both parameters is seen in NAb-treated Fbn1$^{C1039G/+}$ mice [(FIG. 19C) and (FIG. 19D)]. Scale bars, 40 μm. In (FIG. 19E) to (FIG. 19H), immunohistochemistry (1H) reveals nuclear pSmad2, a marker for TGF-β signaling (arrows indicate representative positive nuclei). Increased pSmad2 is observed in the placebo-treated Fbn1$^{C1039G/+}$ mice (FIG. 19F) relative to wild-type mice (FIG. 19E). Normalized pSmad2 staining is observed in the NAb-treated Fbn1$^{C1039G/+}$ mice [(FIG. 19G) and (FIG. 19H)]. Scale bars, 50 μm.

FIGS. A-F depict prenatal treatment with losartan and propranolol.

FIGS. 21A-K depict postnatal treatment with losartan and propranolol. VVG staining [(A) to (D)] and pSmad2 immunostaining [(E) to (H)] of aortic wall. Elastic lamellae are intact and aortic media is of normal thickness in the wild-type (A) and losartan-treated Fbn1$^{C1039G/+}$ mice (D). Placebo- and propranolol-treated Fbn1$^{C1039G/+}$ mice [(B) and (C)] have diffuse fragmentation of elastic fibers and thickening of the aortic media (arrows). Scale bars, 50 μm. Nuclear pSmad2 staining is decreased in the aortic media of wild-type (E) and losartan-treated Fbn1$^{C1039G/+}$ mice (H). Marked increase in nuclear staining for pSmad2 (representative positive cells denoted by arrowheads) is seen in the Fbn1$^{C1039G/+}$ mice treated with placebo (F) and propranolol (G). Scale bars, 40 μm. (I) Average aortic root growth (±SD) during the 6 months of treatment. Note that aortic root growth in Fbn1$^{C1039G/+}$ mice treated with propranolol is less than that with placebo, yet remains greater than that seen in wild-type mice. Losartan treatment normalizes growth rate. *P<0.0001, P<0.001, *P<0.02, †P=0.55. (J) Average aortic wall thickness (±SD). Aortic wall thickness in losartan-treated Fbn1$^{C1039G/+}$ mice is reduced relative to placebo- and propranolol-treated mice and is indistinguishable from that seen in wild-type mice. *P<0.002, P<0.0001, *P<0.05, †P=0.67, ††P=0.17. (K) Average aortic wall architecture (±SD). Note full normalization achieved with losartan treatment. *P<0.002, P<0.0001, *P<0.05, †P=0.20, ††P=0.47.

FIGS. 23A-B set forth the nucleic acid sequence (SEQ ID NO:1) and polypeptide sequence (SEQ ID NO:2) of TGF-β, respectively.

DETAILED DESCRIPTION OF THE INVENTION

Figure 1A:
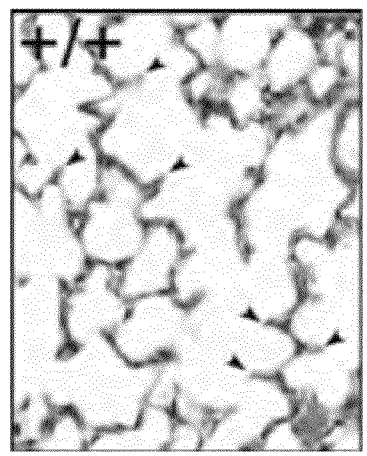
FIGS. 1A-B demonstrate that fibrillin-1-deficient mice display primary failure of distal airspace septation, histologic examination of fibrillin-1-deficient postnatal day 9 (D9) lungs (after controlled inflation) revealed marked widening of the distal airspace. Morphometric analysis demonstrated distal airspace enlargement in both heterozygous and homozygous mutant lungs back to day 1. Histologic analysis did not show any evidence of destruction or inflammation, but rather a paucity of primordial alveolar septae (see arrow heads).
Figure 1B:
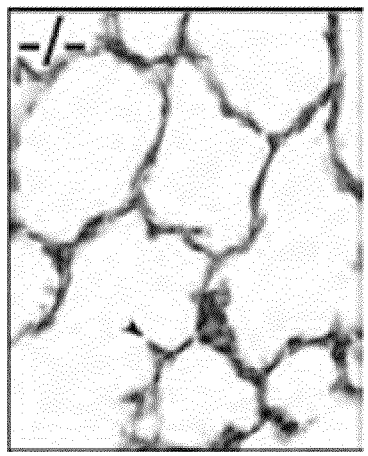

The instant invention is based on the discovery that TFG-β antagonists effectively treat Marfan syndrome and disease and disorders related to Marfan syndrome. Accordingly, the invention provides methods and compositions for treating Marfan syndrome and related diseases and disorders.

Agents of the Invention

The invention provides agents to modulate the expression or activity of TGF-β or proteins and/or nucleic that control the activity or expression of TGF-β. In one embodiment, the agent is a TGF-β antagonist. In a particular embodiment, the agent is a angiotensin receptor blockers (ARBs), e.g., losartan (Cozaar), irbesartan (Avapro), valsartan (Diovan), or candesartan (Atacand).

As used herein, a "TGF-β antagonist" is any molecule which is able to decrease the amount or activity of TGF-β, either within a cell or within a physiological system. Exemplary antagonists include compounds, molecules, or agents that inhibit a biological activity. Examples of antagonist molecules include, but are not limited to, peptides, small molecules, antibodies, antisense nucleic acids, siRNA nucleic acids, aptamers, and other binding agents. The ability to decrease the amount or activity of TGF-β is not limited by any mechanism. For example, a TGF-β antagonist may be a molecule which inhibits expression of TGF-β at the level of transcription, translation, processing, or transport; it may affect the stability of TGF-β or conversion of the precursor molecule to the active, mature form; it may affect the ability of TGF-β to bind to one or more of its receptors (Type I, Type II or Type III); or it may interfere with TGF-β signaling.

A variety of TGF-β antagonists and methods for their production are well known in the art and many more are currently under development. The specific TGF-β antagonist employed is not a limiting feature, as any effective TGF-β antagonist may be useful in the methods of this invention. One particular TGF-β antagonist that is useful in the methods of the invention is 2-butyl-4-chloro-1-[p-(o-1H-tetrazol-5-ylphenyl)benzyl]imidazole-5-methanol monopotassium salt (losartan potassium). Further examples of such antagonists include monoclonal and polyclonal antibodies directed against one or more isoforms of TGF-β (U.S. Pat. No. 5,571,714 and PCT patent application WO 97/13844), TGF-β receptors, fragments thereof, derivatives thereof and antibodies directed against TGF-β receptors (U.S. Pat. Nos. 5,693,607, 6,008, 011, 6,001,969 and 6,010,872 and PCT patent applications WO 92/00330, WO 93/09228, WO 95/10610 and WO 98/48024); latency associated peptide (WO 91/08291), large latent TGF-β (WO 94/09812), fetuin (U.S. Pat. No. 5,821, 227), decorin and other proteoglycans such as biglycan, fibromodulin, lumican and endoglin (U.S. Pat. Nos. 5,583, 103, 5,654,270, 5,705,609, 5,726,149, 5,824,655 5,830,847, 6,015,693 and PCT patent applications WO 91/04748, WO 91/10727, WO 93/09800 and WO 94/10187).

Further examples of such antagonists include somatostatin (PCT patent application WO 98/08529), mannose-6-phosphate or mannose-1-phosphate (U.S. Pat. No. 5,520,926), prolactin (PCT patent application WO 97/40848), insulin-like growth factor II (PCT patent application WO 98/17304), IP-10 (PCT patent application WO97/00691), arg-gly-asp containing peptides (U.S. Pat. No. 5,958,411 and PCT patent application WO 93/10808 and), extracts of plants, fungi and bacteria (European patent application 813875, Japanese patent application 8119984 and U.S. Pat. No. 5,693,610), antisense oligonucleotides (U.S. Pat. Nos. 5,683,988, 5,772, 995, 5,821,234 and 5,869,462 and PCT patent application WO 94/25588), and a host of other proteins involved in TGF-β signaling, including SMADs and MADs (European patent application EP 874046, PCT patent applications WO 97/31020, WO 97/38729, WO 98/03663, WO 98/07735, WO 98/07849, WO 98/45467, WO 98/53068, WO 98/55512, WO 98/56913, WO 98/53830, and WO 99/50296, and U.S. Pat. Nos. 5,834,248, 5,807,708 and 5,948,639) and Ski and Sno (G. Vogel, Science, 286:665 (1999) and Stroschein et al., Science, 286:771-74 (1999)) and fragments and derivatives of any of the above molecules that retain the ability to inhibit the activity of TGF-β.

TGF-β receptors and TGF-β-binding fragments of TGF-β receptors, especially soluble fragments are useful TGF-β antagonists in the methods of the present invention. TGF-β receptors and the nucleic acids encoding them are well known in the art. The nucleic acid sequence encoding TGF-β type 1 receptor is disclosed in GENBank accession number L15436 and in U.S. Pat. No. 5,538,892 of Donahoe et al. The nucleic acid sequence of TGF-β type 2 receptor is publicly available under GENBank accession numbers AW236001; AI35790; AI279872; AI074706; and AA808255. The nucleic acid sequence of TGF-β type 3 receptor is also publicly available under GENBank accession numbers NM 003243; AI887852; AI817295; and AI681599.

Agents useful in the methods of the invention can be nucleic acid molecules, e.g., antisense, ribozyme, or RNA interference technology, e.g., siRNA molecules corresponding to a portion of the TGF-β nucleotide sequence.

Antisense polynucleotides may act by directly blocking translation by hybridizing to mRNA transcripts or degrading such transcripts of a gene. The antisense molecule may be recombinantly made using at least one functional portion of a gene in the antisense orientation as a region downstream of a promoter in an expression vector. Chemically modified bases or linkages may be used to stabilize the antisense polynucleotide by reducing degradation or increasing half-life in the body (e.g., methyl phosphonates, phosphorothioate, peptide nucleic acids). The sequence of the antisense molecule may be complementary to the translation initiation site (e.g., between −10 and +10 of the target's nucleotide sequence).

Ribozymes catalyze specific cleavage of an RNA transcript or genome. The mechanism of action involves sequence-specific hybridization to complementary cellular or viral RNA, followed by endonucleolytic cleavage. Inhibition may or may not be dependent on ribonuclease H activity. The ribozyme includes one or more sequences complementary to the target RNA as well as catalytic sequences responsible for RNA cleavage (e.g., hammerhead, hairpin, axehead motifs). For example, potential ribozyme cleavage sites within a subject RNA are initially identified by scanning the subject RNA for ribozyme cleavage sites which include the following trinucleotide sequences: GUA, GUU and GUC. Once identified, an oligonucleotide of between about 15 and about 20 ribonucleotides corresponding to the region of the subject RNA containing the cleavage site can be evaluated for predicted structural features, such as secondary structure, that can render candidate oligonucleotide sequences unsuitable. The suitability of candidate sequences can then be evaluated by their ability to hybridize and cleave target RNA. The ribozyme may be recombinantly produced or chemically synthesized.

siRNA refers to double-stranded RNA of at least 20-25 basepairs which mediates RNA interference (RNAi). Duplex siRNA corresponding to a target RNA may be formed by separate transcription of the strands, coupled transcription from a pair of promoters with opposing polarities, or annealing of a single RNA strand having an at least partially self-complementary sequence. Alternatively, duplexed oligoribonucleotides of at least about 21 to about 23 basepairs may be chemically synthesized (e.g., a duplex of 21 ribonucleotides with 3' overhangs of two ribonucleotides) with some substitutions by modified bases being tolerated. Mismatches in the center of the siRNA sequence, however, abolishes interference. The region targeted by RNA interference should be transcribed, preferably as a coding region of the gene. Interference appears to be dependent on cellular factors (e.g., ribonuclease III) that cleave target RNA at sites 21 to 23 bases apart; the position of the cleavage site appears to be defined by the 5' end of the guide siRNA rather than its 3' end. Priming by a small amount of siRNA may trigger interference after amplification by an RNA-dependent RNA polymerase.

In one embodiment, the TGF-β antagonist is an antibody that blocks TGF-β binding to its receptor, or fragments thereof such as F(ab)$_2$ fragments, Fv fragments, single chain antibodies and other forms of "antibodies" that retain the ability to bind to TGF-β. In one aspect of the invention antibodies are provided. The term "antibody" as used herein refers to immunoglobulin molecules and immunologically active portions of immunoglobulin molecules, i.e., molecules that contain an antigen binding site which specifically binds (immunoreacts with) an antigen, such as TGF-β. Examples of immunologically active portions of immunoglobulin molecules include F(ab) and F(ab').sub.2 fragments which can be generated by treating the antibody with an enzyme such as pepsin. The invention provides polyclonal and monoclonal antibodies that bind TGF-β. The term "monoclonal antibody" or "monoclonal antibody composition", as used herein, refers to a population of antibody molecules that contain only one species of an antigen binding site capable of immunoreacting with a particular epitope of TGF-β. A monoclonal antibody composition thus typically displays a single binding affinity for a particular TGF-β protein with which it immunoreacts.

Polyclonal anti-TGF-β antibodies can be prepared as described above by immunizing a suitable subject with an TGF-β immunogen. The anti-TGF-β antibody titer in the immunized subject can be monitored over time by standard techniques, such as with an enzyme linked immunosorbent assay (ELISA) using immobilized TGF-β. If desired, the antibody molecules directed against TGF-β can be isolated from the mammal (e.g., from the blood) and further purified by well known techniques, such as protein A chromatography to obtain the IgG fraction. At an appropriate time after immunization, e.g., when the anti-TGF-β antibody titers are highest, antibody-producing cells can be obtained from the subject and used to prepare monoclonal antibodies by standard techniques, such as the hybridoma technique originally described by Kohler and Milstein (1975) Nature 256:495-497 (see also Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med., 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with an TGF-β immunogen as described above, and the culture supernatants of the resulting hybridoma cells are screened to identify a hybridoma producing a monoclonal antibody that binds TGF-β.

Any of the many well known protocols used for fusing lymphocytes and immortalized cell lines can be applied for the purpose of generating an anti-TGF-β monoclonal antibody (see, e.g., Galfre, G. et al. (1977) Nature 266:55052; Gefter et al. Somatic Cell Genet., supra; Lerner (1981) supra; Kenneth, Monoclonal Antibodies, supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag-4-1, P3-x63-Ag8.653 or Sp2/O-Ag14 myeloma lines. These myeloma lines are available from. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind TGF-β, e.g., using a standard ELISA assay.

Alternative to preparing monoclonal antibody-secreting hybridomas, a monoclonal anti-TGF-β antibody can be identified and isolated by screening a recombinant combinatorial immunoglobulin library (e.g., an antibody phage display library) with TGF-β to thereby isolate immunoglobulin library members that bind TGF-β. Kits for generating and screening phage display libraries are commercially available (e.g., the Pharmacia Recombinant Phage Antibody System, Catalog No. 27-9400-01; and the Stratagene SURFZAP™ Phage Display Kit, Catalog No. 240612). Additionally, examples of methods and reagents particularly amenable for use in generating and screening antibody display library can be found in, for example, Ladner et al. U.S. Pat. No. 5,223, 409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) Science 246: 1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc. Acid Res. 19:4133-4137; Barbas et al., (1991) Proc. Natl. Acad. Sci. USA 88:7978-7982; and McCafferty et al. (1990) Nature 348:552-554.

Additionally, recombinant anti-TGF-β antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

An anti-TGF-β antibody (e.g., monoclonal antibody) can be used to isolate TGF-β by standard techniques, such as affinity chromatography or immunoprecipitation. An anti-TGF-β antibody can facilitate the purification of natural TGF-β from cells and of recombinantly produced TGF-β expressed in host cells. Moreover, an anti-TGF-β antibody can be used to detect TGF-β protein (e.g., in a cellular lysate or cell supernatant) in order to evaluate the abundance and pattern of expression of the TGF-β protein. Anti-TGF-β antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidintbiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $a^3H$.

In one embodiment, the antibody of the invention is a TGF-β neutralizing antibody.

Pharmaceutical Compositions of the Invention

The agents described herein can be formulated into pharmaceutical compositions for the treatment of the diseases, disorders and conditions disclosed herein. The language "pharmaceutical composition" includes preparations suitable for administration to mammals, e.g., humans. When the compounds used in the methods of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (13HT), lecithin, propyl gallate, .alpha.-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue, The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a disease, disorder or condition set forth herein.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

In exemplary embodiments of the invention, the pharmaceutical composition is losartan (marketed as Cozaar by Merck).

Methods of Treatment

As used herein, the term "Marfan syndrome or associated diseases, disorders and conditions" is intended to mean Marfan syndrome or any one of the multitude of diseases disorders or conditions that is caused or associated with the biochemical events that cause Marfan syndrome, e.g., the abbarent expression or activity or TGFβ. Exemplary conditions include aneurysm, an aortic aneurysm, valve disease, emphysema, myopathy, scoliosis, or eye disease. Exemplary eye diseases include cataracts, myopia, glaucoma, and retinal detachment. Moreover, Marfan syndrome or associated diseases, disorders and conditions include diseases and disorders that related to muscle growth, maintenance, or regeneration, e.g., muscular dystrophies such as Duchenne muscular dystrophy. Further, the disease or disorder can be a lung disease or disorder, e.g., emphysema, pneumothorax, and COPD.

The term "treated," "treating" or "treatment" includes the diminishment or alleviation of at least one symptom associated or caused by Marfan syndrome, or an associated disease, disorder or condition. For example, treatment can be diminishment of one or several symptoms of a disease or disorder or complete eradication of the disease or disorder, e.g., Marfan syndrome.

The term "subject" is intended to include organisms, e.g., prokaryotes and eukaryotes, which are capable of suffering from or afflicted with Marfan syndrome, or a disease, disorder or condition related thereto. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a Marfan syndrome, or a disease, disorder or condition related thereto.

The agents and pharmaceutical compositions of the invention can be administered to a subject to treat or prevent diseases, disorders and conditions associated with aberrant TGF-β activity or expression. In one embodiment the agents and pharmaceutical compositions are used to treat or prevent Marfan syndrome or diseases or disorders associated with Marfan syndrome.

In one embodiment, the agents or pharmaceutical compositions are administered in an effective amount using a dosing schedule determined by a medical provider to treat or prevent a disease or disorder set forth herein. The agents or pharmaceutical compositions can be administered in a variety or methods described herein and known to one of skill in the art.

In one aspect, the invention provides a method for preventing in a subject, a disease or condition associated with an aberrant or unwanted TGF-β expression or activity, by administering to the subject an agent which modulates TGF-β expression or activity. Subjects at risk for a disease which is caused or contributed to by aberrant expression or activity of TGF-β can be identified by, for example, any or a combination of diagnostic or prognostic assays as described herein. Administration of a prophylactic agent can occur prior to the manifestation of symptoms characteristic of the TGF-β aberrancy, such that a disease or disorder is prevented or, alternatively, delayed in its progression.

Another aspect of the invention pertains to methods of modulating TGF-β expression or activity for therapeutic purposes. Accordingly, in an exemplary embodiment, the modulatory method of the invention involves contacting a cell with an agent that modulates one or more of the activities of TGF-β. An agent that modulates TGF-β protein activity can be an agent as described herein, such as a nucleic acid or a protein, a TGF-β antibody, a TGF-β antagonist, a nucleic acid molecule or other small molecule. In one embodiment, the agent inhibits one or more TGF-β activities. Examples of such inhibitory agents include antisense TGF-β nucleic acid molecules, anti-TGF-β antibodies, and TGF-β antagonists. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of TGF-β, e.g., Marfan syndrome or an associated disease or disorder. In one embodiment, the method involves administering an agent, or combination of agents that modulates TGF-β expression or activity.

The invention further provides kits comprising agents or pharmaceutical compositions of the invention and instructions for use. In one embodiment, the kits of the invention are for the treatment of diseases and disorders characterized by aberrant expression or activity of TGF-β. In a related embodiment, the TGF-β associated disease or disorder is Marfan syndrome or a disease or disorder related to Marfan syndrome.

EXAMPLES

It should be appreciated that the invention should not be construed to be limited to the examples that are now described; rather, the invention should be construed to include any and all applications provided herein and all equivalent variations within the skill of the ordinary artisan.

Example 1

Example 1 Demonstrates that the Marfan Syndrome and Associated Diseases and Disorders are Characterized by Increased TGFβ Signaling Failure of Alveolar Septation Due to Excessive TGFβ Signaling in Fibrillin-1-Deficient Mice.

Figure 1:
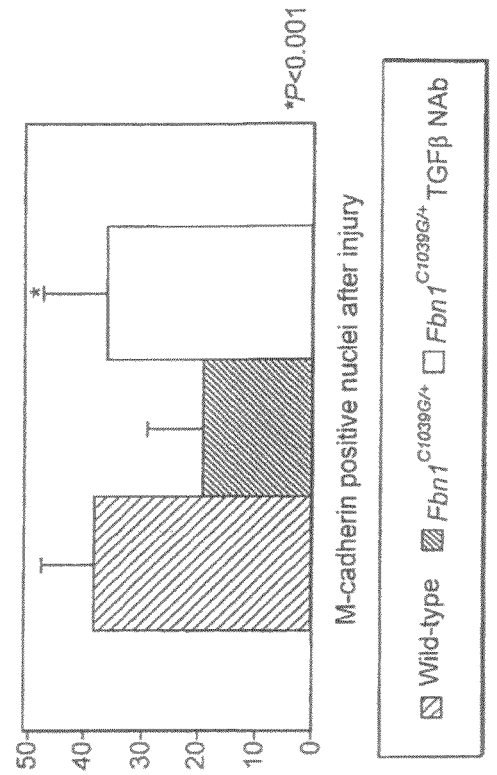
Figures 2, 17B:
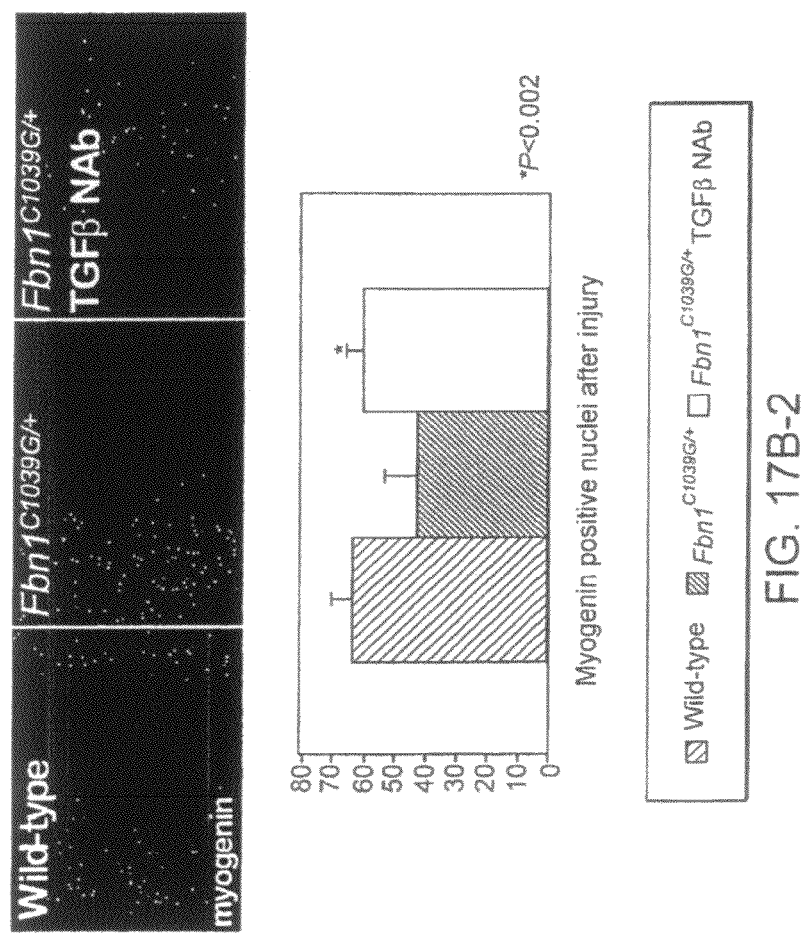

A) Fibrillin-1-deficient mice display primary failure of distal airspace septation: Although the majority of images shown derive from mgD/mgD mice, identical findings have been observed in mgD/+, mgR/mgR, mgR/+, C1039G/+ and C1039G/C1039G strains (see below and data not shown). The prevailing historical view has been that obstructive lung disease and pneumothorax in MFS manifests the consequence of chronic physiologic stress acting upon a structurally deficient and therefore biomechanically predisposed tissue. Remarkably, histologic examination of fibrillin-1 deficient postnatal day 9 (D9) lungs (after controlled inflation) revealed marked widening of the distal airspace. Precise morphometric analysis demonstrated distal airspace enlargement in both heterozygous and homozygous mutant lungs back to day 1 (FIG. 1). Careful histologic analysis did not show any evidence of destruction or inflammation, but rather a paucity of primordial alveolar septae (arrow heads, FIG. 1) These data are most consistent with primary failure of alveolar septation rather than classic destructive emphysema. Additional studies documented normal content of elastin in the developing lung of fibrillin-1-deficient mice and normal localization to the tip of sparse alveolar septae. Additionally, we have shown normal distribution of markers of both epithelial (SPC) and mesenchymal (SM-actin) differentiation.

Figure 2A:
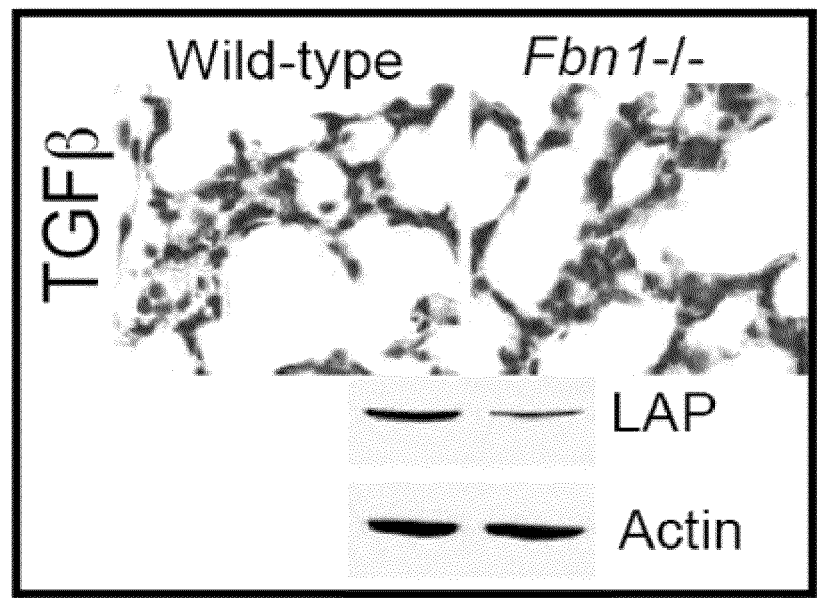
FIGS. 2A-B demonstrate a dramatic increase in immunoreactive material in mutant (−/−) lungs. Data shown in FIG. 2B demonstrated 4- and 25-fold increased TGFβ signaling (GFP signal) in heterozygous (+/−) and homozygous (−/−) Fbn1-targeted mice that harbor the reporter transgene (Tg), as compared to wild-type (+/+), respectively.
Figure 2B:
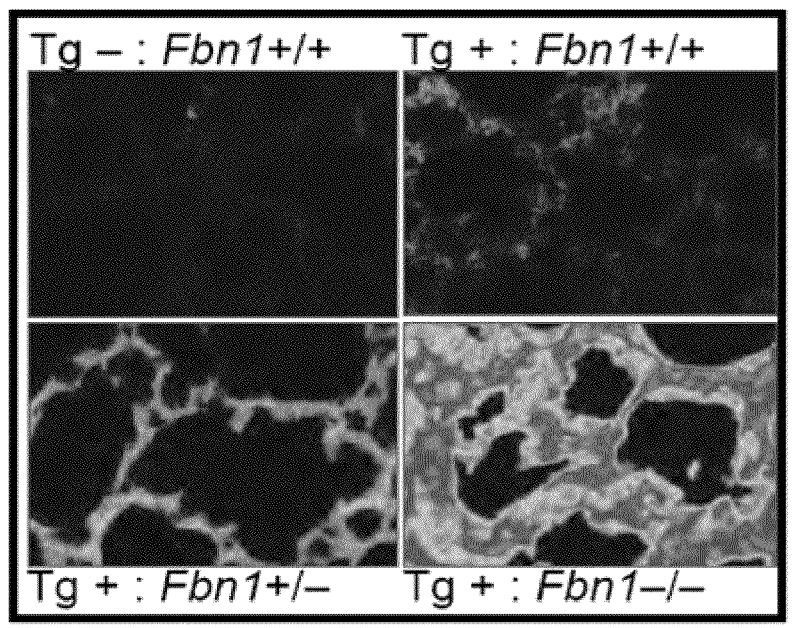

B) Excessive TGFβ activation and signaling in fibrillin-1-deficient lungs: In consideration of potential mechanisms that could impair lung developmental programs, it was believed that fibrillin-1-deficiency could result in dysregulation of TGFβ. This postulate derives from prior knowledge regarding 1) matrix sequestration of the large latent complex, 2) colocalization of LTBPs and microfibrils, and more recently 3) demonstration of direct biochemical interaction between fibrillin-1 and LTBP1. In order to test this model, wild-type (+/+) and fibrillin-1-deficient (−/−) lungs were stained with a polyclonal antibody that is specific for free and active TGFβ1. Data shown in FIG. 2A demonstrate a dramatic increase in immunoreactive material in mutant (−/−) lungs. In contrast, LAP was reduced in abundance, both by immunohistochemistry and western analyses, suggesting increased TGFβ activation rather than production. To address whether increased free TGFβ could translate into increased signaling in this developmental context, a transgenic reporter allele was created that drives GFP expression from a tandem repeat of a TGFβ-responsive promoter element (CAGA box). Prior work showed complete specificity of this element for TGFβ (compared to BMPs or activin). Data shown in FIG. 2B demonstrated 4- and 25-fold increased TGFβ signaling (GFP signal) in heterozygous (+/−) and homozygous (−/−) Fbn1-targeted mice that harbor the reporter transgene (Tg), as compared to wild-type (+/+), respectively.

Figure 3A:
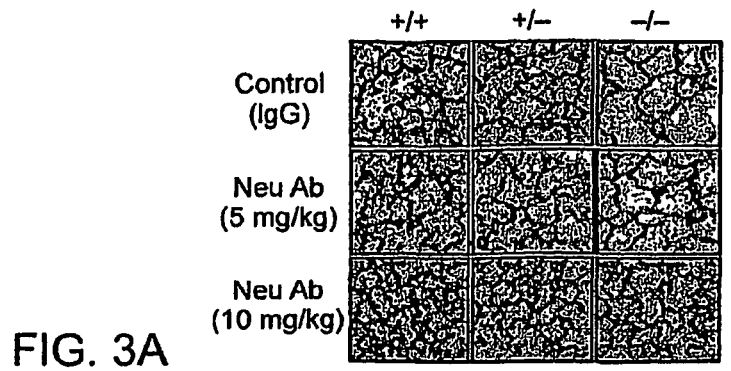
FIGS. 3A-B demonstrate that the analysis of pups at ED7 revealed a dose-dependent rescue of lung septation in both heterozygous and homozygous Fbn1-targeted mice, a result confirmed by morphometry.
Figure 3B:
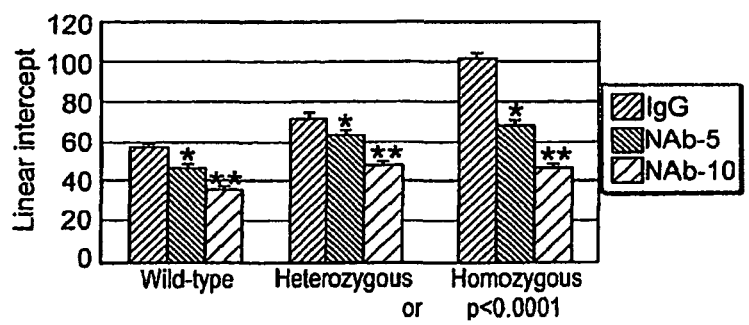

C) Abrogation of TGFβ signaling rescues the lung phenotype in Fbn1-targeted mice: At ED17 and 19, pregnant dams were treated with TGFβ neutralizing Ab (Nab; specific for TGFβ1 and 2) or an irrelevant IgG control. Analysis of pups at ED7 revealed a dose-dependent rescue of lung septation in both heterozygous targeted mice, a result confirmed by morphometry (FIGS. 3A and B, respectively). Importantly, treated wild-type mice showed supra-physiologic septation, documenting that TGFβ is a physiologic negative regulator of alveolar septation. The effect was greatly exaggerated in fibrillin-1-deficient mice, demonstrating excessive TGFβ signaling in the pathogenesis of lung disease in MFS.

Figure 4:
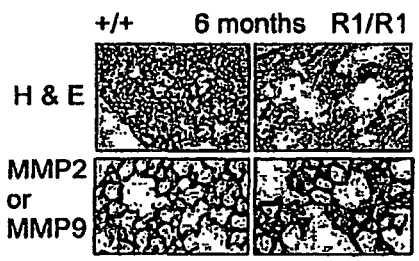
FIG. 4 demonstrates that the lungs of mutant mice showed diffuse airspace enlargement with tissue destruction, inflammation, and increased expression of MMP2 and MMP9.

D) Developmental septation defects evolve into overt emphysema: Analysis of mgR/mgR mice, which live longer than mgD homozygotes, allowed inspection of the natural history of lung disease. At ED6-9, these mice show similar findings to those described above. By 6 months of age, the lungs of mutant mice showed diffuse airspace enlargement with tissue destruction, inflammation, and increased expression of MMP2 and MMP9 (FIG. 4 and data not shown). This demonstrates that developmental abnormalities impose a predisposition for later onset, apparently acquired forms of lung disease.

Relevance of Altered TGFβ Signaling to Other Tissues

Excessive TGFβ Signaling is Relevant to Disease Pathogenesis of MFS in Many Tissues.

Figure 5A:
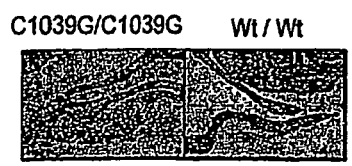
FIGS. 5 A-D depict postnatally-acquired myxomatous changes of the AV valves in fibrillin-1 deficient mice. Echocardiography demonstrated altered function including mitral valve prolapse and regurgitation. These changes associate with increased free TGFβ, increased TGFβ signaling (as evidenced by nuclear accumulation of pSmad2), increased cellular proliferation and decreased apoptosis (marked by Ki67 and TUNEL stains, respectively.
FIG. 5B,C). Prenatal administration of TGFβNAb rescued both valve length and thickness, demonstrating a cause and effect relationship (FIG. 5D).
Figure 5B:
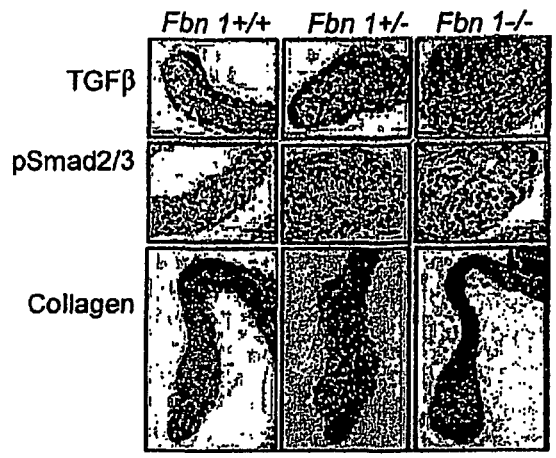
Figure 5C:
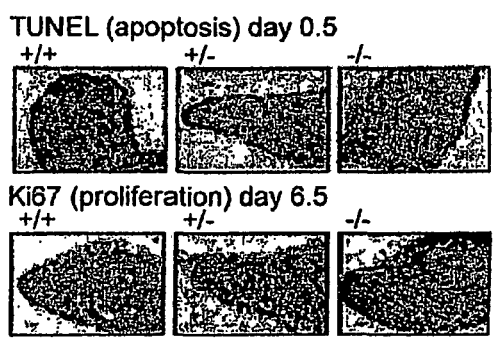
Figure 5D:
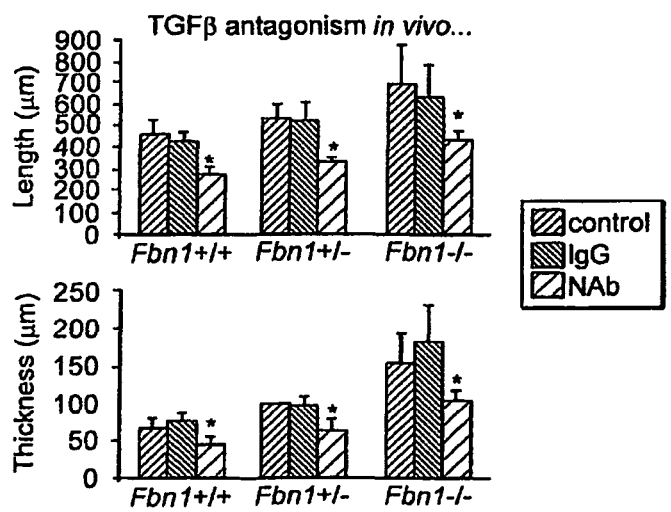

A) Atrioventricular (AV) valves: As shown in FIG. 5A, we have shown postnatally-acquired myxomatous changes of the AV valves in fibrillin-1 deficient mice. Echocardiography demonstrated altered function including mitral valve prolapse and regurgitation. These changes associate with increased free TGFβ, increased TGFβ signaling (as evidenced by nuclear accumulation of pSmad2), increased cellular proliferation and decreased apoptosis (marked by Ki67 and TUNEL stains, respectively; FIG. 5B,C). Prenatal administration of TGFβ NAb rescued both valve length and thickness, demonstrating a cause and effect relationship (FIG. 5D). Expression profiling of mutant valve leaflets showed upregulation of TGFβ responsive genes in including bIGH3, EDN1, and TIMP1. There was also increased expression of multiple bone morphogenetic proteins (BMPs 2, 4 and 6).

Figure 6A:
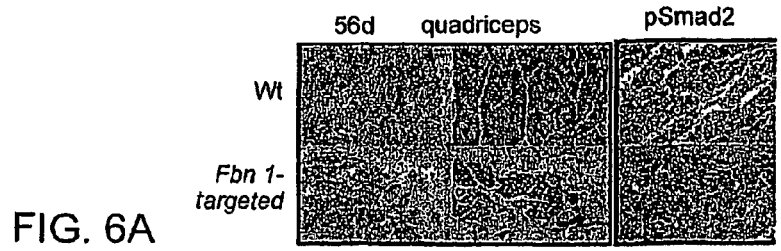
FIGS. 6A-D demonstrate that subjects having MFS have profound skeletal muscle hypoplasia that is associated with hypotonia. Age-dependent changes in all muscle groups examined including a general reduction and wide variation in fiber size, increased endomesial collagen, and cellular dropout with fatty infiltration (FIG. 6A). Fibrillin-1 deficient mice showed a profound failure of muscle regeneration after induced injury (18 days after cardiotoxin injection.
Figure 6B:
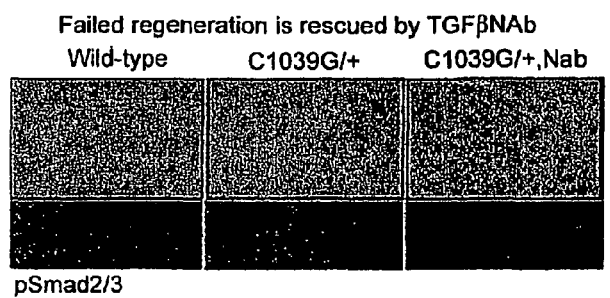
Figure 6C:
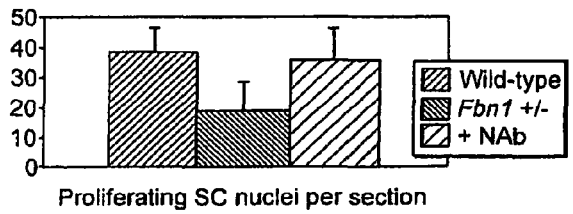
Figure 6D:
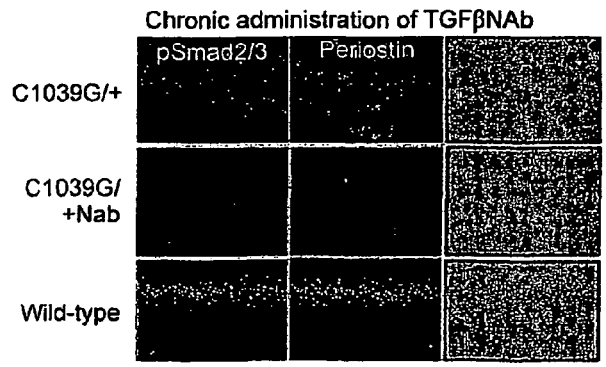

B) Skeletal muscle: Many patients with MFS have profound skeletal muscle hypoplasia that can be associated with hypotonia. The molecular basis for this finding has been entirely unexplored. We found age-dependent changes in all muscle groups examined including a general reduction and wide variation in fiber size, increased endomesial collagen, and cellular dropout with fatty infiltration (FIG. 6A). Identical changes were seen in muscle biopsies from patients with MFS. Once again, these changes correlated with increased free TGFβ, increased TGFβ signaling and increased expression of TGFβ-responsive genes (e.g. periostin). Fibrillin-1 deficient mice showed a profound failure of muscle regeneration after induced injury (18 days after cardiotoxin injection; FIG. 68). In theory, this could relate to either reduced number or reduced proliferation of satellite cells (SCs), i.e., resident muscle stem cells that are essential for normal muscle regeneration. We found a normal quotient of SCs (marked by C-met staining), but a dramatic reduction in proliferating SCs (marked by M-cadherin staining; FIG. 6C). This response was fully normalized after injection of TGFβ NAb, including restored proliferation in response to injury, decreased pSmad2 and periostin expression, and normalization of muscle architecture with centrally-nucleated muscle fibers which is direct evidence of successful regeneration (FIG. 6B,C). Mice receiving chronic administration of NAb showed normal steady-state muscle architecture (FIG. 6D). All visual impressions were confirmed by precise morphometry.

Figure 7A:
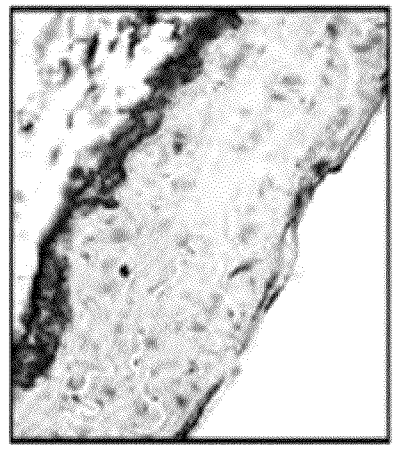
FIGS. 7A-B demonstrate increased TGFβ in the ascending aorta of fibrillin-1-deficient mice.
Figure 7B:
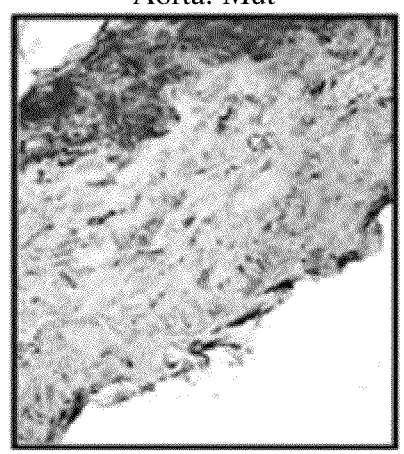

C) TGFβ and other tissues: Increased TGFβ has also been demonstrated in other tissues including the ascending aorta (FIG. 7), hypertrophic chondrocytes in the growth plate, and the dura. Unlike alveolar septation or AV valve remodeling, which occur over a brief and predictable time interval in the immediate postnatal period, or muscle regeneration, that can be rapidly induced and quantitatively assessed, long bone overgrowth, aneurysm formation, and dural sac expansion occur insidiously and represent continuous (rather than discrete) phenotypes. A series of genetic and/or pharmacologic manipulations have been used to monitor their progression over time. These studies are outlined below.

Pharmacologic Manipulation of TGFβ Signaling

Figure 8A:
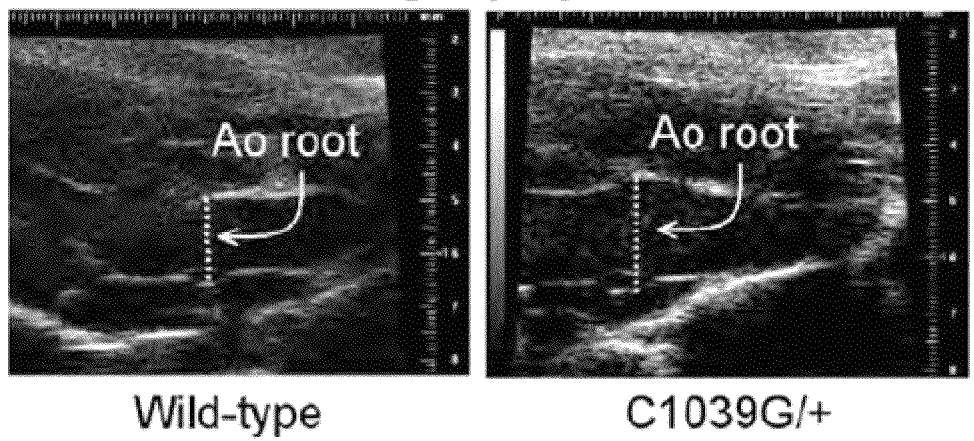
FIGS. 8A-H demonstrate that treatment with losartan is effective for Marfan syndrome and associated disorders. C1039G/+ mice were randomized to one of three treatment arms (n>7 per group) at 7 weeks of age: placebo, losartan (50 mg/kg) or propranolol (40 mg/kg). The doses in each treatment arm were titrated to achieve comparable hemodynamic effects. Three independent measurements of the aortic root were made from the long axis echo view in systole at each of 3 time points (baseline, 2 and 4 months of treatment (FIG. 8A). All analyses were performed blinded to genotype and treatment arm. Aortic growth during the 4 months of treatment was significantly reduced in the losartan (0.03±0.07 mm; p<0.0001) and propranolol (0.22±0.06; p<0.001) groups, compared to placebo (0.44±0.09) (FIG. 8B). The growth in the losartan group was less than that seen with propranolol (p<0.01) and indistinguishable from that seen in wild-type mice. Propranolol treatment did not improve elastic matrix architecture while all histologic parameters were normalized in losartan-treated mice (FIG. 8 C,D). Studies show that administration of TGFβ-neutralizing antibody provided similar protection (p<0.02). Losartan also rescued other aspects of the phenotype including alveolar septation (FIG. 8E) and muscle regeneration and architecture (FIG. 8F). Losartan has proven to be effective in young patients (n=8) with an aggressive rate of aortic growth despite standard therapy (βadrenergic/ACE blockade; representative patients shown in FIG. 8G). As direct evidence that the efficacy of losartan does not strictly relate to its blood pressure-lowering properties, little improvement was observed in any parameter after treatment with a dose of propranolol that achieved the same antihypertensive effect as losartan (FIGS. 8B-E), and showed that TGFβ neutralizing antibody could achieve similar rescue in mice (FIG. 8H).
Figure 8B:
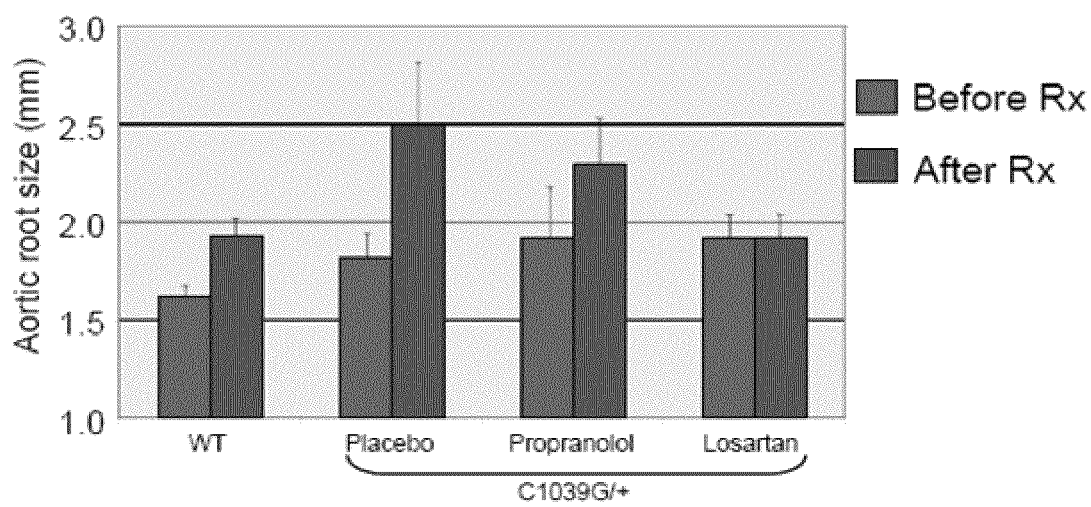
Figure 8C:
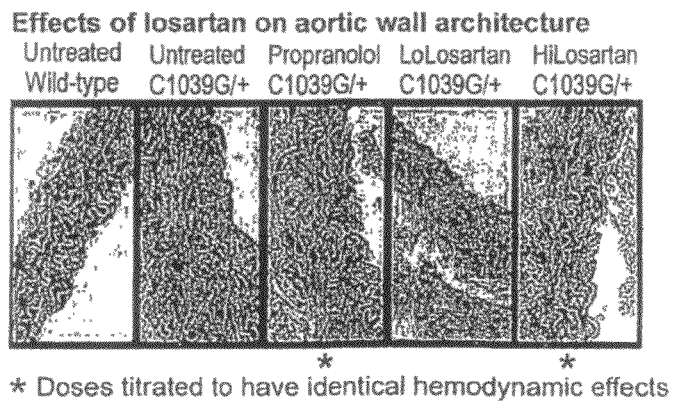
Figure 8D:
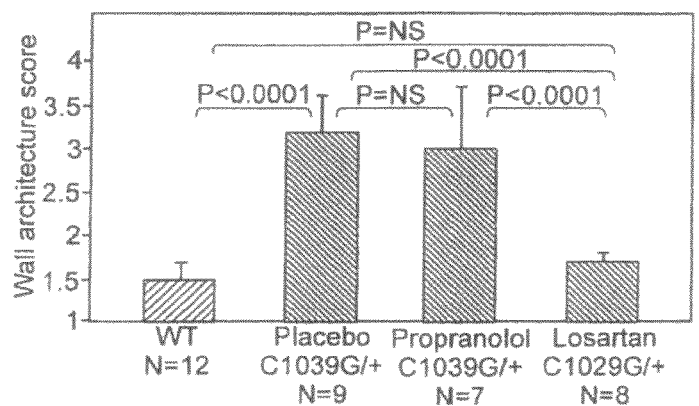
Figure 8E:
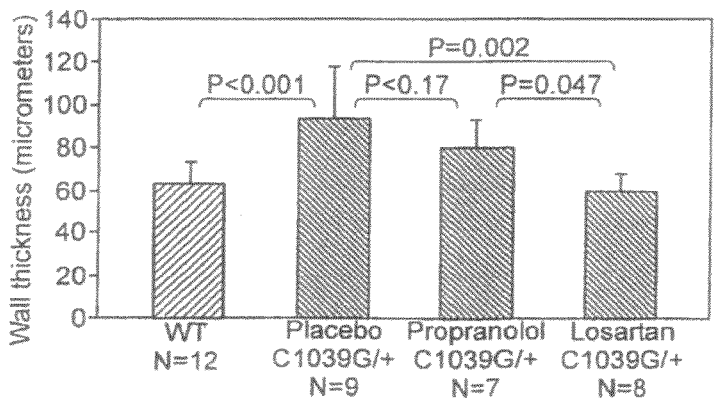
Figure 8F:
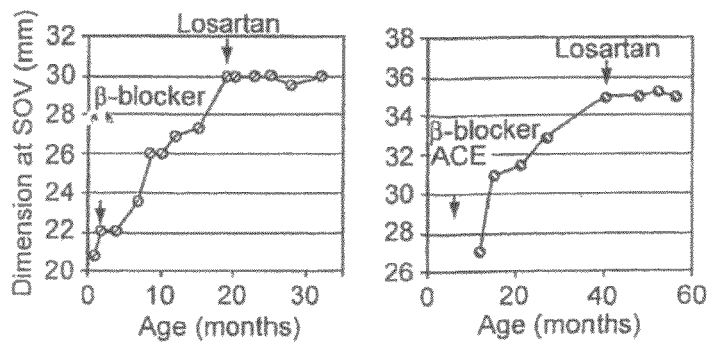
Figure 8G:
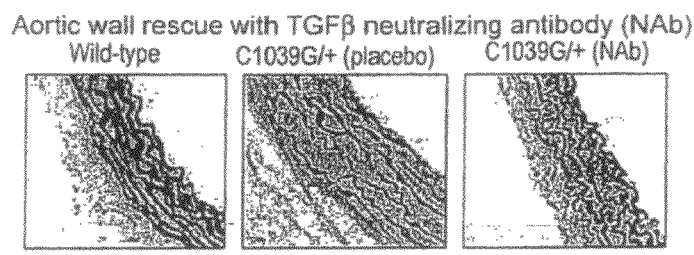
Figure 8H:
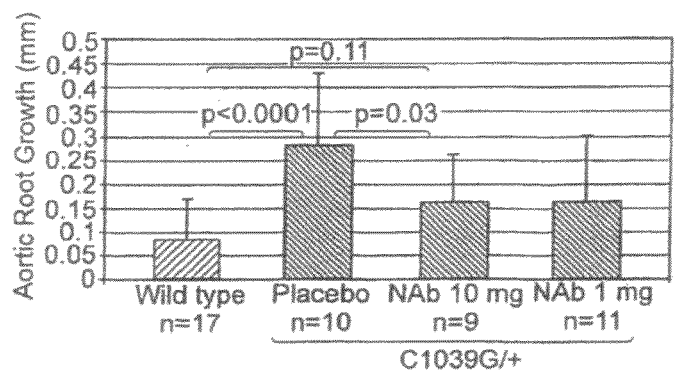

There is an extensive literature describing the ability of angiotensin II type 1 (AT1) receptor blockers (e.g. losartan) to achieve a clinically-relevant inhibition of TGFβ signaling in vivo. For many disease states, including chronic renal disease and cardiomyopathy, the antifibrotic effects of losartan have been directly linked to TGFβ inhibition, and occur independently of the hemodynamic consequences of drug use. Markers of TGFβ antagonism have included reduced plasma levels of free TGFβ, reduced intracellular initiation of the TGFβ signaling cascade, and reduced tissue expression of TGFβ-responsive genes. We believed that treatment with losartan, would provide particular protection from aneurysm by both decreasing hemodynamic stress and attenuating TGFβ-initiated pathogenetic events. C1039G/+ mice were randomized to one of three treatment arms (n≥7 per group) at 7 weeks of age: placebo, losartan (50 mg/kg) or propranolol (40 mg/kg). The doses in each treatment arm were titrated to achieve comparable hemodynamic effects. Three independent measurements of the aortic root were made from the long axis echo view in systole at each of 3 time points (baseline, 2 and 4 months of treatment; FIG. 8A). All analyses were performed blinded to genotype and treatment arm. Aortic growth during the 4 months of treatment was significantly reduced in the losartan (0.03±0.07 mm; p<0.0001) and propranolol (0.22±0.06; p<0.001) groups, compared to placebo (0.44±0.09) (FIG. 8B). The growth in the losartan group was less than that seen with propranolol (p<0.01) and indistinguishable from that seen in wild-type mice. Propranolol treatment did not improve elastic matrix architecture while all histologic parameters were normalized in losartan-treated mice (FIG. 8 C,D). Preliminary studies demonstrated that administration of TGFβ-neutralizing antibody provided similar protection (p<0.02). Losartan also rescued other aspects of the phenotype including alveolar septation (FIG. 8E) and muscle regeneration and architecture (FIG. 8F). We have now seen a remarkable response to losartan in young patients (n=8) with an aggressive rate of aortic growth despite standard therapy (badrenergic/ACE blockade; representative patients shown in FIG. 8G). As direct evidence that the efficacy of losartan does not strictly relate to its blood pressure-lowering properties, there was little improvement in any parameter after treatment with a dose of propranolol that achieved the same antihypertensive effect as losartan (FIGS. 8B-E), and showed that TGFβ neutralizing antibody could achieve similar rescue in mice (FIG. 8H, I). This represents the first therapeutic strategy for MFS that derives from interrogation of disease pathogenesis and the first possibility for primary prevention of disease manifestations.

Treatment of Other Tissues

Figure 9A:
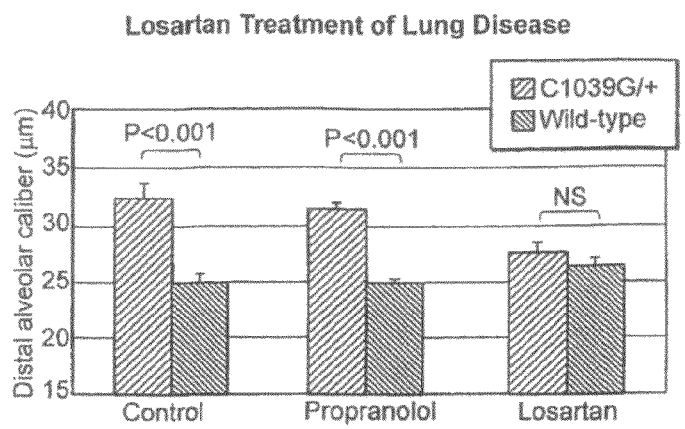
FIGS. 9A-C demonstrate that lungs in treated mice showed normalization of the caliber of the distal airspace, including animals where treated initiated at about 2 months of age (beyond the two week window for alveolar septation that has been previously observe.
Figure 9B:
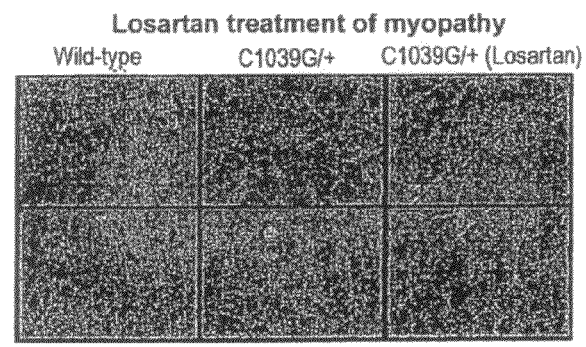
Figure 9C:
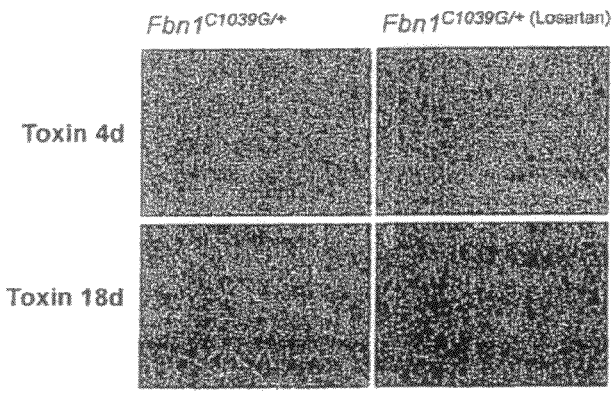

Losartan also had a profound effect on other tissues altered in the Marfan phenotype. The lung in treated mice showed normalization of the caliber of the distal airspace, including animals where treated initiated at about 2 months of age (beyond the two week window for alveolar septation that has been previously observe; FIG. 9A). Losartan also normalized steady-state architecture of skeletal muscle and allowed normal initiation of muscle regeneration at both 4 and 18 days after induced injury with cardiotoxin (FIG. 9B, C).

Treatment of Other Diseases

Figure 10:
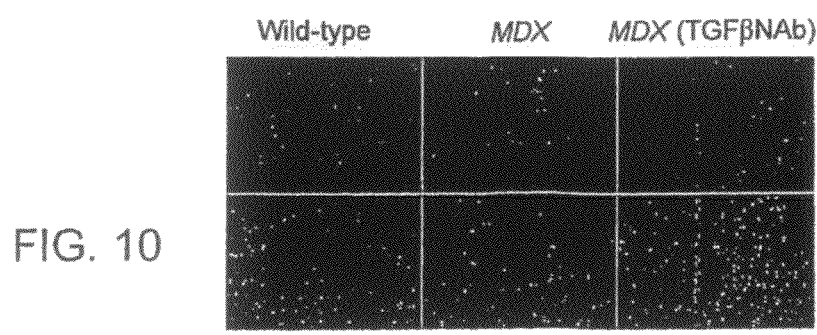
FIG. 10 demonstrates that deficient muscle regeneration in MDX mice (as evidenced by a dramatic paucity for staining with neonatal myosin after injury) was dramatically rescued after administration of TGFb neutralizing Ab.

It was also determined that excessive TGFβ activation and signaling contribute to other forms of muscle disease. The experiments described above have utilized a model of Duchenne muscular dystrophy caused by disruption of the Dystrophin gene (MDX mouse). It was demonstrated that excessive TGFβ signaling in this mouse model via demonstration of increased nuclear accumulation of pSmad2 and increased expression of periostin. Importantly, these same abnormalities were seen in MDX mice that were null for myostatin, another inhibitory TGFβ family member. It was then demonstrated that deficient muscle regeneration in MDX mice (as evidenced by a dramatic paucity for staining with neonatal myosin after injury) was dramatically rescued after administration of TGFβ neutralizing Ab (FIG. 10).

Example 2

Angiotensin II Type I Receptor Blockade Attenuates TGF-β-Induced Failure of Muscle Regeneration in Multiple Myopathic States Mice All mouse protocols were approved by the Animal Care and Use Committee of Johns Hopkins University School of Medicine. Creation of the mouse line harboring the Fbn1 mutation C1039G has been previously described (Judge, D. P. et al. (2004) J Clin Invest 114, 172-81). All analyses were performed in male mice after back-crossing (>9 times) this mutation into the C57BL/6J background, allowing valid comparisons between litters. Mice were sacrificed with an inhalation overdose of halothane (Sigma-Aldrich) or by cervical dislocation. For muscle regeneration experiments in Fbn1$^{C1039G/+}$ mice, 100 μl cardiotoxin (10 μM Naja nigricollis; Calbiochem, La Jolla, Calif.) (Goetsch, S. C. et al. (2003) Physiol Genomics 14, 261-71; Cohn, R. D. et al. (2002) Cell 110, 639-48) was injected into the tibialis anterior muscle of wild-type and Fbn1$^{C1039G/+}$ mice either treated or untreated with TGFβ neutralizing antibody (n=6, each group) at 4 months of age. Subsequently, mice were analyzed at 4, 7, 18 and 28 days after injury. For regeneration experiments in mdx mice we injected 150 μl of cardiotoxin into the tibialis anterior muscle of wild-type and mdx mice, either treated or untreated with TGFβ neutralizing antibody (n=6 each group) at 9 months of age and analyzed skeletal muscle at 4 days and 18 days after injection.

TGFβ-Neutralizing Antibody Treatment

Wild-type and Fbn1$^{C1039G/+}$ mice received intraperitoneal injections of TGFβ-neutralizing antibody (R&D Systems, once every two weeks) starting at 7 weeks of age. The antibody was diluted in PBS (pH 7.4) and administered at a dose of 1 mg/kg or 10 mg/kg body weight. Rabbit IgG (10 mg/kg; Zymed Laboratories Inc.) was administered in a similar fashion as a negative control. Mice were sacrificed after 2 months of treatment and a minimum of 6 mice per genotype were used for histologic and morphometric analyses.

Losartan Treatment

Wild-type and Fbn1$^{C1039G/+}$ mice were begun on treatment at 7 weeks of age with oral losartan (0.6 g/L in drinking water; n=5), or placebo (n=10). Mice were continued on oral therapy for 6 months and sacrificed. For muscle regeneration experiments, fibrillin-deficient and 9 month-old mdx mice were placed on losartan for fourteen days before cardiotoxin was injected. Mice (n=4) continued to be on losartan for the entire period after cardiotoxin induced injury. In order to monitor long-term benefits of losartan treatment, male and female mdx mice (n=6 each group) were started on losartan at the age of 6 weeks. Age-matched wild-type and mdx mice (placebo-treated) served as a control group. After 6 months of treatment, forelimb and hindlimb grip strength was assessed using an automated grip strength meter (Columbus Instruments, Columbus, Ohio). The experiments for forelimb and hindlimb grip strength testing were conducted at different days allowing for a minimum recovery period of 10 days. Total peak force (in Newtons) was determined by an electronic strain gauge as previously described and corrected for body weight (Wagner, K. R., et al. (2002) Ann Neurol 52, 832-6). Five measurements within 2 minutes were taken from each animal. The three highest measurements for each animal were averaged to give the strength score. The degree of fatigue was calculated by comparing the first two pulls to the last two pulls with the decrement between pulls 1+2 and pulls 4+5 providing a measure of fatigue. Similarly, functional measurements were performed in 6 month old fibrillin-1 deficient mice (Fbn1$^{mgR}$) (Pereira, L. et al. (1997) Nat Genet. 17, 218-22) after 5 months of treatment.

Histology and Skeletal Muscle Morphometry

For morphometric analyses, skeletal muscle was flash frozen in cooled isopentane and mounted in Tragacanth (Sigma Aldrich, USA). Subsequently, 10 μm sections were stained with hematoxylin and eosin. Muscle fibers were counted in a defined area (9 mm$^2$) of the tibialis anterior muscle of 10-day-old wild-type (n=3) and Fbn1C1039G/C1039G mice (n=6) and fiber diameter was determined by measuring the shortest fiber axis within cross-sections of the tibialis anterior muscle, counting a total of 850-1500 fibers. The cross sectional area of undamaged and regenerating myofibers of the tibialis anterior muscle from wild-type and Fbn1$^{C1039G/+}$ mice was expressed as a distribution of the percentage of the total number of myofibers analyzed (850-1500) (Horsley, V. et al (2003) Cell 113, 483-94). Sections of skeletal muscle were taken along the same anatomical region of the mid-belly of the tibialis anterior muscle. The number of c-met, M-cadherin- and myogeninpositive cells in 50 fields of the tibialis anterior muscle mid-belly area was scored using the x40 objective. At least six animals per genotype were scored and all analyses were performed by investigators blinded to genotype and treatment group. All images were taken using an Eclipse E400 microscope (Nikon Inc.) and cross-sectional area measurements were determined using IPLAB software (Scanalytics, Fairfax, Va.). Neonatal myosin-positive fibers after cardiotoxin challenge were quantified by counting 900-1240 fibers per toxin-challenged muscle (n=4). For quantification of fibrotic tissue formation in toxin challenged mice (n=4), immunofluorescent staining for vimentin was performed. Five sections throughout the entire tibialis anterior muscle were analyzed at low magnification and vimentin positive areas were calculated as a percentage of the total muscle area using the NIH Scion image software, public domain. Similarly, van-Gieson and vimentin stained sections were used to delineate the percentage of fibrotic versus total muscle area in diaphragm and gastrocnemius of long-term losartan-treated, placebo-treated mdx and wild-type mice (n=6 each group) using the NIH Scion software. For evaluation of percent centrally located nuclei a total of 1100-1300 muscle fibers per diaphragm of each mouse (n=6, each group) and a total of 1900-2200 muscle fibers per gastrocnemius of each mouse (n=6, each group) were calculated.

Statistical Analysis

All values are expressed as mean±SEM. To determine significance between two groups, comparisons were made using the unpaired Student's t tests. Analyses of multiple groups were performed using one-way ANOVA with p<0.05 considered statistically significant.

Immunofluorescence

Immunofluorescent studies were performed as previously described (Cohn, R. D. et al. (2002) Cell 110, 639-48). Staining of satellite cells was performed on frozen sections fixed in 4% paraformaldehyde, then washed in PBS containing 0.3% Triton X for 15 min and subsequently blocked with 5% bovine serum albumin. The following antibodies were used in this study: goat polyclonal anti-pSmad 2/3, rabbit polyclonal anti c-met and rabbit polyclonal anti-myogenin (all from Santa Cruz Biotechnology Inc.); rabbit polyclonal anti-pSmad2 (#3104, Cell Signal) rat polyclonal anti-lamininyl, rabbit polyclonal anti-dystrophin, rabbit polyclonal antithrombospondin-1 and rabbit polyclonal anti-periostin (all from Abcam); rabbit polyclonal anti-fibrillin-1 (pAb 9543) (Judge, D. P. et al. (2004) J Clin Invest 114, 172-81); goat polyclonal anti-vimentin (Sigma) and, mouse monoclonal anti-beta-sarcoglycan mouse monoclonal anti-developmental myosin (Novocastra). Anti a-dystroglycan antibody IIH6 was generously supplied by Dr. Kevin Campbell, Iowa. Secondary Alexa fluor donkey anti-rabbit, anti-rat, anti mouse IgM and IgG1 and anti-goat conjugated antibodies (Molecular probes) were applied for 1 hour at room temperature. Nuclei were stained with DAPI for 5 minutes, and inverted coverslips were mounted onto glass slides using Cytoseal (Vector Laboratories).

Skeletal muscle regeneration and repair is a highly complex and only partially understood process orchestrated by activation of muscle satellite cells. Elucidation of the mechanisms involved in the plasticity of skeletal muscle is of broad interest as modulation and enhancement of muscle regeneration is of potential benefit to patients with various muscle disorders including degenerative diseases of skeletal muscle. TGFβ belongs to a family of cytokines that transduce their signal through the SMAD intracellular signaling cascade (Heldin, C. H., et al. (1997) Nature 390, 465-71). In skeletal muscle, there is in vitro evidence that TGFβ impairs myocyte differentiation during myogenesis (Allen, R. E. & Boxhorn, L. K. (1987) J Cell Physiol 133, 567-72; Martin, J. F., Li, L. & Olson, E. N. (1992) J Biol Chem 267, 10956-60; Zhu, S., et al. (2004) Circ Res 94, 617-25; Olson, E. N., et al. (1986) J Cell Biol 103, 1799-805; Liu, D., Kang, J. S. & Derynck, R. (2004) Embo J 23, 1557-66). In addition, TGFβ has been implicated in the formation of fibrosis in response to injury, inflammation or disease (Li, Y. et al. (2004) Am Jo Pathol 164, 1007-19; Salvadori, C., et al. (2005) Muscle Nerve 31, 192-8; Gosselin, L. E. et al. (2004) Muscle Nerve 30, 645-53; Leask, A. & Abraham, D. J. (2004) Faseb J 18, 816-27). However, a pathogenetic role for TGFβ in other aspects of inherited myopathic disorders has not been demonstrated.

Figure 15A:
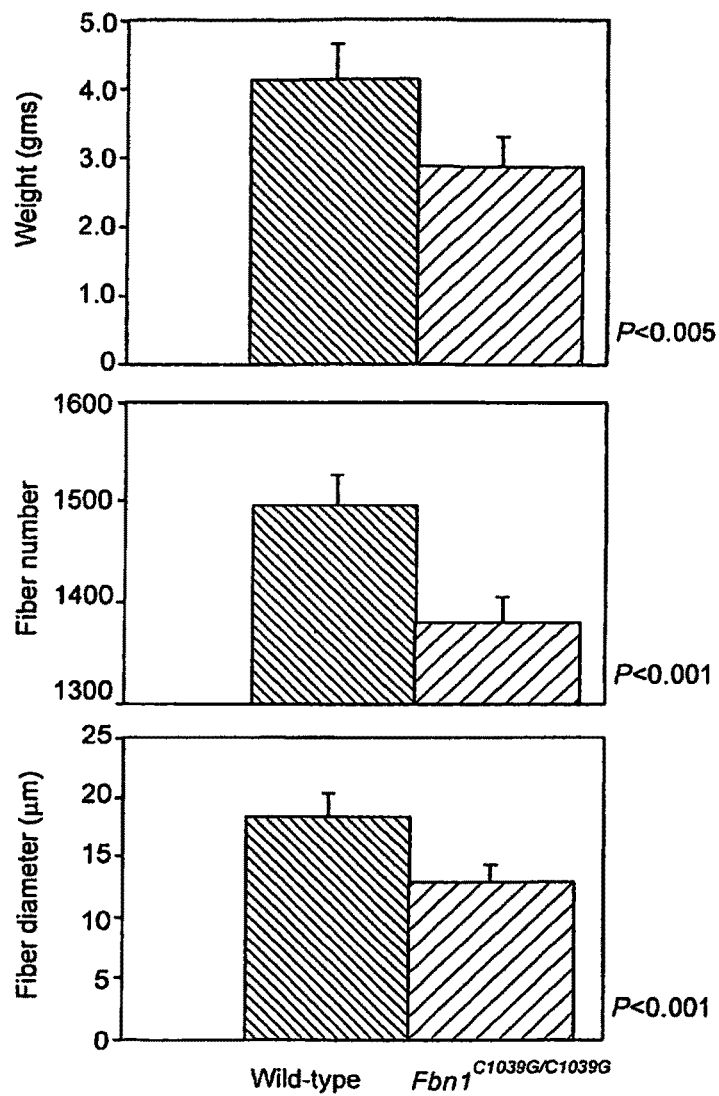
FIGS. 15 A-D demonstrate that total body weight is significantly reduced in Fbn1C1039G/C1039G mice (A). Mean muscle fiber number and mean fiber diameter are expressed±SEM, demonstrating a decrease in both fiber number and size in Fbn1C1039G/C1039G mice. (b) Severe muscle hypoplasia and hypotropy in Fbn1C1039G/C1039G mice. Hematoxylin and eosin staining reveals variation in skeletal muscle fiber size of Fbn1C1039G/C1039G mice at 10-days with smaller fibers and increase interstitial tissue between fibers, when compared to age matched wild-type littermates (M. quadriceps). Bar represents 40 μm. (c) Fibrillin-1 deficiency causes skeletal myopathy in heterozygous Fbn1$^{C1039G/+}$ mice. Immunohistochemical staining for fibrillin-1 reveals decreased endomysial and perimysial expression in Fbn1$^{C1039G/+}$ mice, as compared to wild-type littermates. (d) Decreased endomysial expression of fibrillin-1 in a 5-year-old patient with Marfan syndrome (MFS, *M. lattissimus dorsi*). Note the reduction and significant variation in fiber size and endomysial thickening as compared to a 5-year-old boy without any evidence of a skeletal muscle disorder. Bar represents 45 μm.
Figure 15B:
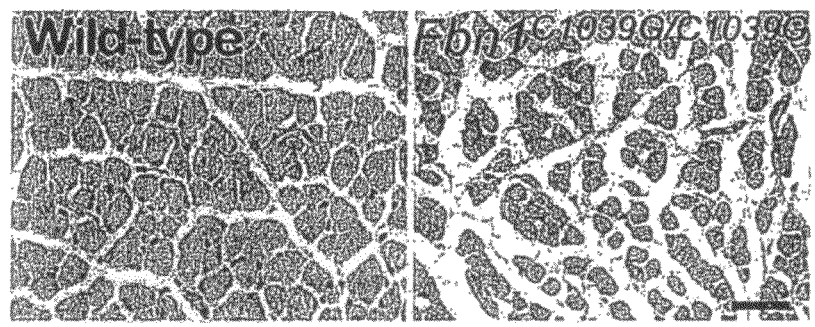
Figure 15C:
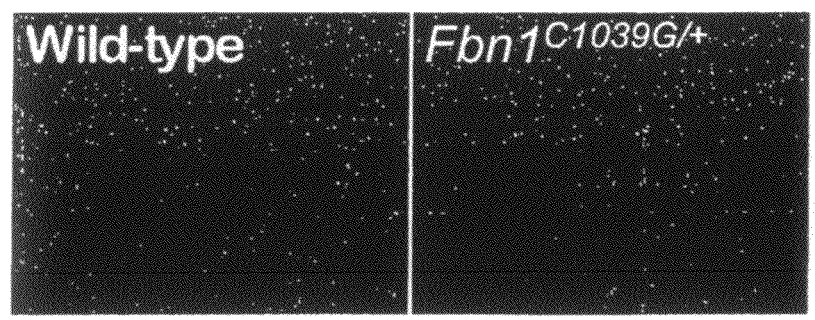
Figure 15D:
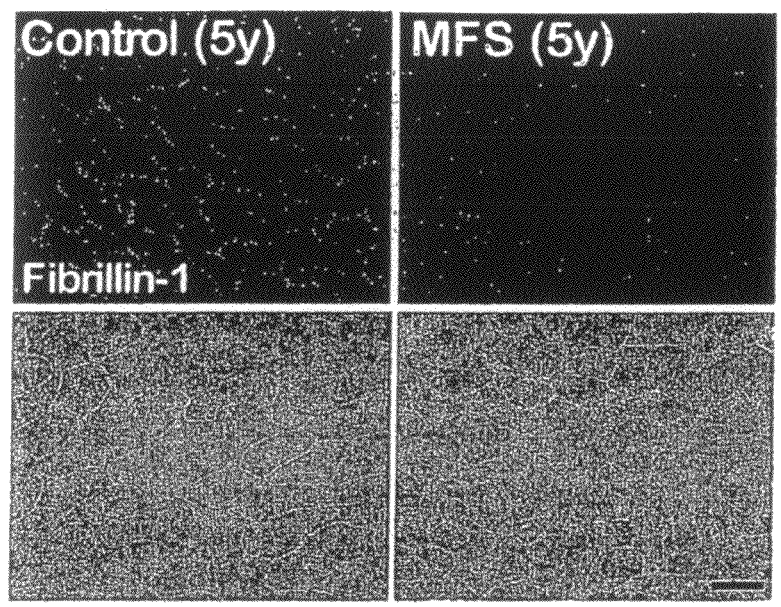

In order to investigate a potential role for TGFβ signaling in the development of myopathy in fibrillin-1 deficient mice we analyzed animals carrying a targeted mutation (C1039G) in exon 25 of the mouse Fbn1 gene (Judge, D. P. et al. (2004) J Clin Invest 114, 172-81). This mutation is representative of the most common class of mutation causing human Marfan syndrome, i.e. cysteine substitutions in EGF-like domains. Mice homozygous for the C1039G mutation (Fbn1$^{C1039G/C1039G}$) have an emaciated appearance and die between 10-14 days of age secondary to aortic dissection. Analysis of 10-day-old wild-type and homozygous mutant litter mates showed a significant discrepancy in body weight (4.13 g±0.5 g vs. 2.86 g±0.41, respectively; p<0.005) that correlated with architectural abnormalities in all skeletal muscle groups examined (quadriceps, diaphragm, gastrocnemius, tibialis anterior, soleus and biceps). Abnormalities included a marked decrease in muscle fiber size (18.5 μm±2 vs. 133 μm±1.5, p<0.001; FIG. 15a), and fiber number (1504±26 fibers vs. 1380±25 fibers, p<0.001; Supplementary FIG. 15a) and increased amounts of interstitial tissue and fat between muscle fiber bundles (FIG. 15b). These findings provide evidence for both muscle hypotrophy and muscle hypoplasia. Mice heterozygous for the C1039G mutation (Fbn1$^{C1039G/+}$) recapitulate the dominant nature of human MFS and show phenotypic manifestations in the pulmonary, cardiovascular and skeletal systems. Immunohistochemical staining for fibrillin-1 revealed decreased endomysial expression in skeletal muscle from Fbn1$^{C1039G/+}$ mice (FIG. 15c) and patients with MFS (n=4; FIG. 15d). Significant variation in fiber size and endomysial fibrosis was observed in both sets of samples (FIG. 11a, FIG. 15c).

Figure 16B:
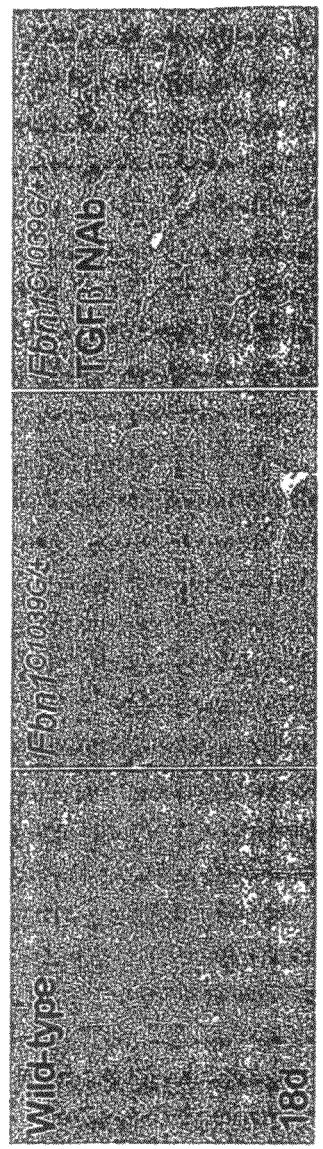

Skeletal muscle from Fbn1$^{C1039G/+}$ mice was assessed for increased TGFβ signaling by immunohistochemical staining for phosphorylated Smad2/3 (pSmad2/3). Ligand-activated TGFβ receptors induce phosphorylation of Smads 2 and 3 which form heteromeric complexes with Smad4 that translocate to the nucleus and mediate target gene responses (Heldin, C. H., et al. (1997) Nature 390, 465-71). Nuclear accumulation of pSmad2/3 was observed in myofibers of Fbn1$^{C1039G/+}$ mice, as compared to wild-type littermates (FIG. 11a, FIG. 16a). No nuclear staining was observed in phosphatase-treated tissue sections (data not shown). Further evidence of increased TGFβ signaling derived from analyses of the expression of periostin, a protein known to be induced by TGFβ and expressed in regenerating skeletal muscle (Horiuchi, K. et al. (1999) J Bone Miner Res 14, 123949; Goetsch, S. C. et al. (2003) Physiol Genomics 14, 261-71). In contrast to wild-type mice, Fbn1$^{C1039G/+}$ animals showed sarcolemmal expression of periostin in mature and uninjured skeletal muscle (FIG. 11a).

To demonstrate a cause-and-effect relationship between excess TGFβ signaling and development of myopathy in Fbn1$^{C1039G/+}$ mice, systemic TGFβ antagonism was achieved in vivo by intraperitoneal injection of 1 mg/kg or 10 mg/kg TGFβ neutralizing antibody (TGFO NAb) beginning at 7 weeks of age. In addition, placebo injections with 10 mg/kg rabbit IgG were administered to wild-type and Fbn1$^{C1039G/+}$ mice. Both TGFβ isoforms 1 and 2 are neutralized in vivo and in vitro by this antibody (Ng, C. M. et al. (2004) J Clin Invest 114, 1586-92; Neptune, E. R. et al. (2003) Nat Genet. 33, 407-11).

Figure 11A:
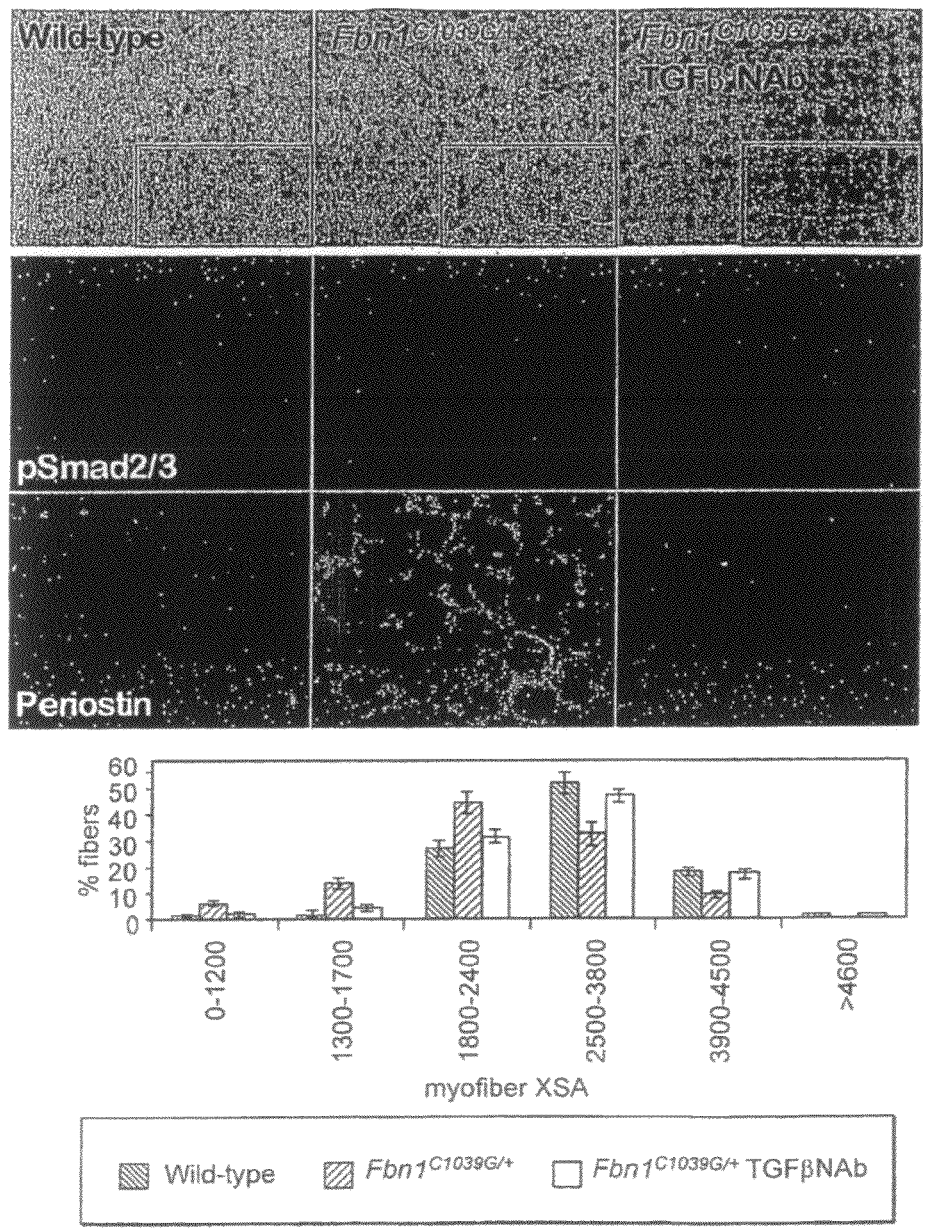
FIGS. 11A-B depict hematoxylin and eosin staining of quadriceps muscle demonstrates marked variation of fiber size in Fbn1$^{C1039G/+}$ mice (upper level). Note several small and split fibers (asterixes), fibers with central nucleation and endomysial thickening. TGFP antagonism in vivo reverses myopathic architecture in Fbn1$^{C1039G/+}$ mice. Evidence for increased TGFP signaling (lower two panels). Immunofluorescent staining for pSmad2/3 reveals increased nuclear staining in Fbn1$^{C1039G/+}$ mice, as compared to wild-type mice. The lower panel shows a serial section with increased sarcolemmal expression of periostin in Fbn1$^{C1039G/+}$ mice, as compared to wild-type mature skeletal muscle. Neither nuclear expression of pSmad2/3 nor sarcolemmal expression of periostin is detected in Fbn1$^{C1039G/+}$ mice treated with TGFP neutralizing antibody. Analysis of the cross sectional area (myofiber XSA in μm$^2$) of tibialis anterior muscle fibers reveals a decrease in fiber size in Fbn1$^{C1039G/+}$ mice (mean fiber size, 1698±49 μm$^2$) when compared to wild-type mice (mean fiber size, 2622±55 μm$^2$) that is restored upon treatment with TGFP NAb (mean fiber size, 2443±41 μm$^2$); $P<0.005$. (b) Impaired muscle regeneration in Fbn1$^{C1039G/+}$ mice. Cardiotoxin-induced injury leads to formation of newly formed myofibers with centrally located nuclei in wild-type and Fbn1$^{C1039G/+}$ mice treated with TGFP NAb 4 days after injection. In contrast, only few new myofibers form in untreated Fbn1$^{C1039G/+}$ mice (upper panel). Numerous small fibers (*), which appeared to have arrested in growth during regeneration are observed in Fbn1$^{C1039G/+}$ mice 18 days after injection of cardiotoxin. In contrast, most of the muscle fibers in wild-type and Fbn1$^{C1039G/+}$ mice treated with TGFP neutralizing antibody have successfully completed regeneration, with an increase and relative homogeneity in fiber size, as compared to untreated mutant littermates. No significant nuclear pSmad2/3 and sarcolemmal periostin staining is observed in wild-type and treated Fbn1$^{C1039G/+}$ mice, as opposed to persistent expression of pSmad2/3 and periostin in untreated Fbn1$^{C1039G/+}$ animals. Analysis of the cross sectional area (myofiber XSA in μm$^2$) of tibialis anterior muscle 18 days after cardiotoxin injection reveals a reduction in mean fiber size in Fbn1$^{C1039G/+}$ mice (1145±69 μm$^2$) that is rescued upon treatment with TGFP Nab (2092±47 μm$^2$; wild-type mice mean fiber size, 2389±51 μm$^2$; $P<0.005$).

Histologic and morphometric assessment revealed prevention of abnormal muscle morphology in mutant animals after 2 months of treatment with TGFβ NAb, independent of the dosage used (FIG. 11a). There was no effect on the morphology of wild-type skeletal muscle at either dose (data not shown). Moreover, neither nuclear accumulation of pSmad2/3 nor sarcolemmal periostin staining was observed in TGFβ NAb-treated Fbn1$^{C1039G/+}$ mic3 (FIG. 11a). These data demonstrate a causal relationship between dysregulated TGFβ signaling and development of skeletal muscle myopathy in a mouse model of MFS.

Figure 11B:
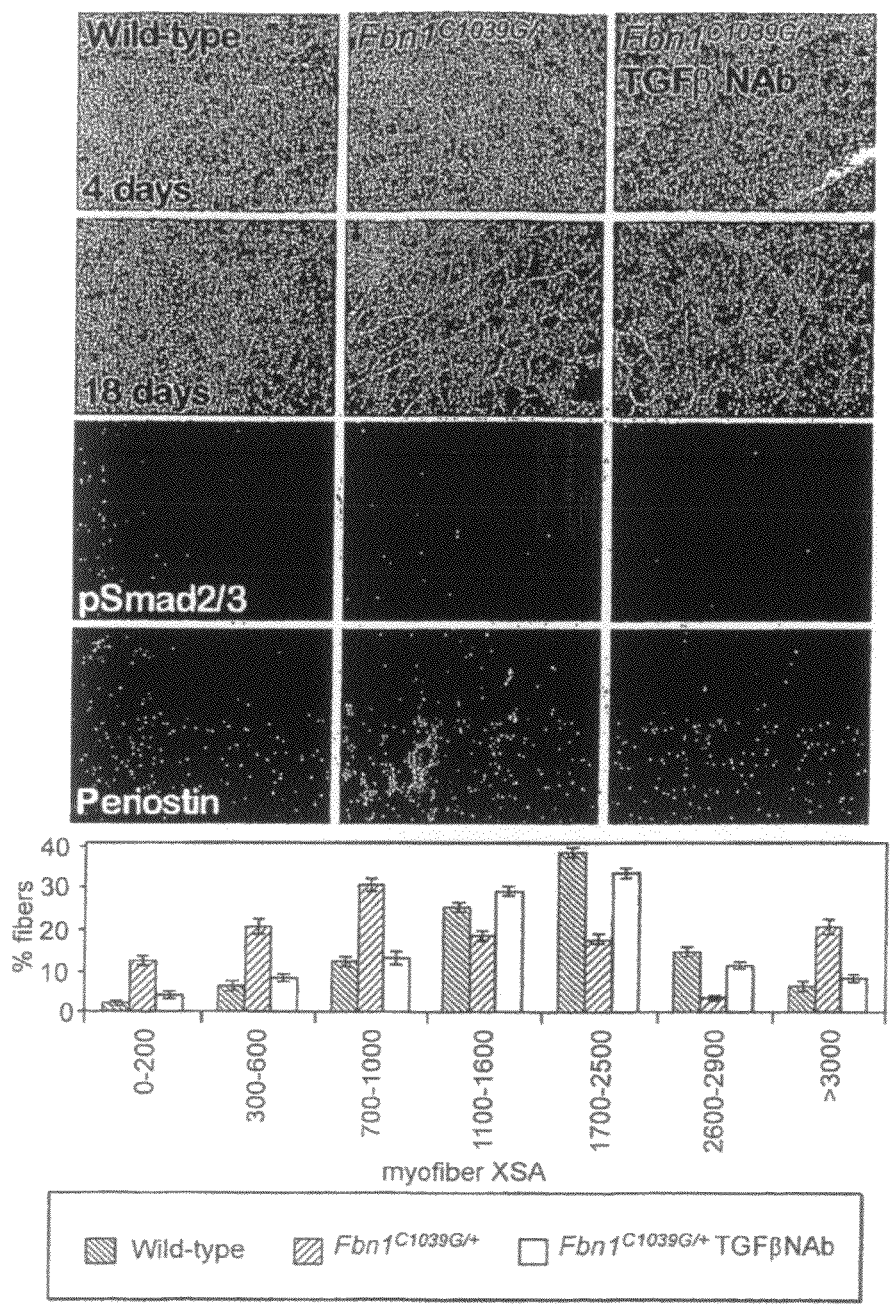

The presence of multiple atrophic and split fibers in skeletal muscle of fibrillin-1 deficient mice and patients with MFS is suggestive of abnormal and/or incomplete muscle regeneration (FIG. 11a, FIG. 15d). To further investigate the potential mechanism by which TGFβ causes the development of skeletal myopathy, the response of skeletal muscle to injury induced by snake venom cardiotoxin was evaluated. Analysis of wild-type skeletal muscle 4 days after cardiotoxin injection revealed evidence of numerous regenerating muscle fibers (FIG. 11b). In contrast, skeletal muscle of Fbn1$^{C1039G/+}$ mice showed delay in regeneration and only scattered newly formed muscle fibers (FIG. 11b).

At 18 days after cardiotoxin injection, muscle regeneration was substantial in wild-type mice while Fbn1$^{C1039G/+}$ mice demonstrated multiple small fibers with focal areas of fibrosis indicative of abnormal muscle repair (FIG. 11b). Systemic administration of TGFβ NAb at the time of and two weeks after cardiotoxin injection significantly improved the muscle regeneration capacity of Fbn1$^{C1039G/+}$ mice as shown by histologic and morphometric analysis of the tibialis anterior muscle at 4 and 18 days after injury (FIG. 11b). All animal groups showed nuclear accumulation of pSmad2/3 and sarcolemmal expression of periostin 4 days after cardiotoxin injection. These findings are consistent with the prior observation of a transient increase in expression of TGFβ 1 and periostin within the first five days of muscle regeneration (Goetsch, S. C. et al. (2003) Physiol Genomics 14, 261-71). In contrast, nuclear accumulation of pSmad 2/3 and periostin expression persisted in Fbn1$^{C1039G/+}$ mice 18 days after injury; this was not observed in wild-type and TGFβ NAb treated Fbn1$^{C1039G/+}$ mice (FIG. 11b). These data suggest that exaggeration and/or prolongation of the physiologic spike in TGFβ signaling that attends muscle injury and repair can limit regeneration and culminate in myopathy.

Figure 17A:
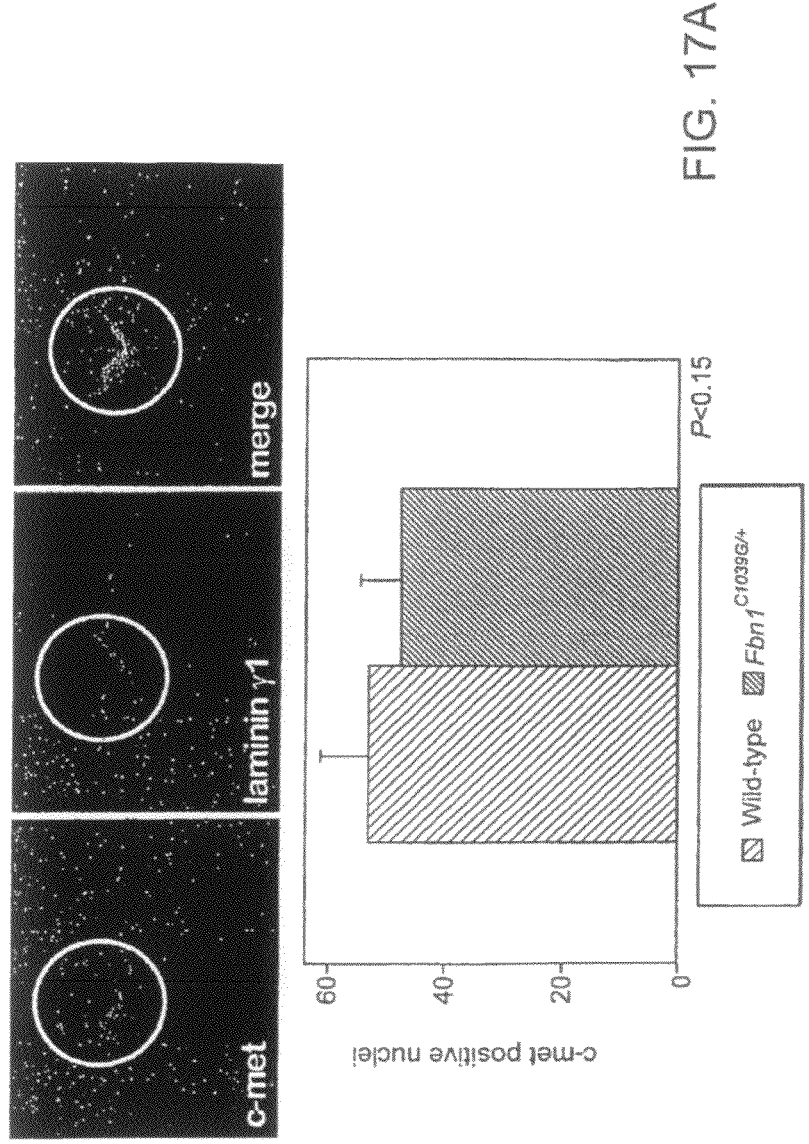
Figure 17B:
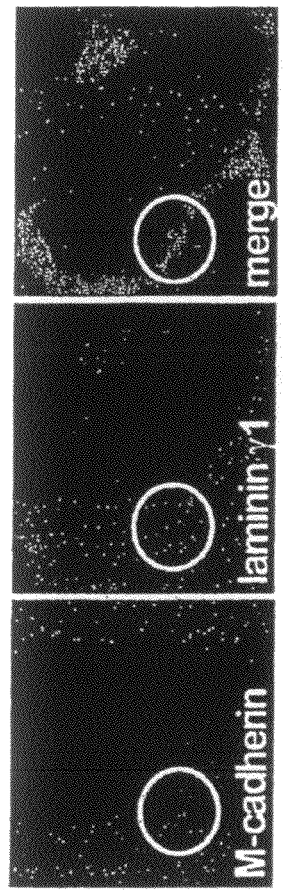

Given the inability to sufficiently repopulate damaged muscle fibers in response to injury, we investigated whether increased TGFβ signaling alters the performance of satellite cells, a population of cells unique to skeletal muscle. In the course of muscle regeneration, satellite cells exit their normal quiescent state and begin proliferating. After several rounds of proliferation, the majority of satellite cells differentiate and fuse, either to form new myofibers or to repair damaged fibers. Analysis of c-met, a marker for quiescent satellite cells, did not reveal any significant difference in the number of satellite cells in wild-type (54±8 cells/field) and Fbn1$^{C1039G/+}$ mice (48±7 cells/field) prior to injury (FIG. 17a). In contrast, immunohistochemical assessment of M-cadherin (a marker for proliferating satellite cells) at 48 h after toxin-induced injury revealed less positively-stained satellite cells in the tibialis anterior muscle of Fbn1$^{C1039G/+}$ mice (19±4 cells/field) when compared to wild-type (38±9 cells/field) or TGFβ Nab treated Fbn1$^{C1039G/+}$ mice (36±6 cells/field; p<0.001) (FIG. 17b). Expression of myogenin, a myocyte regulatory factor known to be involved in proliferation and differentiation of satellite cells (Jin, Y. et al. (2000) Acta Neuropathol (Berl) 99, 619-27), exhibited a similar decrease in the tibialis anterior muscle of Fbn1$^{C1039G/+}$ mice (42±7 cells/field) 72 h after cardiotoxin challenge as compared to wild-type (63±7 cells/field) or TGFβ NAb-treated Fbn1$^{C1039G/+}$ mice (59±6 cells/field; p<0.002) (FIGS. 17b and c). Taken together, these findings demonstrate that augmented TGFβ signaling causes impaired muscle repair by inhibiting satellite cell proliferation and differentiation. These findings may explain both the congenital myopathy and the life-long inability to increase muscle mass in MFS.

Figure 12:
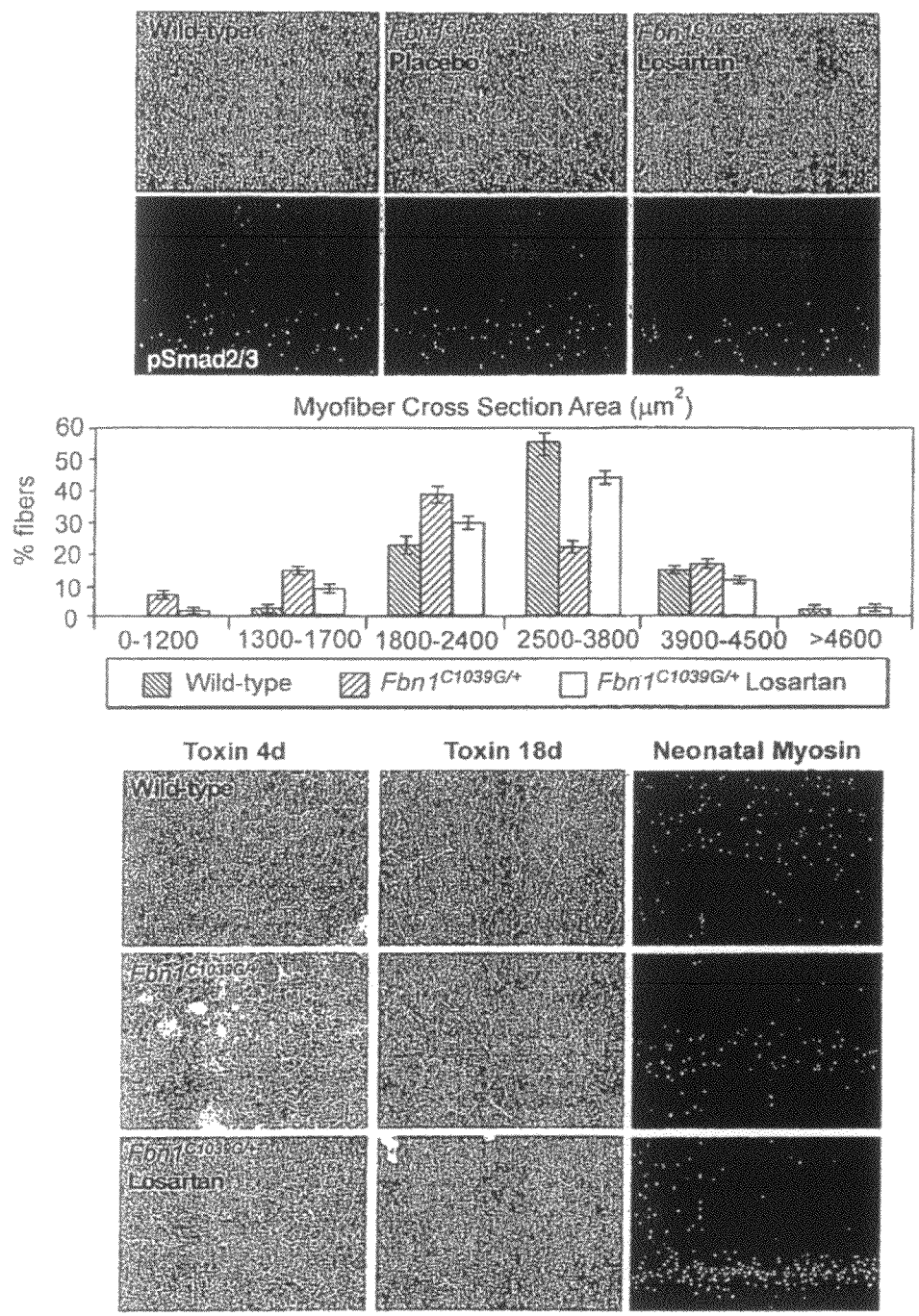
FIG. 12 depicts steady-state skeletal muscle architecture (quadriceps muscle) and nuclear accumulation of pSmad2/3 in wild-type mice and Fbn1$^{C1039G/+}$ mice treated postnatally with placebo and losartan (upper panel). Morphometric analyses revealed reduced muscle fiber cross sectional area in Fbn1$^{C1039G/+}$ mice that was reversed upon treatment with losartan [wild-type mean fiber size, 2741±69 μm$^2$; Fbn1$^{C1039G/+}$ 1746±39 m$^2$; Fbn1$^{C1039G/+}$ plus losartan, 2527±58 μm$^2$; $p<0.009$]. Muscle architecture and neonatal myosin expression 4 days and 18 days after induced injury with cardiotoxin in wild-type and Fbn1$^{C1039G/+}$ mice treated with placebo or losartan (lower panel).
Figure 16C:
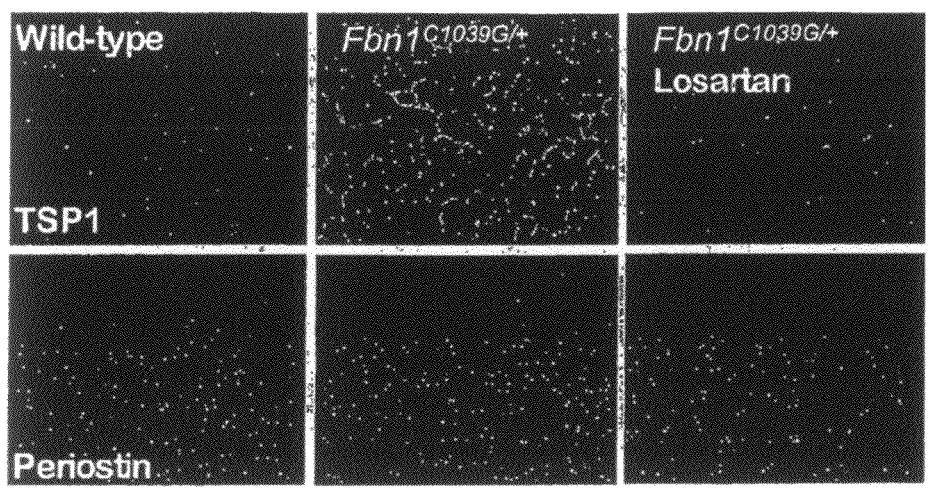
Figure 16D:
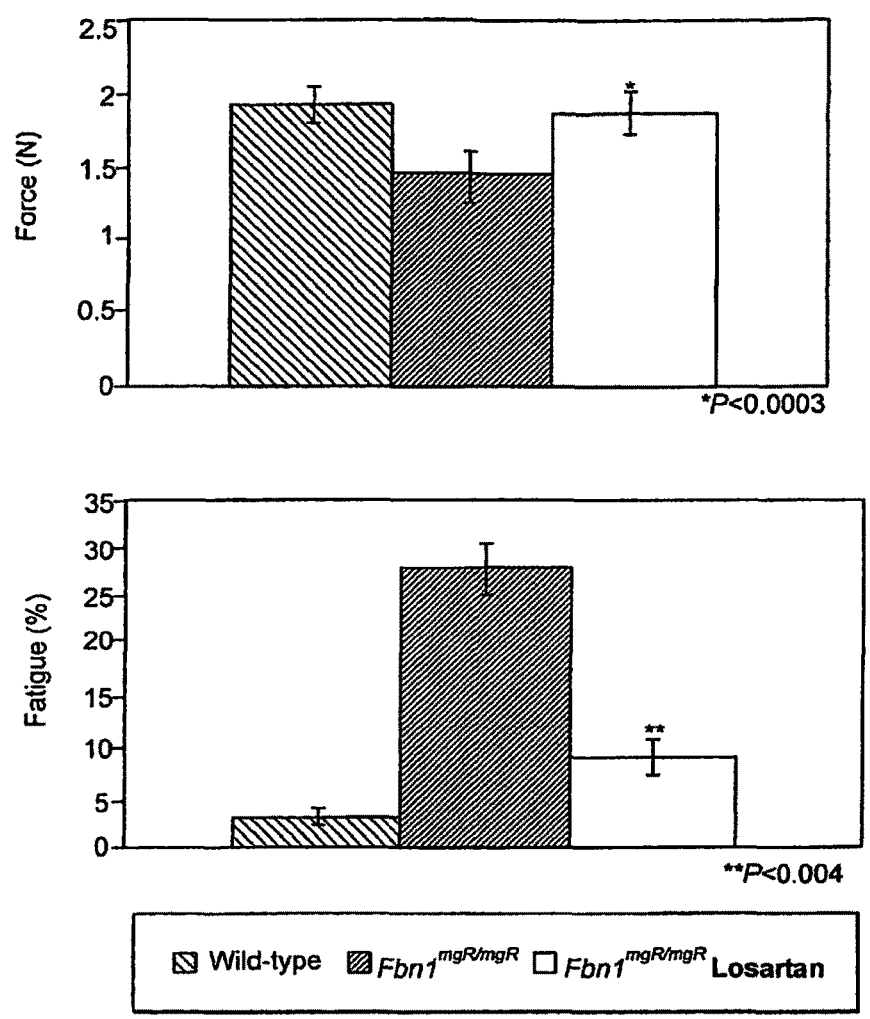

It was then investigated whether losartan, an angiotensin II type 1 receptor (AT1) antagonist which has been shown to lead to a clinically relevant antagonism of TGFβ in other disease states including chronic renal disease and cardiomyopathy (Lavoie, P. et al. (2005) J Hypertens 23, 1895-1903; Lim, D. S. et al. (2001) Circulation 103, 789-91) has an impact on steady state architecture and muscle regeneration in Fbn1 deficient mice. Losartan, an agent which is widely used to treat hypertension, has an exceptional tolerance profile in all age groups and can prevent aortic aneurysm in a mouse model of MFS. Long-term treatment (6 months) with losartan fully normalized muscle steady state architecture in Fbn1$^{C1039G/+}$ mice (FIG. 12). Phenotypic rescue correlated with abrogation of TGFβ signaling in mature skeletal muscle and improved in vivo muscle function (FIG. 12, FIG. 16 a and b). Moreover, we found that administration of losartan prior to cardiotoxin-induced injury markedly improved muscle regeneration in Fbn1$^{C1039G/+}$ mice (FIG. 12).

Figure 13A:
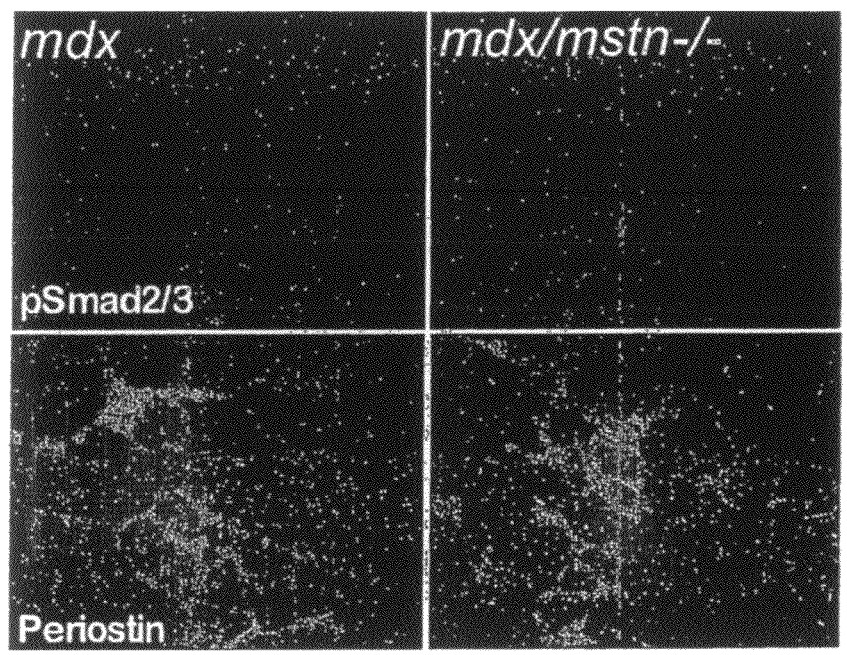
FIGS. 13A-B depict (a) Increased nuclear accumulation of pSmad2/3 and sarcolemmal expression of periostin in dystrophin-deficient mdx mice and mice deficient for both dystrophin and myostatin (mdx/mstn−/−; right panels) and (b) Improved regeneration capacity in mdx mice treated with TGFb NAb. Representative sections are stained for neonatal myosin, a marker for active regeneration, 4 days after cardiotoxin injection (upper panel). Wild-type mice exhibit numerous cells undergoing active regeneration, whereas mdx mice show only scattered regenerating fibers. In contrast, mdx mice treated with TGFP NAb or losartan demonstrate active regeneration comparable to that seen in wild-type mice (second panel from top). Eighteen days after cardiotoxin injection, wild-type mice show almost no fibrosis as shown by negative vimentin staining (green). In contrast, mdx mice show widespread areas of fibrosis, whereas mdx mice treated with TGFb NAb or losartan show a marked reduction in fibrosis (lower tow panels). The graph shows the percentage of fibrotic area as compared to the total area of muscle tissue.

There is descriptive evidence for increased TGFβ activity associated with fibrosis in various genetic and acquired muscle disorders and it has been shown that decorin (a TGFβ antagonist) administration can reduce TGFβ activity and collagen content in the diaphragm of mdx mice (Salvadori, C., et al. (2005) Muscle Nerve 31, 192-8; Gosselin, L. E. et al. (2004) Muscle Nerve 30, 645-53; Yamazaki M et al. (1994) Am J Pathol. 144, 221-226). However, a pathogenetic contribution of increased TGFβ activity to impaired muscle regeneration in these conditions has not been documented. One mechanism in the pathogenesis of various degenerative myopathies including some forms of muscular dystrophy is a decline in satellite cell performance and muscle regeneration over time. TGFβ emerges as an attractive candidate mediator of these effects. As proof of this, we found nuclear accumulation of pSmad2/3 and sarcolemmal expression of periostin in skeletal muscle of dystrophin-deficient mdx mice, an animal model for Duchenne muscular dystrophy (Reimann, J. et al. (2000) Neuromuscul Disord 10, 276-82) (FIG. 13a). One complicating factor in interpretation of these data is that myostatin, another member of the TGFβ superfamily, also signals through the pSmad2/3 cascade (Philip, B. et al. (2005) Cell Signal 17, 365-75; Zhu, X., et al. (2004) Cytokine 26, 262-72). We were able to remove this variable by showing an ongoing increase in nuclear pSmad2/3 and periostin expression in myostatin-null/mdx animals (FIG. 13a). Myostatin is a negative regulator of satellite cell activity and loss of function causes significant muscle hypertrophy in animals and humans. Myostatin antagonism has been shown to ameliorate the muscle phenotype in dystrophin-deficient mdx mice34, however, in contrast to TGFβ, various lines of evidence have demonstrated that myostatin expression is decreased in muscular dystrophy, perhaps as a component of an inadequate physiologic attempt at compensation. Thus, while therapeutic strategies aimed at myostatin antagonism may provide some benefit by targeting a parallel pathway, TGFβ antagonism targets a pathway that appears to contribute directly to the pathogenesis of disease.

Figure 13B:
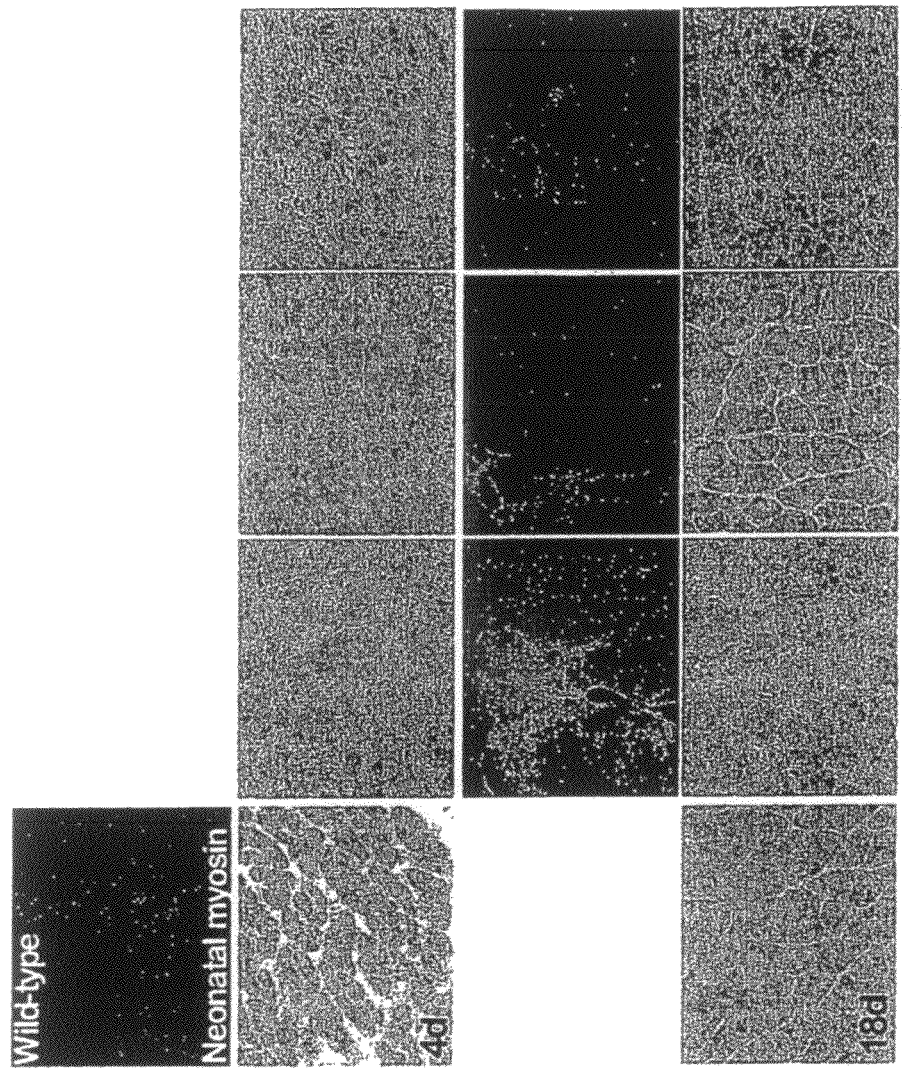

We tested the impact of TGFβ NAb and losartan on the regenerative capacity of 9-month old mdx mice. At four days after injury, wild-type mice showed numerous myofibers expressing neonatal myosin, a marker for active regeneration (689±19 neonatal myosin positive fibers per tibialis anterior muscle, FIG. 13b). Mdx mice showed significant impairment in this response with only few neonatal myosin-positive fibers (268±12 neonatal myosin positive fibers per tibialis anterior muscle) (FIG. 13b). Remarkably, when treated with TGFβ NAb or losartan, mdx mice demonstrated restored regeneration (556±22 and 513±14 neonatal myosin positive fibers per tibialis anterior muscle, respectively; p<0.002) (FIG. 13b). After 18 days, wild-type mice showed complete regeneration, while mdx mice exhibited large areas of tissue fibrosis. Again, mdx mice treated with TGFβ NAb or losartan showed improved muscle repair with reduced fibrosis, as evidenced by reduced vimentin expression (FIG. 13b).

Figure 14A:
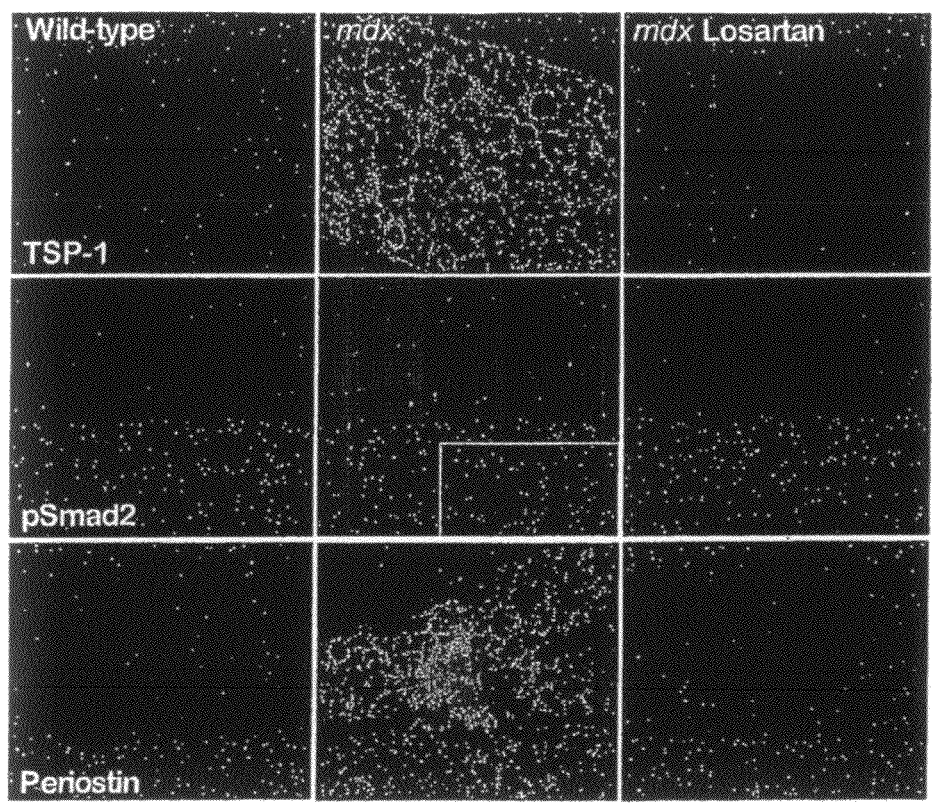
Figure 18A:
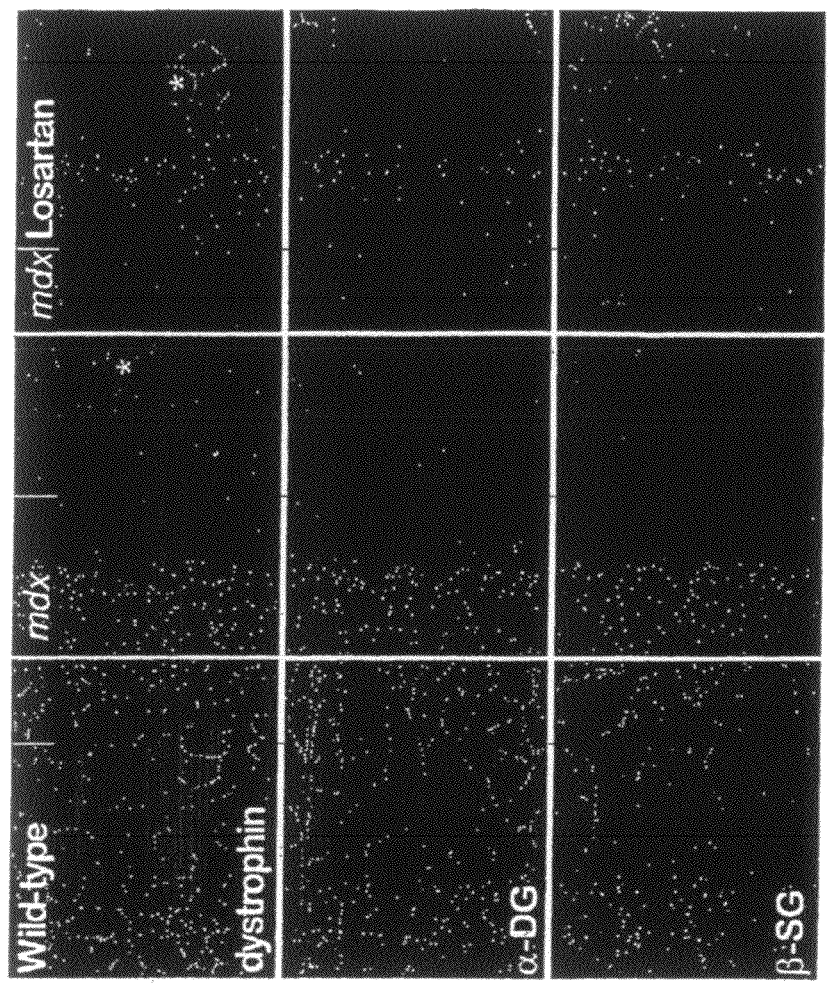
FIGS. 18A-C depict immunofluorescent expression of dystrophin, a-dystroglycan (a-DG), and [i-sarcoglycan ((3-SG) in wild-type, mdx and losartan-treated mdx mice. Dystrophin is absent in treated and untreated mdx mice (*denotes revertant fibers). In addition, sarcolemmal expression of a-dystroglycan and [i-sarcoglycan are reduced in both groups of animal groups when compared to wild-type mice. (b) Creatine kinase levels in wild-type, mdx and losartan-treated mdx mice (n=6 each group). There is no statistical significance between treated versus untreated mdx mice which both show significant elevation of serum creatine kinase. (c) After 6 months, mdx mice treated with losartan (mdx L) demonstrate overall improved forelimb grip strength (measured as peak force in N, upper graph, m=male, f=female, n=6 mice each group) when compared to untreated mdx mice (1.64±0.29[male]/1.41±0.15[female]N versus 1.25±0.15 [male]/1.32±0.12 [female] N; p<0.004 and p<0.008). In addition, losartan treated mice showed significantly less muscle fatigue in response to repetitive challenge (16.3±5[male]/ 15.2±6[female]% versus 36.3%±6.5[male]/34.7%±5.7[female]; p<0.003 and p<0.009).

In order to demonstrate that phenotypic benefit from administration of losartan is derived from inhibition of the TGFβ signaling cascade immunofluorescent analysis of target proteins downstream of the angiotensin receptor II type 1 receptor (ATR1) was performed. It has recently been shown that thrombospondin-1 (TSP1) acts as a potent mediator of angiotensin II induced TGF-beta activation via AT I R (Zhou Y, et al. (2006) Biochem Biophys Res Commun. 339, 633-641). Wild-type mice did not express significant amounts of TSP1 in skeletal muscle (FIG. 14a). In contrast, we found strong sarcolemmal expression of TSP1 in the diaphragm and other muscles of mdx mice, whereas losartan-treated mdx mice exhibited greatly reduced expression of TSP1 (FIG. 14a). Moreover, treated mdx mice did not show any significant nuclear accumulation of pSmad2 or sarcolemmal expression of periostin (FIG. 14a). Activation of the AT1 receptor has been suggested to induce skeletal muscle breakdown by increasing ubiquitin-mediated proteolysis and subsequent inhibition of protein synthesis (Delafontaine P & M., A. (2006) Curr Opin Clin Nutr Metab Care. 9, 220-224). Inhibition of proteasome activity and ubiquitin-mediated proteolysis in mdx mice has been shown to be associated with increased expression of dystrophin and other members of the dystrophin-glycoprotein complex (Assereto S et al. (2006) Am J Physiol Cell Physiol. 290, C577-582). Therefore, the expression of dystrophin, a-dystroglycan and R-sarcoglycan in losartan-treated and untreated mdx mice was investigated. As expected, placebo-treated mdx mice showed absence of dystrophin and a significant reduction of sarcolemmal expression of a-dystroglycan and R-sarcoglycan (FIG. 18a). Identical findings were observed in losartan treated mdx mice, suggesting that losartan did not have any impact on ubiquitin mediated proteolysis. Together, these data demonstrate that losartan treatment inhibits the TGFβ signaling cascade and does not impact alternative proteolysis mediated pathways.

Figures 2, 14B:
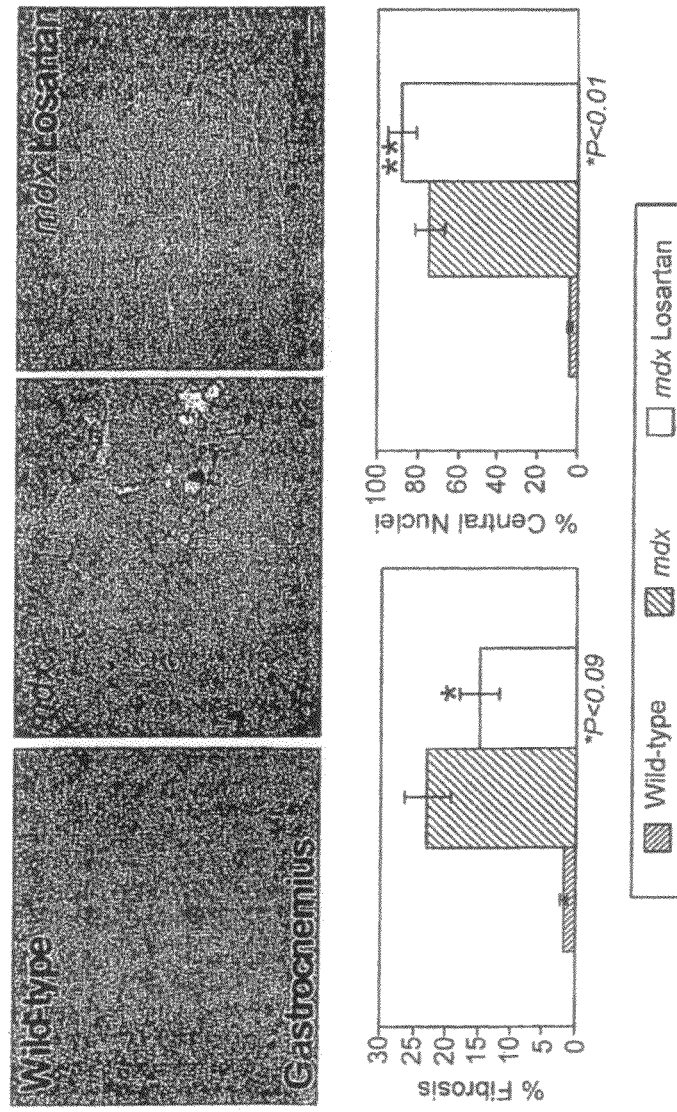
Figure 18B:
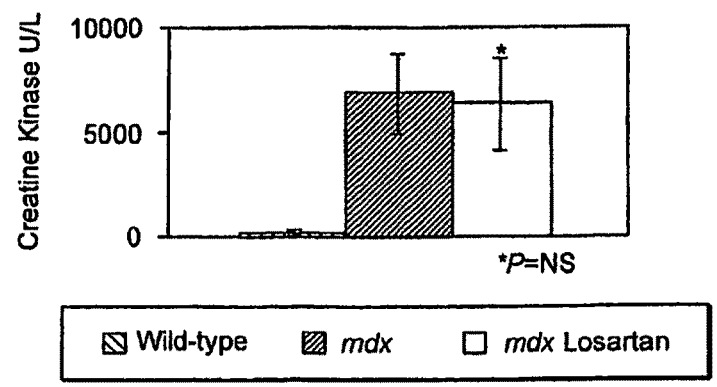

We next determined whether long-term treatment with losartan has a beneficial impact on steady-state architecture and in vivo muscle function of mdx mice. Losartan treatment commenced in mdx mice at 6 weeks of age, a time of active muscle necrosis associated with cycles of degeneration and regeneration (Cohn, R. D. et al. (2002) Cell 110, 639-48). After 6 months of treatment with losartan analysis of various muscle groups including the diaphragm (which is the most severely affected skeletal muscle in mdx mice) (Salvadori, C., et al. (2005) Muscle Nerve 31, 192-8; Cohn, R. D. et al. (2002) Cell 110, 63948) and gastrocnemius revealed significant attenuation of disease progression in mdx mice (FIG. 14b). Evaluation of tissue fibrosis in the diaphragm demonstrated a decrease to 18%±4 fibrosis of total muscle area in treated mice versus 32%±5 in placebo-treated mar mice (FIG. 14b, P<0.03). A similar decrease in the amount of tissue fibrosis was detected in the gastrocnemius muscle of losartan-treated mar mice (FIG. 14b). Moreover, we found an increased percentage of muscle fibers containing centrally located nuclei in the diaphragm and gastrocnemius of losartan-treated mice (FIG. 14b), an indirect indicator of increased regenerative capacity that may underlie the ameliorated phenotype. Analysis of creatine kinase (CK) levels in the serum, an indicator of sarcolemmal membrane leakage and destruction, did not show any significant differences between treated versus untreated mar mice (FIG. 18b). This is not surprising as we did not expect losartan to stabilize the sarcolemmal membrane or protect muscle fibers from contraction-induced damage.

Figure 18C:
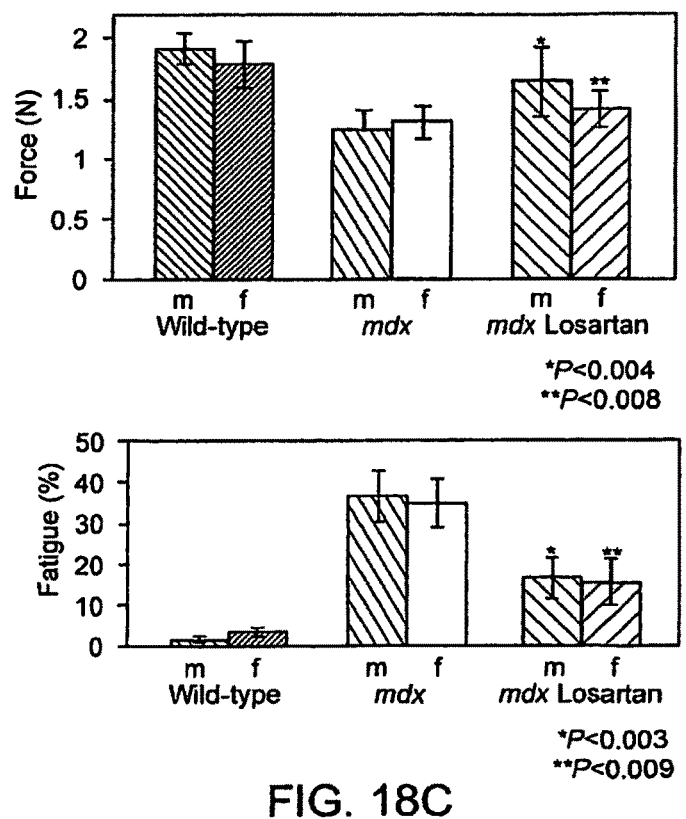

To further assess the functional benefit of losartan treatment in mdx mice we performed forelimb and hindlimb grip strength testing in male and female mice. Grip strength testing in mice has previously been used as a method to monitor in vivo muscle function data in models of muscular dystrophy, motor neuron diseases (wobbler mouse, SOD-1 deficient mice), and Down syndrome (Connolly A M, et al. (2001) Neuromuscul Disord. 11:703-12; Payne E T et al. (2006) Muscle Nerve. 33, 66-77; Hantai D et al. (1995) J Neurol Sci. 129, 122-126; Costa A C et al. (1999) Physiol Behav. 68, 211-220) After 6 months of treatment, male and female mdx mice treated with losartan showed increased forelimb and hindlimb grip strength when compared to untreated mdx mice (FIG. 14c; FIG. 18c).

In addition, losartan-treated mice showed significantly less muscle fatigue in response to repetitive challenge. In order to correlate our findings of functional improvement to muscle morphology, we evaluated the histology of the extensor digitorum, soleus and tibialis anterior muscles. As seen in the diaphragm and gastrocnemius muscles, losartan-treated mdx mice displayed improved steady-state architecture when compared to the placebo-treated group (FIG. 18c). The combination of improved muscle architecture, regenerative capacity as well as strength and decreased fatigue in a genetically defined mouse model of Duchenne muscular dystrophy highlights the therapeutic potential of losartan for the treatment of this disorder.

Excessive TGFβ signaling has been shown to drive pathology in multiple tissues in the Marfan syndrome, albeit by different mechanisms. In skeletal muscle we show that increased TGFβ activity does not simply drive late fibrosis, as previously inferred, but more importantly impedes the physiologic response of satellite cells to regenerate muscle in multiple genetically-defined forms of myopathy, a process essential for the preservation of muscle architecture and performance. While losartan does not address the underlying muscle fragility in mdx mice, the observations of an enduring improvement in muscle regeneration and function in this mouse model supports speculation that losartan will improve the quality of life and delay death in patients with Duchenne muscular dystrophy.

Example 3

Losartan, an AT1 Antagonist, Prevents Aortic Aneurysm in a Mouse Model of Marfan Syndrome We sought to determine the role of TGF-β in MFS-associated aortic aneurysm, which is the major life-threatening manifestation Marfan syndrome. Mice heterozygous for an Fbn1 allele encoding a cysteine substitution, Cys1039Gly (C1039G), in an epidermal growth factor-like domain of fibrillin-1 (Fbn1C1039G/+) (C. M. Ng et al., (2004) J. Clin. Invest. 114, 1586; D. P. Judge et al. (2004) J. Clin. Invest. 114, 172; K. B. Jones et al. (2005) Spine 30, 291.) were studied. This mutant represents the most common class of mutation causing MFS. The aortic root in Fbn1C1039G/+ mice undergoes progressive dilatation, evident as early as 2 weeks of age. By 7 weeks of age, the aortic root in the mutant mice is larger than that in wild-type mice (1.82±0.14 mm versus 1.59±0.11 mm, respectively; $P<0.05$). This size difference becomes more pronounced with age (aortic root at 8 months, 2.47±0.33 mm versus 1.82±0.11 mm; $P<0.0001$).

Histologic analysis of 14-week-old Fbn1C1039G/+ mice revealed aberrant thickening of the aortic media with fragmentation and disarray of elastic fibers. In addition, Fbn1C1039G/+ mice showed increased collagen deposition, which is an indirect marker of increased TGF-β signaling (P. Rossi et al. (1988) Cell 52,405; W. Schlumberger (1991) Arterioscler. Thromb. 11, 1660.). Phosphorylation and subsequent nuclear translocation of Smad2 (pSmad2), which are induced by TGF-β signaling (C. H. Heldin et al. (1997) Nature 390, 465), are markedly increased in the aortic media of Fbn1C1039G/+ mice relative to wild-type mice. Similar changes have been observed in aortic samples derived from patients with MFS (L. Loeys et al. (2005) Nat. Genet. 37, 275).

Figure 19I:
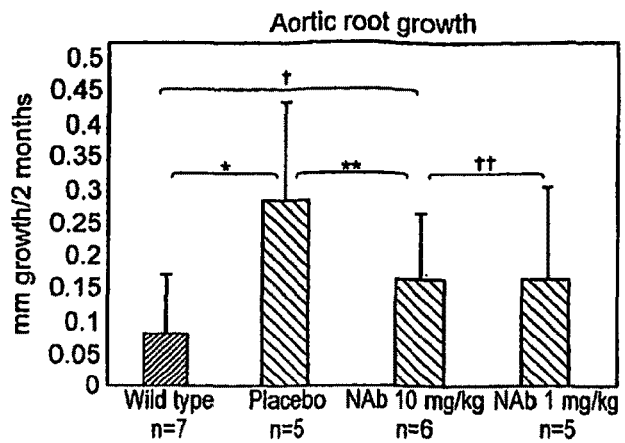
(FIG. 19I) Average aortic root growth (±SD) measured by echocardiogram over the 2-month treatment period. Note the reduced rate of growth in the NAb-treated mice relative to the placebo-treated Fbn1$^{C1039G/+}$ mice. *P<0.0001, **P<0.03, †P=0.11, ††P=1.0.
Figure 19J:
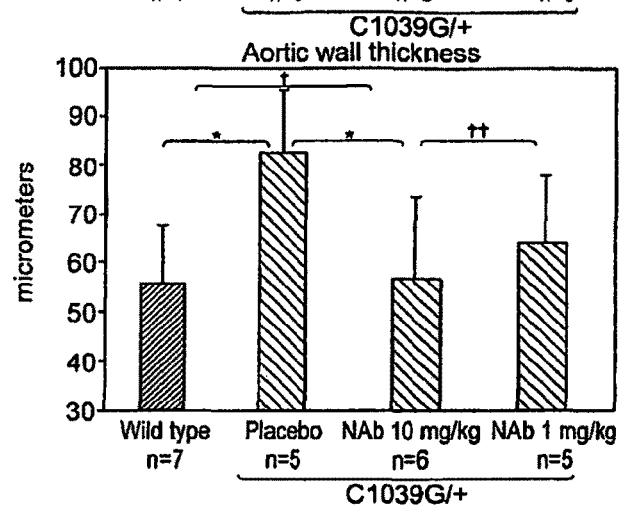
(FIG. 19J) Average thickness (±SD) of the proximal ascending aortic media of four representative sections measured by an observer blinded to genotype and treatment arm. Note full normalization of thickness in NAb-treated Fbn1$^{C1039G/+}$ mice. *P<0.01, †P=0.91, ††P=0.38.
Figure 19K:
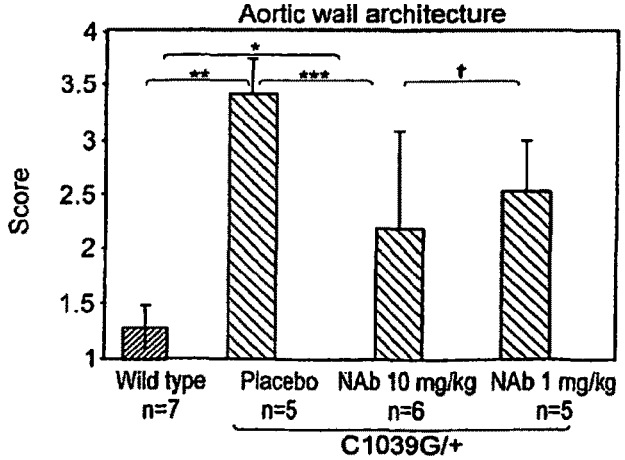
(FIG. 19K) Average aortic wall architecture score (±SD) of the proximal ascending aorta. Three separate observers who were blinded to genotype and treatment arm graded elastic fiber architecture in four representative areas on a scale from 1 (completely intact elastic lamellae) to 4 (extensive fragmentation). Note the improvement in NAb-treated Fbn1$^{C1039G/+}$ mice. *P<0.007, P<0.0001, *P<0.001, †P=0.21.
Figure 20A:
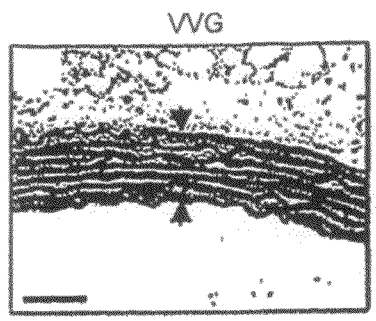
(FIG. 20A to FIG. 20D) VVG staining highlights intact elastic fiber architecture and normal ascending aortic wall thickness (arrows) in wild-type mice (FIG. 20A) and losartan-treated Fbn1$^{C1039G/+}$ mice (FIG. 20D). Marked elastic fiber disruption and wall thickening is apparent in the placebo- and propranolol-treated Fbn1$^{C1039G/+}$ mice [(FIG. 20B) and (FIG. 20C).] Scale bars, 40 μm.
Figure 20B:
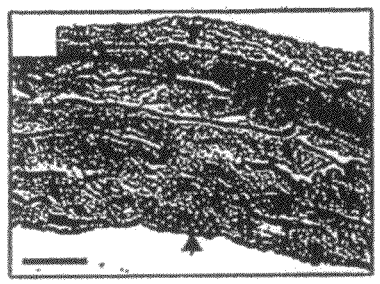
Figure 20C:
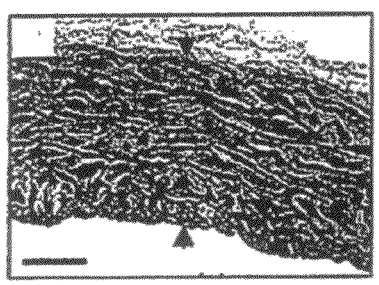
Figure 20D:
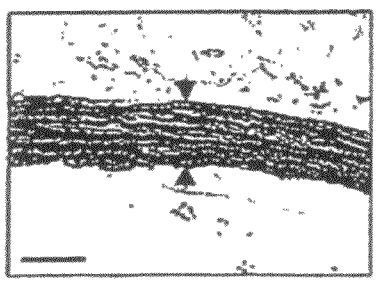
Figure 20E:
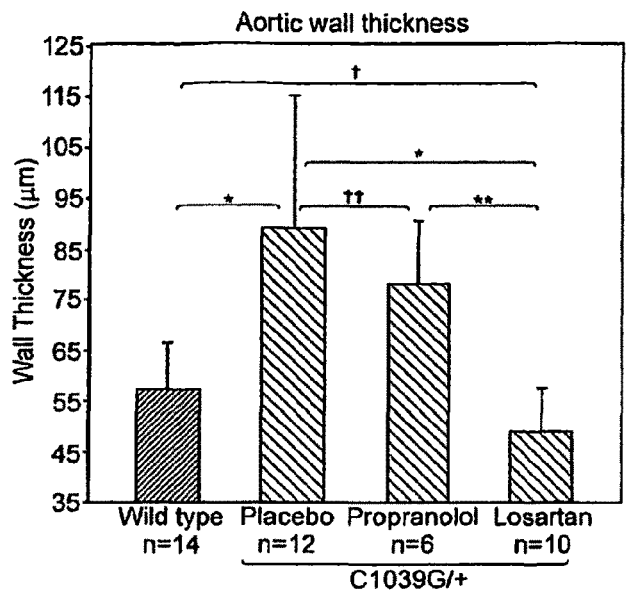
(FIG. 20E) Average aortic wall thickness (±SD) after 10 months of treatment. Note full normalization of wall thickness in losartan-treated Fbn1$^{C1039G/+}$ mice relative to mice that received placebo or propranolol treatment. *P<0.00001, **P<0.002, †P=0.24, ††P=0.19.
Figure 20F:
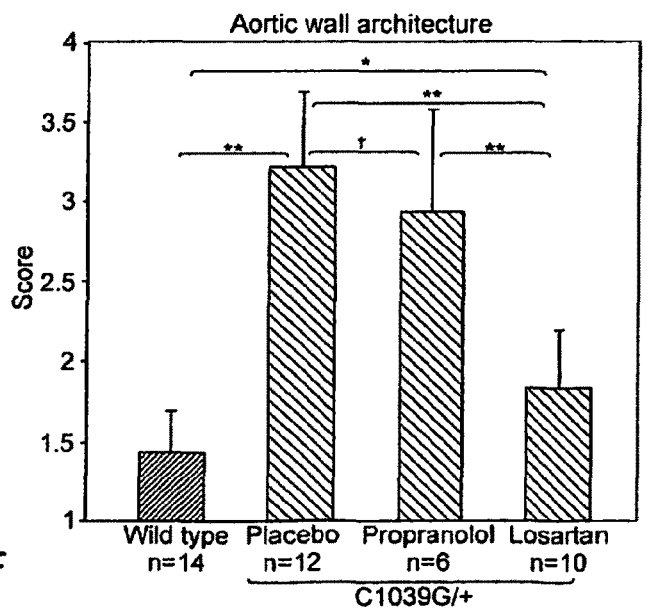
(FIG. 20F) Average aortic wall architecture score (±SD) after treatment. Note the improvement in losartan-treated Fbn1$^{C1039G/+}$ mice. *P<0.02, **P<0.0001, †P=0.16.

To investigate whether excessive TGF-β signaling plays a causal role in progressive aortic root enlargement, we treated mice postnatally with TGF-β NAb after the establishment of aortic root aneurysm (FIG. 19). Treatment by intraperitoneal injection was begun at 7 weeks of age and continued for 8 weeks. The Fbn1C1039G/+ mice received low-dose TGF-β NAb (1 mg/kg body weight; FIG. 19, C and G), high-dose TGF-β NAb (10 mg/kg; FIG. 19, D and H), or placebo (10 mg/kg rabbit IgG; FIG. 19, B and F) every 2 weeks. Histologic analyses revealed reduced elastic fiber fragmentation and reduced TGF-β signaling in the aortic media of TGF-β Nab-treated mice relative to the placebo group (FIG. 19A to H). In humans with MFS, the diameter and rate of enlargement of the aortic root are directly proportional to the risk of life-threatening aortic dissection (V. L. Gott et al. (1999) N. Engl. J. Med. 340, 1307).

Echocardiograms revealed that the aortic root diameter at baseline in the wild-type mice (1.57±0.05 mm) was smaller than that in the three Fbn1C1039G/+ treatment arms [placebo, 1.75±0.15 mm; NAb (10 mg/kg), 1.80±0.11 mm; NAb (1 mg/kg), 1.86±0.15 mm; $P<0.0001$ for each treatment arm relative to wild type]. There was no difference in the growth rate of the aortic root, as assessed by echocardiograms performed after 8 weeks of treatment, between wild-type mice and either of the TGF-β NAb treatment groups ($P=0.11$). In contrast, the aortic root growth rate in the placebo-treated mice was greater than that in either wild-type ($P<0.0001$) or NAb-treated mice ($P<0.03$, FIG. 19I). After 8 weeks, aortic wall thickness in NAb-treated Fbn1C1039G/+ mice was indistinguishable from that in untreated wild-type mice ($P=0.91$) and less than that in the placebo group ($P<0.01$, FIG. 19J). Aortic wall architecture was disrupted in Fbn1C1039G/+ mice relative to wild-type mice ($P<0.0001$) but improved in mutant mice treated with NAb ($P<0.001$, FIG. 19K). These data show that excessive TGF-β signaling contributes to the formation of aortic aneurysm in a mouse model of MFS, and that TGF-β antagonism represents a productive treatment strategy.

We became interested in losartan, an angiotensin II type 1 receptor (AT1) antagonist, not only because it lowers blood pressure—a desirable effect in patients with aortic aneurysm—but also because it leads to antagonism of TGF-β in animal models of chronic renal insufficiency and cardiomyopathy (P. Lavoie et al. (2005) J. Hypertens. 23, 1895; D. S. Lim et al. (2001) Circulation 103, 789). Using a prenatal administration protocol in our mouse model, we compared the efficacy of losartan to that of propranolol, which is representative of β-adrenergic blocking agents widely used in patients with MFS to slow the rate of aortic growth (J. Shores (1994) N. Engl. J. Med. 330, 1335). The doses of losartan and propranolol were titrated to achieve comparable hemodynamic effects in vivo, including a 15 to 20% decrease in heart rate and a 10 to 20% decrease in blood pressure in both groups.

Pregnant Fbn1C1039G/+ mice received losartan (0.6 g/liter), propranolol (0.5 g/liter), or placebo in their drinking water, beginning at 2 weeks of gestation. Treatment of the mothers continued throughout lactation and was maintained in the pups after weaning. Mice were killed at 10 months of age. Elastic fiber fragmentation was observed in both placebo- and propranolol-treated mice, but not in losartan-treated mice (FIG. 20, A to D). The average aortic wall thickness for untreated wild-type animals was smaller than that in placebo-treated Fbn1C1039G/+ mice ($P<0.0001$) but was indistinguishable from that in losartan-treated Fbn1C1039G/+ mice ($P=0.24$, FIG. 20E). Aortic wall thickness in the propranolol-treated mice was indistinguishable from that in the placebo group ($P=0.19$). Likewise, aortic wall architecture was normalized in losartan-treated Fbn1C1039G/+ animals relative to the placebo group ($P<0.0001$) but was not influenced by propranolol ($P=0.16$, FIG. 20F). There was marked aortic dilatation in the placebo- and propranolol-treated mutant mice, whereas the losartan-treated mutant mice were indistinguishable from wild-type littermates.

Because MFS is typically diagnosed after birth and because the use of AT1 antagonists is contraindicated during pregnancy (S. G. Spence et al. (1995) Teratology 51, 367), we investigated whether losartan could attenuate or prevent abnormal aortic root growth if treatment were initiated postnatally, after the establishment of aortic aneurysms. At 7 weeks of age, after echocardiographic documentation of aneurysm, Fbn1C1039G/+ mice received placebo, propranolol (0.5 g/liter), or losartan (0.6 g/liter) in their drinking water. Baseline echocardiograms revealed no differences in aortic root size between any of the treatment groups for Fbn1C1039G/+ mice (placebo 1.83±0.11 mm, propranolol 1.92±0.27 mm, losartan 1.84±0.08 mm, respectively; P=0.5). However, before treatment, the aortic diameter in Fbn1C1039G/+ mice was always greater than in untreated wild-type mice (1.59±0.11 mm; P<0.002).

Figure 21I:
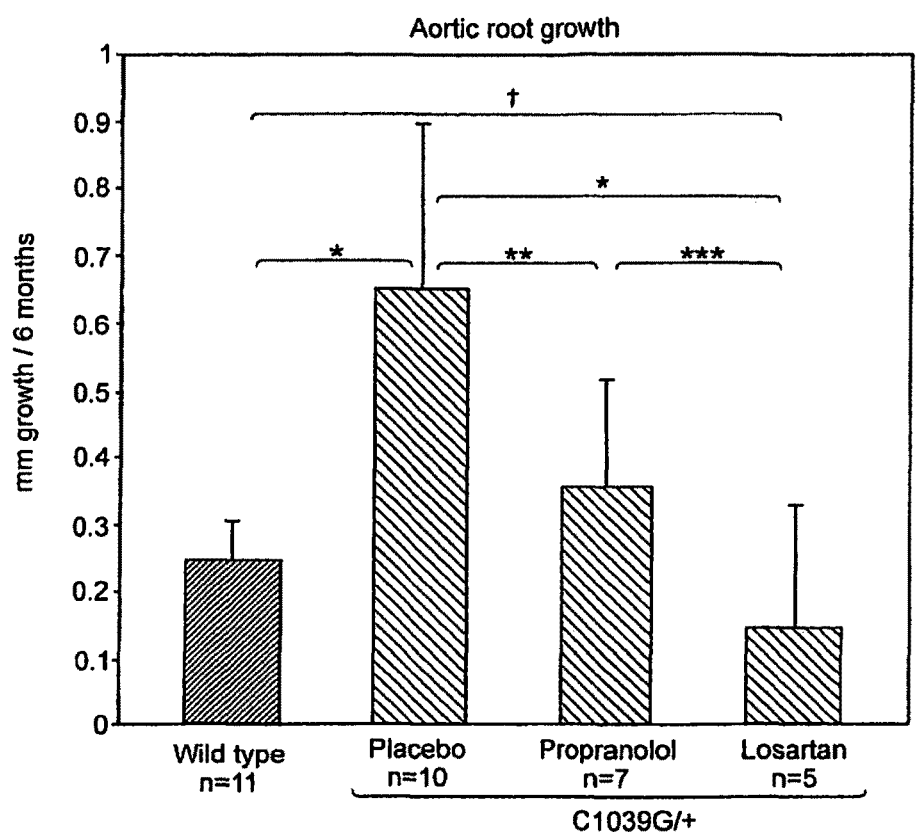
Figure 21J:
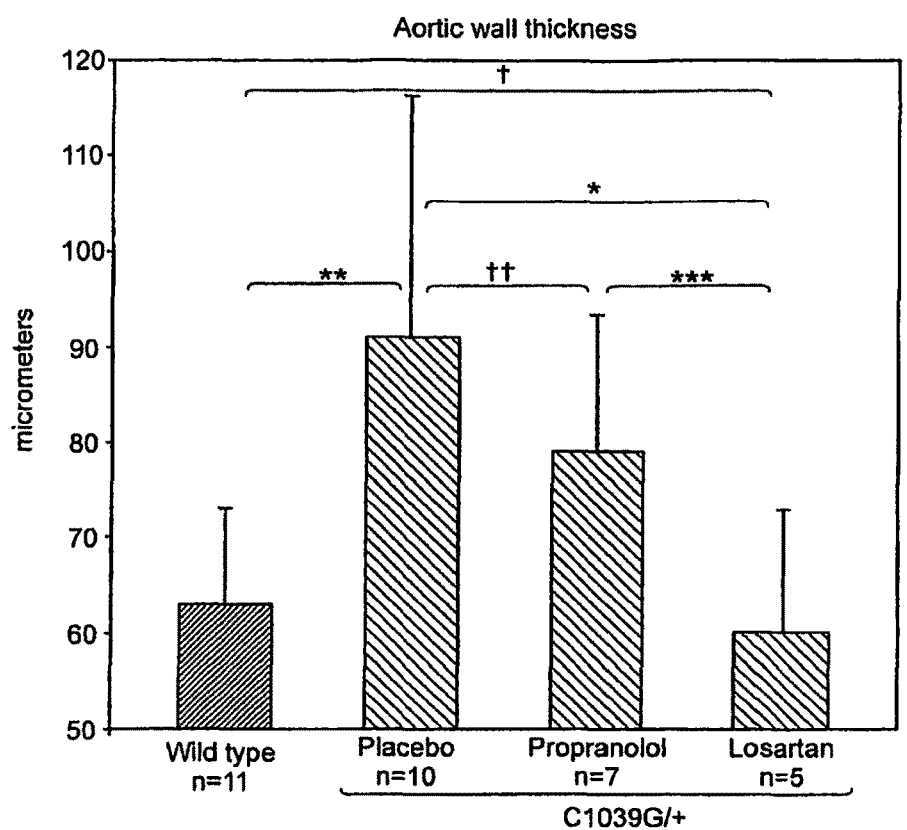
Figure 21K:
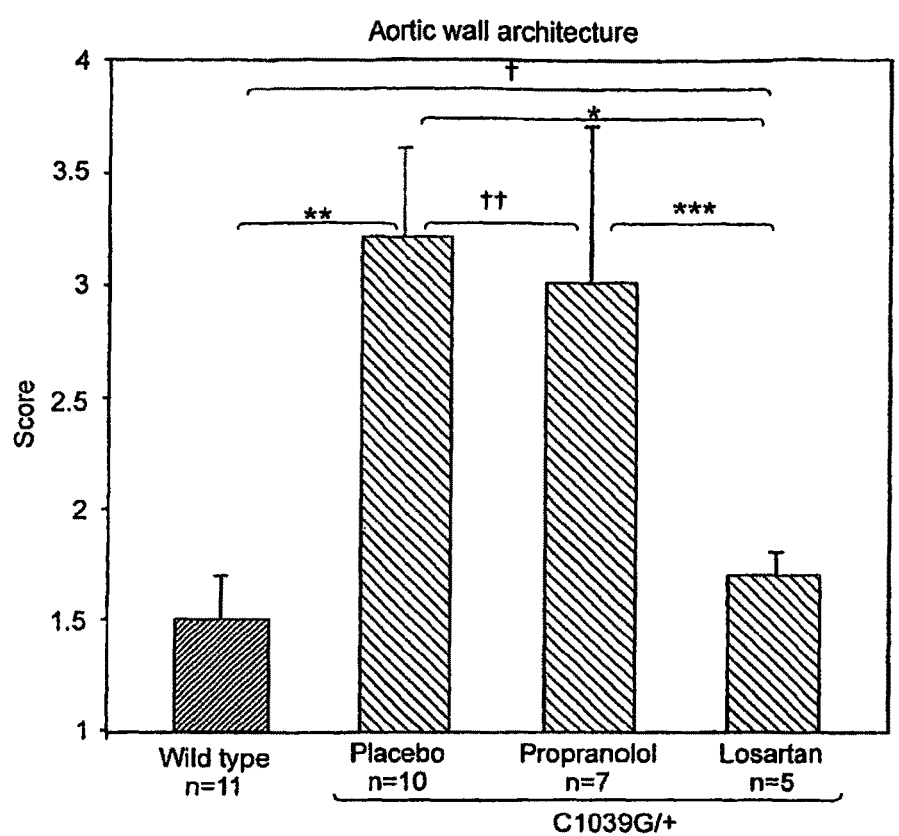
Figure 22B:
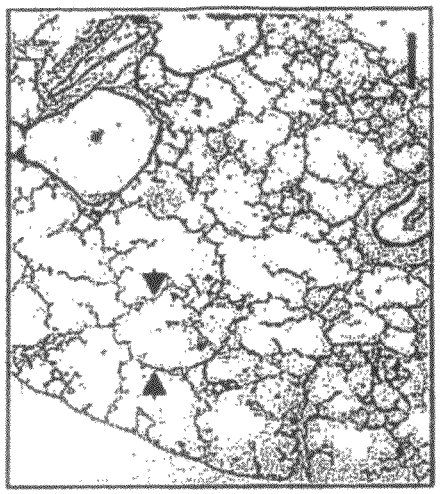
FIGS. 22 A-D depict postnatal losartan treatment of lung disease in Fbn1$^{C1039G/+}$ mice. Histologic analysis of lung in wild-type mice (A) shows normal airspace caliber. Fbn1$^{C1039G/+}$ mice treated with placebo (B) show diffuse distal airspace widening (example delineated with arrows). Distal airspace caliber is reduced in Fbn1$^{C1039G/+}$ mice treated with losartan (C). Scale bars, 500 μm. (D) Average mean linear intercept, a marker of airspace caliber, is greater for placebo-treated Fbn1$^{C1039G/+}$ mice than for untreated wild-type and losartan-treated Fbn1$^{C1039G/+}$ mice. *P<0.01, **P<0.001.
Figure 22A:
Figure 22C:
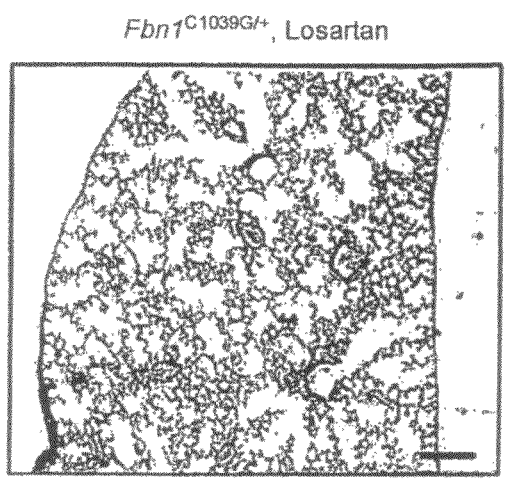
Figure 22D:
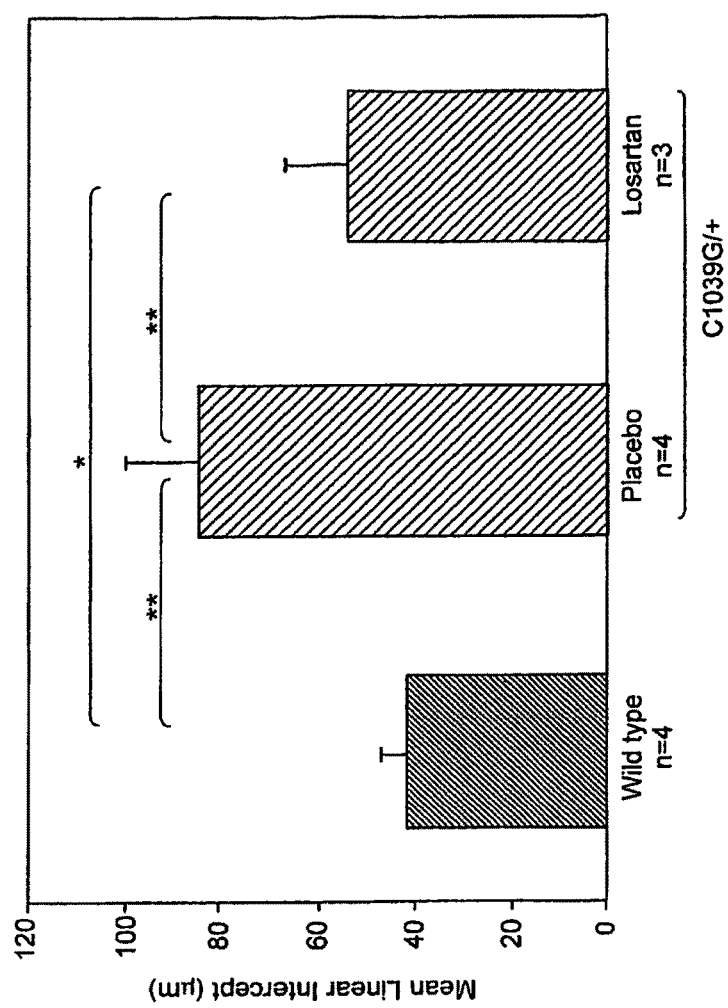

Three independent aortic root measurements were obtained for each mouse every 2 months during the 6 months of treatment. Mice were killed at 8 months of age. In contrast to propranolol or placebo, losartan treatment prevented elastic fiber fragmentation (FIG. 21, A to D) and blunted TGF-β signaling in the aortic media, as evidenced by reduced nuclear accumulation of pSmad2 (FIG. 21, E to H). The aortic root growth rate over this period was less in the wild-type mice than in the placebo-treated Fbn1C1039G/+ mice (P<0.0001, FIG. 21I). Although the propranolol-treated Fbn1C1039G/+ mice did show a slower rate of aortic root growth than did placebo-treated animals (P<0.001), this growth rate remained greater than that in untreated wild-type mice (P<0.04).

In contrast, the aortic root growth rate in losartan-treated Fbn1C1039G/+ mice was indistinguishable from that in the wild-type group (P=0.55, FIG. 21I). Furthermore, the absolute diameter of the aortic root at the end of treatment was similar in the losartan-treated Fbn1C1039G/+ mice and untreated wild-type littermates (P=0.32). Propranolol had no discernable effect on either aortic wall thickness or elastic fiber architecture when compared to placebo; hence, its beneficial effect is limited to slowing the rate of growth of the aortic root. In contrast, losartan-treated Fbn1C1039G/+ mice showed improvement in all three parameters compared to placebo-treated mice, with full normalization relative to wild-type mice (FIG. 21, I to K). We conclude that l3-adrenergic blockade with propranolol diminishes aortic growth rate in this model of MFS but does not prevent progressive deterioration of aortic wall architecture or ongoing abnormal aortic dilatation. In contrast, AT1 blockade with losartan appears to achieve full correction of the phenotypic abnormalities in the aortic wall of Fbn1C1039G/+ mice.

In a previous study, it was demonstrated that a different strain of mice homozygous for hypomorphic Fbn1 alleles showed widening of the distal airspace due to failure of alveolar septation (E. R. Neptune et al. (2003) Nat. Genet. 33, 407). This abnormality correlated with increased TGF-β signaling and was prevented by prenatal administration of TGF-β NAb. To determine whether losartan can improve this lung phenotype when administered postnatally—a matter of specific relevance to patients with MFS—we treated Fbn1C1039G/+ mice with losartan beginning at 7 weeks of age. After 6 months of treatment, placebo-treated Fbn1C1639G/+ mice showed widening of the distal airspace due to impaired alveolar septation (mean linear intercept 84.3±15 µm) relative to wild-type placebo-treated mice (mean linear intercept 41.3±5 µm, P<0.001; FIG. 22). Losartan-treated Fbn1C1039G/+ mice showed a reduction in distal airspace caliber relative to placebo-treated Fbn1C1039G/+ animals (mean linear intercept 53.9±12 µm, P<0.001; FIG. 22).

AT1 antagonism might achieve superior protection over β-adrenergic blocking agents by virtue of increased blunting of the hemodynamic stress that is imposed on a structurally deficient aortic wall, as opposed to a mechanism relevant to TGF-β signaling or other molecular pathogenetic events. Four lines of evidence argue against this hypothesis. First, the doses of losartan and propranolol were titrated to achieve comparable hemodynamic effects. Second, isolated antagonism of TGF-β signaling with NAb provides similar protection. Third, analysis of pSmad2 nuclear staining revealed that losartan antagonizes TGF-β signaling in the aortic wall of Fbn1C1039G/+ mice, an event seen in NAb-treated mice but not in propranolol-treated mice (FIG. 21, G and H). Fourth, we demonstrate here that losartan can improve disease manifestations in the lungs (FIG. 22), an event that cannot plausibly relate to improved hemodynamics.

The mechanism by which AT1 blockade antagonizes TGF-β signaling remains to be fully elucidated. Signaling through the AT1 receptor increases the expression of TGF-β ligands and receptors and also induces the expression of thrombospondin-1, a potent activator of TGF-β (A. D. Everett (1994) Hypertension 23, 587; G. Wolf et al. (1999) J. Mol. Med. 77, 556; N. Fukuda et al. (2000) Am. J. Hypertens. 13, 191; T. Naito et al. (2004) Am. J. Physiol. Renal Physiol. 286, F278). In the vessel wall, AT1 signaling stimulates proliferation of vascular smooth muscle cells (VSMCs) and vessel wall fibrosis (E. G. Nabel et al. (1993) Proc. Natl. Acad. Sci. U.S.A. 90, 10759), although this may be context-dependent. In avian systems, neural crest- and mesoderm-derived VSMCs (N- and M-VSMCs, respectively) respond differently to TGF-β1, with cellular proliferation and fibrosis seen in the former and growth inhibition seen in the latter (P. F. Gadson Jr. et al. (1997) Exp. Cell Res. 230, 169; S. Topouzis et al. (1996) Dev. Biol. 178, 430). This differential response may explain the particular predisposition of the root of the aorta—a vascular segment enriched for N-VSMCs—to undergo dilatation and dissection in MFS. The pulmonary artery root is also enriched for N-VSMCs and routinely shows dilatation in MFS despite the reduced pressure in the pulmonary circulation (G. J. Nollen et al. (2002) Heart 87, 470).

Given that signaling through the angiotensin II type 2 receptor (AT2) antagonizes many of the effects that are promoted by AT1 signaling (E. S. Jones et al. (2004) J. Mol. Cell. Cardiol. 37, 1023), specific AT1 antagonism may be preferable to the dual AT1/AT2 blockade achieved with angiotensin converting enzyme (ACE) inhibitors. Consistent with this hypothesis, Daugherty and colleagues found that the formation of angiotensin II-induced abdominal aortic aneurysms could be prevented in apoE−/− mice by treatment with AT1 antagonists but was accelerated in both frequency and severity upon treatment with a selective AT2 blocker (A. Daugherty et al. (2001) Br. J. Pharmacol. 134, 865). Nagashima and colleagues observed increased apoptosis in vessel wall explants and cultured VSMCs from individuals with MFS, and they showed that AT2 but not AT1 blockade reduced this effect (H. Nagashima et al. (2001) Circulation 104, 1282). These samples were derived from aneurysms in the 7- to 9-cm range, far beyond the current threshold for aortic root surgery. In our mouse model, we have not detected enhanced apoptosis in early and intermediate stages of aortic aneurysm. Angiotensin II also stimulates Smad2-dependent signaling and fibrosis in VSMCs in a TGF-β-independent manner, and this effect can be prevented by selective AT1 blockade (J. Rodriguez-Vita et al. (2005) Circulation 2059). Thus, although TGF-β ligand-dependent signaling appears critical to the pathogenesis of aortic aneurysm in MFS, antagonism of a parallel pSmad2-mediated signaling cascade may contribute to the protection afforded by losartan.

The demonstration of excess TGF-β signaling in the aortic wall of patients with other aortic aneurysm syndromes, including Loeys-Dietz syndrome (caused by mutations in TGFBR1 or TGFBR2) and arterial tortuosity syndrome (caused by mutations in GLUT10), suggests that losartan may be of broad relevance in the treatment of human vasculopathies (B. L. Loeys et al. (2005) Nat. Genet. 37, 275).

Losartan is currently in widespread clinical use for treatment of hypertension and prevention of strokes in both adults and children. Given its exceptional tolerance profile in all age groups, we conclude that a prospective clinical trial in patients with MFS is indicated. Furthermore, this study is illustrative of the promise that enhanced identification of disease genes in the post-genome sequencing era will have a pronounced impact on medicine. Disease gene discovery is but an obligate first step in the process of making animal models, interrogating pathogenesis, and deriving unanticipated disease mechanisms and rational treatment strategies.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method of treating a subject having a Marfan-associated condition selected from the group consisting of aneurysm, an aortic aneurysm, emphysema, valve disease, hypotonia, and myopathy comprising:

administering to the subject post-natally an effective amount of an antibody or antibody fragment selected from the group consisting of an F(ab) fragment, F(ab)$_2$ fragment, Fv fragment, or a single chain antibody that binds and neutralizes TGFβ; thereby treating the subject.

* * * * *